(12) United States Patent
Coulombe et al.

(10) Patent No.: US 7,816,348 B2
(45) Date of Patent: Oct. 19, 2010

(54) VIRAL POLYMERASE INHIBITORS

(75) Inventors: Rene Coulombe, Montreal (CA); Gulrez Fazal, Roxboro (CA); Jean Rancourt, Montreal (CA); Timothy Stammers, Rosemére (CA); Bounkham Thavonekham, Longueuil (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 672 days.

(21) Appl. No.: 11/668,197

(22) Filed: Jan. 29, 2007

(65) Prior Publication Data

US 2007/0219176 A1 Sep. 20, 2007

Related U.S. Application Data

(60) Provisional application No. 60/764,978, filed on Feb. 3, 2006.

(51) Int. Cl.
*A61K 31/5355* (2006.01)
*A61K 31/5513* (2006.01)
*C07D 401/04* (2006.01)
*C07J 43/00* (2006.01)

(52) U.S. Cl. .................. 514/218; 514/231.2; 540/107; 544/360

(58) Field of Classification Search ................ 514/218, 514/231.2; 540/107; 544/575
See application file for complete search history.

(56) References Cited

U.S. PATENT DOCUMENTS

| | | | |
|---|---|---|---|
| 4,062,682 A | 12/1977 | Laridon et al. | |
| 4,740,519 A | 4/1988 | Shroot et al. | |
| 5,633,388 A | 5/1997 | Diana et al. | |
| 6,434,489 B1 | 8/2002 | Lesburg et al. | |
| 6,878,727 B2 | 4/2005 | Borchardt et al. | |
| 7,112,600 B1 | 9/2006 | Hashimoto et al. | |
| 7,386,398 B2 | 6/2008 | Coulombe et al. | |
| 2003/0236251 A1 | 12/2003 | Beaulieu et al. | |
| 2004/0082635 A1 | 4/2004 | Hashimoto et al. | |
| 2005/0003348 A1 | 1/2005 | Coulombe et al. | |
| 2007/0219176 A1 | 9/2007 | Coulombe et al. | |
| 2008/0045516 A1 | 2/2008 | Beaulieu et al. | |

FOREIGN PATENT DOCUMENTS

| CA | 2412718 A1 | 1/2002 |
|---|---|---|
| CA | 2450033 A1 | 6/2003 |
| CA | 2511301 A1 | 8/2004 |
| EP | 1256628 A2 | 11/2002 |
| EP | 1688420 A1 | 8/2006 |
| WO | 9907733 A2 | 2/1999 |
| WO | 9907734 A2 | 2/1999 |
| WO | 0009543 A2 | 2/2000 |
| WO | 0009558 A1 | 2/2000 |
| WO | 0059929 A1 | 10/2000 |
| WO | 0147883 | 7/2001 |
| WO | 0177113 A2 | 10/2001 |
| WO | 0181325 A2 | 11/2001 |
| WO | 0204425 | 1/2002 |
| WO | 0208187 A1 | 1/2002 |
| WO | 0208198 A2 | 1/2002 |
| WO | 0208244 A2 | 1/2002 |
| WO | 0208256 A2 | 1/2002 |
| WO | 0248172 A2 | 6/2002 |
| WO | 02060926 A2 | 8/2002 |
| WO | 03000254 | 1/2003 |
| WO | 03004458 A1 | 1/2003 |
| WO | 03007945 A1 | 1/2003 |
| WO | 03010140 A2 | 2/2003 |
| WO | 03010141 A2 | 2/2003 |
| WO | 03026587 | 4/2003 |
| WO | 03053349 A2 | 7/2003 |
| WO | 03062228 A1 | 7/2003 |
| WO | 03062265 A2 | 7/2003 |
| WO | 03064416 A1 | 8/2003 |
| WO | 03064455 A2 | 8/2003 |
| WO | 03064456 A1 | 8/2003 |
| WO | 03099274 A1 | 12/2003 |
| WO | 03099316 A1 | 12/2003 |
| WO | 03101993 | 12/2003 |
| WO | 2004030670 A1 | 4/2004 |
| WO | 2004032827 A2 | 4/2004 |
| WO | 2004037855 A1 | 5/2004 |
| WO | 2004039833 A1 | 5/2004 |
| WO | 2004043339 A2 | 5/2004 |
| WO | 2004064925 A1 | 8/2004 |
| WO | 2004065367 A1 | 8/2004 |

(Continued)

OTHER PUBLICATIONS

McKercher et al, Specific inhibitors of HCV polymerase identified using an NS5B with Lower affinity for template/ primer substrare, "Nucleic Acids Research" vol. 32 (2) pp. 422-431, 2004 (abstract and discussion).

Llinas-Brunet et al., Highly Potent and Selective Peptide-Based Inhibitors of the Hepatitis C virus Serine Protease: Towards Smaller Inhibitors, "Bioorganic & Medicinal Chemistry Letters" vol. 10 (20) pp. 2267-2270, 2000 (abstract and discussion).

(Continued)

*Primary Examiner*—Taofiq A Solola
(74) *Attorney, Agent, or Firm*—Michael P. Morris; Mary-Ellen M. Devlin; David A. Dow

(57) ABSTRACT

Compounds of formula I:

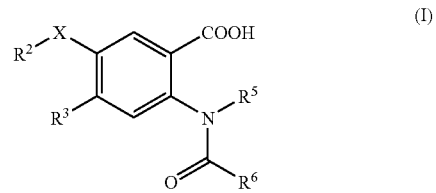

wherein X, $R^2$, $R^3$, $R^5$ and $R^6$ are defined herein, are useful as inhibitors of the hepatitis C virus NS5B polymerase.

24 Claims, No Drawings

FOREIGN PATENT DOCUMENTS

| | | |
|---|---|---|
| WO | 2004072243 A2 | 8/2004 |
| WO | 2004087714 | 10/2004 |
| WO | 2004093798 A2 | 11/2004 |
| WO | 2004094452 A2 | 11/2004 |
| WO | 2004099241 A1 | 11/2004 |
| WO | 2004101602 A2 | 11/2004 |
| WO | 2004101605 A1 | 11/2004 |
| WO | 2004103996 A1 | 12/2004 |
| WO | 2004113365 A2 | 12/2004 |
| WO | 2005010029 A1 | 2/2005 |
| WO | 2005012288 A1 | 2/2005 |
| WO | 2005014543 | 2/2005 |
| WO | 2005021584 A2 | 3/2005 |
| WO | 2005028501 A1 | 3/2005 |
| WO | 2005030796 A1 | 4/2005 |
| WO | 2005037214 A2 | 4/2005 |
| WO | 2005046712 A1 | 5/2005 |
| WO | 2005049622 A1 | 6/2005 |
| WO | 2005051410 A1 | 6/2005 |
| WO | 2005051980 A1 | 6/2005 |
| WO | 2005054430 A2 | 6/2005 |
| WO | 2005058821 A1 | 6/2005 |
| WO | 2005070955 A1 | 8/2005 |
| WO | 2005080388 A1 | 9/2005 |
| WO | 2005085197 A1 | 9/2005 |
| WO | 2005085242 A1 | 9/2005 |
| WO | 2005085275 A1 | 9/2005 |
| WO | 2005087721 A2 | 9/2005 |
| WO | 2005087725 A2 | 9/2005 |
| WO | 2005087730 A1 | 9/2005 |
| WO | 2005087731 A1 | 9/2005 |
| WO | 2005107745 A1 | 11/2005 |
| WO | 2005113581 A1 | 12/2005 |
| WO | 2005121132 A1 | 12/2005 |
| WO | 2006000085 A1 | 1/2006 |
| WO | 2006007693 A1 | 1/2006 |
| WO | 2006007700 A1 | 1/2006 |
| WO | 2006007708 A1 | 1/2006 |
| WO | 2007087717 A1 | 8/2007 |
| WO | 2008019477 A1 | 2/2008 |
| WO | 2009018656 A1 | 2/2009 |
| WO | 2009018657 A1 | 2/2009 |
| WO | 2009076747 A1 | 6/2009 |

OTHER PUBLICATIONS

Faucher et al, Synthesis of BILN 2061, an HCV NS3 Protease Inhibitor with Proven Antiviral Effect in Humans, "Organic Letters" vol. 6 (17) pp. 2901-2904, 2004 (abstract and discussion).

Beaulieu et al., Non-nucleoside inhibitors of the hepatitis C virus NS5B polymerase: discovery of benzimidazole 5-carboxylic amide derivatives with low-nanomolar potency, "Biorganic & Medicinal Chemistry Letters" vol. 14 (4) pp. 967-971 (2004) (abstract and discussion).

Beaulieu et al., Inhibitors of the HCV NS5B polymerase: New hope for the treatment of hepatitis C infections, "Current Opinion in Investigational Drugs" vol. 5 (8) pp. 838-850, 2004 (abstract and discussion).

International Search Report PCT/CA2007/000144.

Abdel-Magid, A.F., et al., "Reductive Amination of Aldehydes and Ketones with Sodium Triacetoxyborohydride. Studies on Direct and Indirect Reductive Amination Procedures", J. Org. Chem., 1996, vol. 61, p. 3849.

Ago, H.,et al. "Crystal Structure of the RNA-dependent RNA Polymerase of Hepatitis C Virus", Structure, vol. 7, No. 11, pp. 1417-1426, USA, Nov. 1999.

Beaulieu, P. L., "Finger loop inhibitors of the HCV NS5B polymerase: Discovery and prospects for new HCV therapy", Curr. Opin. Drug Discovery & Development, 2006, vol. 9, No. 5, p. 618.

Beaulieu, P. L., "Non-nucleoside inhibitors of the HCV NS5B polymerase: Progress in the discovery and development of novel agents for the treatment of HCV infections", Curr. Opin. Investigational Drugs, 2007, vol. 8, No. 8, p. 614.

Beaulieu, P. L., "The discover of finger loop inhibitors of the hepatitis C virus NS5B polymerase: Status and prospects for novel HCV therapeutics", IDRUGS, 2006, vol. 9, No. 1, p. 39.

Berge, S. M., et al., "Pharmaceutical Salts", Journal of Pharmaceutical Sciences, 1977, vol. 66, No. 1, p. 1.

Bowie, et al., "Deciphering the message in protein sequences: tolerance to amino acide substitutions". Science, vol. 247, No. 4948, Mar. 1990, pp. 1306-1310.

Bressanelli, S., et al. "Crystal Structure of the RNA-dependent RNA Polymerase of Hepatitis C Virus", PNAS, vol. 96, No. 23, pp. 13034-13039, USA, Nov. 1999.

Bressanelli, S., et al. "Structural Analysis of the Hepatitis C Virus RNA Polymerase in Complex with Ribonucleotides", J. Virology. vol. 76, No. 7, pp. 3482-3492, USA, Apr. 2002.

Buck, E., et al., "Preparation of 1-Methoxy-2-(4-Methoxyphenoxy) Benzene", Org. Syntheses, 2005, vol. 82, p. 69.

Caplus: Hemalatha, R. et al., "QSAR Analysis of 5-substituted-2-Benzoylaminobenzoic acids as PPAR Modulator", E-Journal of Chemistry, 2004, vol. 1, No. 5, p. 243-250S.

Di Marco, S., et al., "Interdomain Communication in Hepatitis C Virus Polymerase Abolished by Small Molecule Inhibitors Bound to a Novel Allosteric Site", J. Biological Chemistry, 2005, vol. 280, No. 33, p. 29765.

Giuliano, C. et al., "Preclinical pharmacokinetics and metabolism of a potent non-nucleoside inhibitor of the hepatitis C virus NS5B polymerase" Xenobiotica, 2005, vol. 35, No. 10, p. 1035.

Harper, S. et al., "Development and Preliminary Optimization of Indole-N-Acetamide Inhibitors of Hepatitis C Virus NS5B Polymerase", J. Medicinal Chemistry, 2005, vol. 48, p. 1314.

Harper,S., et al., "Potent Inhibitors of Subgenomic Hepatitis C Virus RNA Replication through Optimization of Indole-N-Acetamide Allosteric inhibitors of the Viral NS5B polymerase", J. Medicinal Chemistry, 2005, vol. 48, p. 454.

Hennessy, E.J., et al., "A General and Mild Copper-Catalyzed Arylation of Diethyl Malonate", Organic Letters, 2002, vol. 4, No. 2, p. 269.

Kolykhalov, A.A., et al., "Hepatitis C Virus-Encoded Enzymatic Activities and Conserved RNA Elements in the 3' Nontranslated Region are Essential for Virus Replication in Vivo", J. Virology, 2000, vol. 74, No. 4, p. 2046.

Labonte, P., et al. "Modulation of Hepatitis C Virus RNA-dependent RNA Polymerase Activity by Structure-based Site-directed Mutagenesis", J. Bio. Chem. vol. 277, No. 41, Issue of Oct. 11, pp. 38838-38846, USA, 2002.

Lesburg, C. A., et al. "Crystal Structure of the RNA-dependent RNA Polymerase from Hepatitis C Virus Reveals a Fully Encircled Active Site", Nature Structural Biology, vol. 6, No. 10, pp. 937-943, USA, Oct. 1999.

Oestberg, T. et al., "A New Class of Peroxisome Proliferator-activated Receptor Agonists with a novel Binding Epitope Shows Antidiabetic Effects", J. Biological Chemistry, 2004, vol. 279, No. 39, p. 41124.

Still, W.C.,et al., "Rapid Chromatographic Technique for Preparative Separations with Moderate Resolution", J. Org. Chem., 1978, vol. 43, No. 14, p. 2923.

Takagi, K., "Synthesis of Aromatic Thiols from Aryl Iodides and Thiourea by Means of Nickel Catalyst", Chemistry Letters, 1985, p. 1307.

Tanaka, K. et al., "Synthesis and Reaction of 5-Amino-3-trifluoromethylisoxazole and -pyrazole-4-carboxylic Acids", J. Heterocyclic Chem., 1986, vol. 23, p. 1535.

Thor, M., et al., "Synthesis and Pharmacological Evaluation of a New Class of Peroxisome Proliferator-Activated Receptor Modulators", Bioorganic and Medicinal Chemistry Letters, 2002, vol. 12, p. 3565.

Tomei, L., et al. "Mechanism of Action and Antiviral Activity of Benzimidazole-Based Allosteric Inhibitors of the Hepatitis C Virus RNA-Dependent RNA Polymerase" Journal of Virology, vol. 77, No. 24, pp. 13225-13231, USA, Dec. 2003.

Zurawski, et al., "Definition and spatial locatin of mouse interleukin-2-residues that interact with its heterotrimeric receptor." The EMBO Journal, vol. 12, No. 13, Dec. 1993, pp. 5113-5119.

VIRAL POLYMERASE INHIBITORS

RELATED APPLICATIONS

This application claims benefit of U.S. Ser. No. 60/764,978, filed Feb. 3, 2006, the contents of which are incorporated herein in its entirety.

FIELD OF THE INVENTION

The present invention relates to compounds, compositions and methods for the treatment of hepatitis C virus (HCV) infection. In particular, the present invention provides novel inhibitors of the hepatitis C virus NS5B polymerase, pharmaceutical compositions containing such compounds and methods for using these compounds in the treatment of HCV infection.

BACKGROUND OF THE INVENTION

It is estimated that at least 130 million persons worldwide are infected with the hepatitis C virus (HCV). Acute HCV infection progresses to chronic infection in a high number of cases, and, in some infected individuals, chronic infection leads to serious liver diseases such as cirrhosis and hepatocellular carcinoma.

Currently, standard treatment of chronic hepatitis C infection involves administration of pegylated interferon-alpha in combination with ribavirin. However, this therapy is not effective in reducing HCV RNA to undetectable levels in many infected patients and is associated with often intolerable side effects such as fever and other influenza-like symptoms, depression, thrombocytopenia and hemolytic anemia. Furthermore, some HCV-infected patients have co-existing conditions which contraindicate this treatment.

Therefore, a need exists for alternative treatments for hepatitis C viral infection. One possible strategy to address this need is the development of effective antiviral agents which inactivate viral or host cell factors which are essential for viral replication.

HCV is an enveloped positive strand RNA virus in the genus *Hepacivirus* in the Flaviviridae family. The single strand HCV RNA genome is approximately 9500 nucleotides in length and has a single open reading frame (ORF), flanked by 5' and 3' non-translated regions The HCV 5' non-translated region is 341 nucleotides in length and functions as an internal ribosome entry site for cap-independent translation initiation. The open reading frame encodes a single large polyprotein of about 3000 amino acids which is cleaved at multiple sites by cellular and viral proteases to produce the mature structural and non-structural (NS2, NS3, NS4A, NS4B, NS5A, and NS5B) proteins. The viral NS2/3 protease cleaves at the NS2-NS3 junction; while the viral NS3 protease mediates the cleavages downstream of NS3, at the NS3-NS4A, NS4A-NS4B, NS4B-NS5A and NS5A-NS5B cleavage sites. The NS3 protein also exhibits nucleoside triphosphatase and RNA helicase activities. The NS4A protein acts as a cofactor for the NS3 protease and may also assist in the membrane localization of NS3 and other viral replicase components. Although NS4B and the NS5A phosphoprotein are also likely components of the replicase, their specific roles are unknown. The NS5B protein is the elongation subunit of the HCV replicase possessing RNA-dependent RNA polymerase (RdRp) activity.

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics. It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

SUMMARY OF THE INVENTION

The present invention provides a novel series of compounds having inhibitory activity against HCV polymerase. In particular compounds according to this invention inhibit RNA synthesis by the RNA dependent RNA polymerase of HCV, especially the enzyme NS5B encoded by HCV. A further advantage of compounds provided by this invention is their low to very low or even non-significant activity against other polymerases. Further objects of this invention arise for the one skilled in the art from the following description and the examples.

One aspect of the invention provides compounds of formula (I):

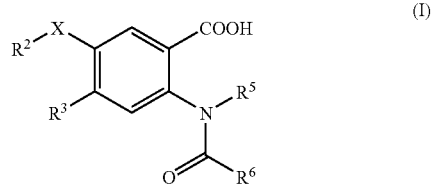

wherein:

X is selected from O and S;

$R^2$ is aryl, optionally substituted with $R^{20}$, wherein $R^{20}$ is 1 to 5 substituents each independently selected from:
  a) halo, $(C_{1-6})$alkyl, $(C_{1-6})$haloalkyl, $(C_{3-7})$cycloalkyl, or $(C_{3-7})$cycloalkyl-$(C_{1-6})$alkyl-;
  b) —N($R^7$)$R^8$ or —Y—N($R^7$)$R^8$ wherein
    Y is selected from —C(=O)—, —SO$_2$— and —$(C_{1-6})$alkylene-;
    $R^7$ is in each instance independently selected from H and $(C_{1-6})$alkyl; and
    $R^8$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)O$R^9$ and —C(=O)NH$R^9$;
    wherein the $(C_{1-6})$alkyl is optionally substituted with —OH, —O—$(C_{1-6})$alkyl, cyano, —NH$_2$, —NH$(C_{1-4})$alkyl or —N(($C_{1-4})$alkyl)$_2$; and
    wherein each of the aryl and Het is optionally substituted with 1 to 3 substituents each independently selected from
      i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N(($C_{1-4})$alkyl)$_2$, —NH$_2$, —NH$(C_{1-4})$alkyl, —N(($C_{1-4})$alkyl)$_2$ or —NH—C(=O)$(C_{1-4})$alkyl;
      ii) $(C_{1-6})$alkyl optionally substituted with —OH or —O—$(C_{1-6})$alkyl; and
      iii) aryl or Het, wherein each of the aryl and Het is optionally substituted with halo or $(C_{1-6})$alkyl; and
    wherein $R^9$ is selected from:
      i) $(C_{1-6})$alkyl optionally substituted with —COOH, —NH$_2$, —NH$(C_{1-4})$alkyl or —N(($C_{1-4})$alkyl)$_2$; and
      ii) Het optionally substituted with $(C_{1-6})$alkyl; or
    $R^7$ and $R^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:

i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl;

c) aryl, aryl-$(C_{1-6})$alkyl-, Het or Het-$(C_{1-6})$alkyl-, wherein each of the aryl, aryl-$(C_{1-6})$alkyl-, Het and Het-$(C_{1-6})$alkyl- is optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and d) —C(=O)—$R^{10}$, —O—$R^{10}$, —C(=O)—O—$R^{10}$, —$(C_{1-6})$alkylene-O—$R^{10}$, —S—$R^{10}$, —SO—$R^{10}$, —SO$_2$—$R^{10}$, —$(C_{1-6})$alkylene-S—$R^{10}$, —$(C_{1-6})$alkylene-SO—$R^{10}$ or —$(C_{1-6})$alkylene-SO$_2$—$R_{10}$ wherein $R^{10}$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl and Het;

wherein the $(C_{1-6})$alkyl is optionally substituted with —OH, —O—$(C_{1-6})$alkyl, cyano, —NH$_2$, —NH$(C_{1-4})$alkyl or —N$((C_{1-4})$alkyl$)_2$; and wherein each of the aryl and Het is optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl;

provided that when X is O, $R^2$ is not a group of the formula

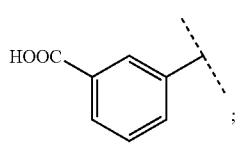

$R^3$ is selected from H, halo, $(C_{1-4})$alkyl, —O—$(C_{1-4})$alkyl, —S—$(C_{1-4})$alkyl, —NH$_2$, —NH$(C_{1-4})$alkyl and —N$((C_{1-4})$alkyl$)_2$;

$R^5$ is selected from H, $(C_{1-6})$alkyl, $(C_{3-7})$cycloalkyl, $(C_{3-7})$cycloalkyl-$(C_{1-3})$alkyl- and Het; the $(C_{1-6})$alkyl and Het each being optionally substituted with 1 to 4 substituents each independently selected from $(C_{1-6})$alkyl, —OH, —COOH, —C(=O)—$(C_{1-6})$alkyl, —C(=O)—O—$(C_{1-6})$alkyl, —C(=O)—NH—$(C_{1-6})$alkyl, —C(=O)—N$((C_{1-6})$alkyl$)_2$, and —SO$_2$$(C_{1-6})$alkyl; and $R^6$ is selected from $(C_{5-7})$cycloalkyl, $(C_{5-7})$cycloalkyl-$(C_{1-3})$alkyl-, aryl and aryl-$(C_{1-3})$alkyl; the $(C_{5-7})$cycloalkyl, $(C_{5-7})$cycloalkyl-$(C_{1-3})$alkyl-, aryl and aryl-$(C_{1-3})$alkyl each being optionally substituted with 1 to 5 substituents each independently selected from halo, $(C_{1-6})$alkyl, $(C_{1-6})$haloalkyl, —OH, —SH, —O—$(C_{1-4})$alkyl and —S—$(C_{1-4})$alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S; or a salt or ester thereof.

Another aspect of this invention provides a compound of formula (I), or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of a hepatitis C viral infection in a mammal having or at risk of having the infection.

A further aspect of the invention involves a method of treating a hepatitis C viral infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating a hepatitis C viral infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of a hepatitis C viral infection in a mammal having or at risk of having the infection.

Another aspect of this invention provides the use of a compound of formula (I) as described herein, or a pharmaceutically acceptable salt or ester thereof, for the manufacture of a medicament for the treatment of a hepatitis C viral infection in a mammal having or at risk of having the infection.

An additional aspect of this invention refers to an article of manufacture comprising a composition effective to treat a hepatitis C viral infection; and packaging material comprising a label which indicates that the composition can be used to treat infection by the hepatitis C virus; wherein the composition comprises a compound of formula (I) according to this invention or a pharmaceutically acceptable salt or ester thereof.

Still another aspect of this invention relates to a method of inhibiting the replication of hepatitis C virus comprising exposing the virus to an effective amount of the compound of formula (I), or a salt or ester thereof, under conditions where replication of hepatitis C virus is inhibited.

Further included in the scope of the invention is the use of a compound of formula (I), or a salt or ester thereof, to inhibit the replication of hepatitis C virus.

DETAILED DESCRIPTION OF THE INVENTION

Definitions

As used herein, the following definitions apply unless otherwise noted:

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl (n-propyl), butyl (n-butyl), 1-methylethyl (iso-propyl), 1-methylpropyl (sec-butyl), 2-methylpropyl (iso-butyl), 1,1-dimethylethyl (tert-butyl), pentyl and hexyl. The abbreviation Me denotes a methyl group; Et denotes an ethyl group, Pr denotes a propyl group, iPr denotes a 1-methylethyl group, Bu denotes a butyl group and tBu denotes a 1,1-dimethylethyl group.

The term "$(C_{1-n})$alkylene" as used herein, wherein n is an integer, either alone or in combination with another radical, is intended to mean acyclic, straight or branched chain divalent alkyl radicals containing from 1 to n carbon atoms. "$(C_{1-6})$alkylene" includes, but is not limited to, —$CH_2$—, —$CH_2CH_2$—,

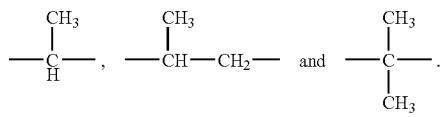

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$cycloalkyl-$(C_{1-6})$alkyl-include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl (benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise.

The term "Het" as used herein, either alone or in combination with another radical, is intended to mean a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S, unless specified otherwise. When a Het group is substituted, it is understood that substituents may be attached to any carbon atom or heteroatom thereof which would otherwise bear a hydrogen atom, unless specified otherwise.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise.

The term "heteroatom" as used herein is intended to mean O, S or N.

The term "heterocycle" as used herein and unless specified otherwise, either alone or in combination with another radical, is intended to mean a 4- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine, and saturated, unsaturated and aromatic derivatives thereof.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, isoindole, benzimidazole, benzothiophene, benzofuran, benzodioxole, benzothiazole, quinoline, isoquinoline, and naphthyridine.

The term "halo" as used herein is intended to mean a halogen substituent selected from fluoro, chloro, bromo or iodo.

The term "($C_{1-n}$)haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of ($C_{1-n}$)haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—($C_{1-n}$)alkyl" or "($C_{1-n}$)alkoxy" as used herein interchangeably, wherein n is an integer, either alone or in combination with another radical, is intended to mean an oxygen atom further bonded to an alkyl radical having 1 to n carbon atoms as defined above. Examples of —O—($C_{1-n}$)alkyl include but are not limited to methoxy ($CH_3O$—), ethoxy ($CH_3CH_2O$—), propoxy ($CH_3CH_2CH_2$)—), 1-methylethoxy (iso-propoxy; $(CH_3)_2CH$—O—) and 1,1-dimethylethoxy (tert-butoxy; $(CH_3)_3C$—O—). When an —O—($C_{1-n}$)alkyl radical is substituted, it is understood to be substituted on the ($C_{1-n}$)alkyl portion thereof.

The terms "—S—($C_{1-n}$)alkyl" or "($C_{1-n}$)alkylthio" as used herein interchangeably, wherein n is an integer, either alone or in combination with another radical, is intended to mean an sulfur atom further bonded to an alkyl radical having 1 to n carbon atoms as defined above. Examples of —S—($C_{1-n}$)alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—($C_{1-n}$)alkyl radical, or an oxidized derivative thereof, such as an —SO—($C_{1-n}$)alkyl radical or an —$SO_2$—($C_{1-n}$)alkyl radical, is substituted, each is understood to be substituted on the ($C_{1-n}$)alkyl portion thereof.

The term "oxo" as used herein is intended to mean an oxygen atom attached to a carbon atom as a substituent by a double bond (=O).

The term "thioxo" as used herein is intended to mean an sulfur atom attached to a carbon atom as a substituent by a double bond (=S).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

The following designation

is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COOH substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituent, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halogen, $(C_{1-4})$alkyl or $(C_{1-4})$alkoxy. Other suitable esters can be found in Design of Prodrugs, Bundgaard, H. Ed. Elsevier (1985). Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "mammal" as used herein is intended to encompass humans, as well as non-human mammals which are susceptible to infection by hepatitis C virus. Non-human mammals include but are not limited to domestic animals, such as cows, pigs, horses, dogs, cats, rabbits, rats and mice, and non-domestic animals.

The term "treatment" as used herein is intended to mean the administration of a compound or composition according to the present invention to alleviate or eliminate symptoms of the hepatitis C disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

The term "antiviral agent" as used herein is intended to mean an agent that is effective to inhibit the formation and/or replication of a virus in a mammal, including but not limited to agents that interfere with either host or viral mechanisms necessary for the formation and/or replication of a virus in a mammal.

Preferred Embodiments

In the following preferred embodiments, groups and substituents of the compounds according to this invention are described in detail.

X:

X-A: In one embodiment, X is O.

X-B: In another embodiment, X is S.

Any and each individual definition of X as set out herein may be combined with any and each individual definition of $R^2$, $R^3$, $R^5$ and $R^6$ as set out herein.

$R^2$:

$R^2$-A: In one embodiment, $R^2$ is naphthyl or phenyl, the phenyl being optionally substituted with $R^{20}$ wherein $R^{20}$ is defined as embodiment $R^{20}$-A;

provided that when X is O, $R^2$ is not a group of the formula

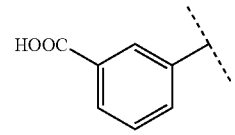

$R^{20}$-A In this embodiment, $R^{20}$ is 1 to 5 substituents each independently selected from:
a) halo, $(C_{1-6})$alkyl, $(C_{1-6})$haloalkyl, $(C_{3-7})$cycloalkyl, or $(C_{3-7})$cycloalkyl-$(C_{1-6})$alkyl-;
b) —N$(R^7)R^8$ or —Y—N$(R^7)R^8$ wherein
  Y is selected from —C(=O)—, —SO$_2$— and —$(C_{1-6})$alkylene-;
  $R^7$ is in each instance independently selected from H and $(C_{1-6})$alkyl; and
  $R^8$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)O$R^9$ and —C(=O)NH$R^9$;
  wherein the $(C_{1-6})$alkyl is optionally substituted with —OH, —O—$(C_{1-6})$alkyl, cyano, —NH$_2$, —NH$(C_{1-4})$alkyl or —N$((C_{1-4})$alkyl$)_2$; and
  wherein each of the aryl and Het is optionally substituted with 1 to 3 substituents each independently selected from
    i) halo, —OH, $(C_{1-6})$haloalkyl, —C(=O)—$(C_{1-6})$alkyl, —SO$_2(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl; and
  wherein $R^9$ is selected from:
    i) $(C_{1-6})$alkyl optionally substituted with —COOH, —NH$_2$, —NH$(C_{1-4})$alkyl or —N$((C_{1-4})$alkyl$)_2$; and
    ii) Het optionally substituted with $(C_{1-6})$alkyl; or
  $R^7$ and $R^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:
    i) halo, —OH, $(C_{1-6})$haloalkyl, —C(=O)—$(C_{1-6})$alkyl, —SO$_2(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl;

c) aryl, aryl-($C_{1-6}$)alkyl-, Het or Het-($C_{1-6}$)alkyl-, wherein each of the aryl, aryl-($C_{1-6}$)alkyl-, Het and Het-($C_{1-6}$)alkyl- is optionally substituted with 1 to 3 substituents each independently selected from
  i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
  ii) ($C_{1-6}$)alkyl optionally substituted with —OH or —O—($C_{1-6}$)alkyl; and
  iii) aryl or Het, wherein each of the aryl and Het is optionally substituted with halo or ($C_{1-6}$)alkyl; and
d) —C(=O)—$R^{10}$, —O—$R^{10}$, —C(=O)—O—$R^{10}$, —($C_{1-6}$)alkylene-O—$R^{10}$, —S—$R^{10}$, —SO—$R^{10}$, —SO$_2$—$R^{10}$, —($C_{1-6}$)alkylene-S—$R^{10}$, —($C_{1-6}$)alkylene-SO—$R^{10}$ or —($C_{1-6}$)alkylene-SO$_2$—$R^{10}$ wherein
  $R^{10}$ is in each instance independently selected from H, ($C_{1-6}$)alkyl, ($C_{1-6}$)haloalkyl, ($C_{3-7}$)cycloalkyl, ($C_{3-7}$)cycloalkyl-($C_{1-6}$)alkyl-, aryl and Het;
  wherein the ($C_{1-6}$)alkyl is optionally substituted with —OH, —O—($C_{1-6}$)alkyl, cyano, —NH$_2$, —NH($C_{1-4}$)alkyl or —N(($C_{1-4}$)alkyl)$_2$; and
  wherein each of the aryl and Het is optionally substituted with 1 to 3 substituents each independently selected from
    i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
    ii) ($C_{1-6}$)alkyl optionally substituted with —OH or —O—($C_{1-6}$)alkyl; and
    iii) aryl or Het, wherein each of the aryl and Het is optionally substituted with halo or ($C_{1-6}$)alkyl.

$R^2$-B: In another embodiment, $R^2$ is naphthyl or phenyl, the phenyl being optionally substituted with $R^{20}$ wherein $R^{20}$ is defined as embodiment $R^{20}$-B;

provided that when X is O, $R^2$ is not a group of the formula

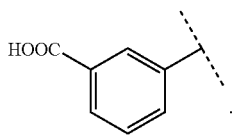

$R^{20}$-B: In this embodiment, $R^{20}$ is 1 to 5 substituents each independently selected from:
a) halo, ($C_{1-6}$)alkyl or ($C_{1-6}$)haloalkyl;
b) —N($R^7$)$R^8$ or —Y—N($R^7$)$R^8$ wherein
  Y is selected from —C(=O)—, —SO$_2$— and —($C_{1-6}$)alkylene-;
  $R^7$ is in each instance selected from H and ($C_{1-6}$)alkyl; and
  $R^8$ is in each instance independently selected from H, ($C_{1-6}$)alkyl, ($C_{1-6}$)haloalkyl, ($C_{3-7}$)cycloalkyl, ($C_{3-7}$)cycloalkyl-($C_{1-6}$)alkyl-, aryl, Het, —C(=O)—$R^9$, —C(=O)OR$^9$ and —C(=O)NHR$^9$;
  wherein the ($C_{1-6}$)alkyl is optionally substituted with —OH, —O—($C_{1-6}$)alkyl, cyano, —NH$_2$, —NH($C_{1-4}$)alkyl or —N(($C_{1-4}$)alkyl)$_2$; and
  wherein each of the aryl and Het is optionally substituted with 1 to 3 substituents each independently selected from
    i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
    ii) ($C_{1-6}$)alkyl optionally substituted with —OH or —O—($C_{1-6}$)alkyl; and
    iii) aryl or Het, wherein each of the aryl and Het is optionally substituted with halo or ($C_{1-6}$)alkyl; and
  wherein $R^9$ is selected from:
    i) ($C_{1-6}$)alkyl optionally substituted with —COOH, —NH$_2$, —NH($C_{1-4}$)alkyl or —N(($C_{1-4}$)alkyl)$_2$; and
    ii) Het optionally substituted with ($C_{1-6}$)alkyl; or
  $R^7$ and $R^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:
    i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
    ii) ($C_{1-6}$)alkyl optionally substituted with —OH or —O—($C_{1-6}$)alkyl; and
    iii) aryl or Het, wherein each of the aryl and Het is optionally substituted with halo or ($C_{1-6}$)alkyl;
c) aryl, Het or Het-($C_{1-6}$)alkyl-, wherein each of the aryl, Het and Het-($C_{1-6}$)alkyl-, is optionally substituted with 1 to 3 substituents each independently selected from
  i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
  ii) ($C_{1-6}$)alkyl optionally substituted with —OH or —O—($C_{1-6}$)alkyl; and
  iii) aryl or Het, wherein each of the aryl and Het is optionally substituted with halo or ($C_{1-6}$)alkyl; and
d) —C(=O)—$R^{10}$, —O—$R^{10}$, —C(=O)—O—$R^{10}$ or —($C_{1-6}$)alkylene-O—$R^{10}$ wherein
  $R^{10}$ is in each instance independently selected from H, ($C_{1-6}$)alkyl, ($C_{1-6}$)haloalkyl, ($C_{3-7}$)cycloalkyl, ($C_{3-7}$)cycloalkyl-($C_{1-6}$)alkyl-, aryl and Het;
  wherein the ($C_{1-6}$)alkyl is optionally substituted with —OH, —O—($C_{1-6}$)alkyl, cyano, —NH$_2$, —NH($C_{1-4}$)alkyl or —N(($C_{1-4}$)alkyl)$_2$; and
  wherein each of the aryl and Het is optionally substituted with 1 to 3 substituents each independently selected from
    i) halo, —OH, ($C_{1-6}$)haloalkyl, —C(=O)—($C_{1-6}$)alkyl, —SO$_2$($C_{1-6}$)alkyl, —C(=O)—NH$_2$, —C(=O)—NH($C_{1-4}$)alkyl, —C(=O)—N(($C_{1-4}$)alkyl)$_2$, —NH$_2$, —NH($C_{1-4}$)alkyl, —N(($C_{1-4}$)alkyl)$_2$ or —NH—C(=O)($C_{1-4}$)alkyl;
    ii) ($C_{1-6}$)alkyl optionally substituted with —OH or —O—($C_{1-6}$)alkyl; and
    iii) aryl or Het, wherein each of the aryl and Het is optionally substituted with halo or ($C_{1-6}$)alkyl.

$R^2$-C: In yet another embodiment, $R^2$ is phenyl optionally substituted with $R^{20}$ wherein $R^{20}$ is defined as embodiment $R^{20}$-A hereinabove;

provided that when X is O, $R^2$ is not a group of the formula

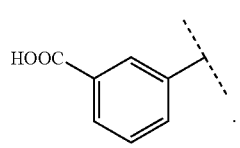

R²-D: In still another embodiment, R² is phenyl optionally substituted with R²⁰ wherein R²⁰ is defined as embodiment R²⁰-B hereinabove;
provided that when X is O, R² is not a group of the formula

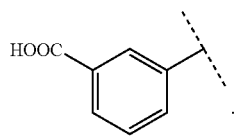

In an alternative embodiment, R² is a group of formula:

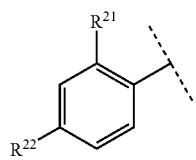

wherein
R²¹ and R²² are as defined below.
R²¹-A: In this embodiment, R²¹ is selected from H, halo, $(C_{1-6})$alkyl, $(C_{1-6})$haloalkyl and —O—$(C_{1-6})$haloalkyl.
R²¹-B: In this embodiment, R²¹ is selected from H, Cl, Br, CH₃, CF₃ and —OCF₃.
R²¹-C: In this embodiment, R²¹ is H or CF₃.
R²¹-D: In this embodiment, R²¹ is CF₃.
R²²-A: In this embodiment, R²² is selected from H, halo, $(C_{1-3})$alkyl, $(C_{1-3})$haloalkyl, —$(C_{1-3})$alkylene-OH, —C(=O)—$(C_{1-3})$alkyl and —COOH.
R²²-B: In this embodiment, R²² is selected from H, halo, $(C_{1-3})$alkyl, —$(C_{1-3})$alkylene-OH, —C(=O)—$(C_{1-3})$alkyl and —COOH.
R²²-C: In this embodiment, R²² is selected from H, F, I, —CH₂OH, CF₃, —C(=O)CH₃ and —COOH.
R²²-D: In this embodiment, R²² is selected from:
  b) —N(R⁷)R⁸ or —Y—N(R⁷)R⁸ wherein
    Y is selected from —C(=O)—, —SO₂— and —$(C_{1-6})$alkylene-;
    R⁷ is selected from H and $(C_{1-6})$alkyl; and
    R⁸ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—R⁹, —C(=O)OR⁹ and —C(=O)NHR⁹;
    wherein the $(C_{1-6})$alkyl is optionally substituted with —OH, —O—$(C_{1-6})$alkyl, cyano, —NH₂, —NH$(C_{1-4})$alkyl or —N($(C_{1-4})$alkyl)₂; and
    wherein each of the aryl and Het is optionally substituted with 1 to 3 substituents each independently selected from
    i) halo, —OH, $(C_{1-6})$haloalkyl, —C(=O)—$(C_{1-6})$alkyl, —SO₂$(C_{1-6})$alkyl, —C(=O)—NH₂, —C(=O)—NH$(C_{1-4})$alkyl, —C(=O)—N($(C_{1-4})$alkyl)₂, —NH₂, —NH$(C_{1-4})$alkyl, —N($(C_{1-4})$alkyl)₂ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl; and
    wherein R⁹ is selected from:
    i) $(C_{1-6})$alkyl optionally substituted with —COOH, —NH₂, —NH$(C_{1-4})$alkyl or —N($(C_{1-4})$alkyl)₂; and
    ii) Het optionally substituted with $(C_{1-6})$alkyl; or
    R⁷ and R⁸ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:
    i) halo, —OH, $(C_{1-6})$haloalkyl, —C(=O)—$(C_{1-6})$alkyl, —SO₂$(C_{1-6})$alkyl, —C(=O)—NH₂, —C(=O)—NH$(C_{1-4})$alkyl, —C(=O)—N($(C_{1-4})$alkyl)₂, —NH₂, —NH$(C_{1-4})$alkyl, —N($(C_{1-4})$alkyl)₂ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl; and
  c) aryl, Het or Het-$(C_{1-6})$alkyl-, wherein each of the aryl, Het and Het-$(C_{1-6})$alkyl-, is optionally substituted with 1 to 3 substituents each independently selected from
    i) halo, —OH, $(C_{1-6})$haloalkyl, —C(=O)—$(C_{1-6})$alkyl, —SO₂$(C_{1-6})$alkyl, —C(=O)—NH₂, —C(=O)—NH$(C_{1-4})$alkyl, —C(=O)—N($(C_{1-4})$alkyl)₂, —NH₂, —NH$(C_{1-4})$alkyl, —N($(C_{1-4})$alkyl)₂ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl.
R²²-E: In this embodiment, R²² is selected from:
  b) —N(R⁷)R⁸ wherein
    R⁷ is selected from H and $(C_{1-6})$alkyl; and
    R⁸ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—R⁹, —C(=O)OR⁹ and —C(=O)NHR⁹;
    wherein the $(C_{1-6})$alkyl is optionally substituted with —OH, —O—$(C_{1-6})$alkyl, cyano, —NH₂, —NH$(C_{1-4})$alkyl or —N($(C_{1-4})$alkyl)₂; and
    wherein each of the aryl and Het is optionally substituted with 1 to 3 substituents each independently selected from
    i) halo, —OH, $(C_{1-6})$haloalkyl, —C(=O)—$(C_{1-6})$alkyl, —SO₂$(C_{1-6})$alkyl, —C(=O)—NH₂, —C(=O)—NH$(C_{1-4})$alkyl, —C(=O)—N($(C_{1-4})$alkyl)₂, —NH₂, —NH$(C_{1-4})$alkyl, —N($(C_{1-4})$alkyl)₂ or —NH—C(=O)$(C_{1-4})$alkyl;
    ii) $(C_{1-6})$alkyl optionally substituted with —OH or —O—$(C_{1-6})$alkyl; and
    iii) aryl or Het, wherein each of the aryl and Het is optionally substituted with halo or $(C_{1-6})$alkyl; and
    wherein R⁹ is selected from:
    i) $(C_{1-6})$alkyl optionally substituted with —COOH, —NH₂, —NH$(C_{1-4})$alkyl or —N($(C_{1-4})$alkyl)₂; and
    ii) Het optionally substituted with $(C_{1-6})$alkyl; or
    R⁷ and R⁸ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:

i) halo, —OH, (C$_{1-6}$)haloalkyl, —C(═O)—(C$_{1-6}$)alkyl, —SO$_2$(C$_{1-6}$)alkyl, —C(═O)—NH$_2$, —C(═O)—NH(C$_{1-4}$)alkyl, —C(═O)—N((C$_{1-4}$)alkyl)$_2$, —NH$_2$, —NH(C$_{1-4}$)alkyl, —N((C$_{1-4}$)alkyl)$_2$ or —NH—C(═O)(C$_{1-4}$)alkyl;
ii) (C$_{1-6}$)alkyl optionally substituted with —OH or —O—(C$_{1-6}$)alkyl; and
iii) aryl or Het, wherein each of the aryl and Het is optionally substituted with halo or (C$_{1-6}$)alkyl; and
c) Het optionally substituted with 1 to 3 substituents each independently selected from
i) halo, —OH, (C$_{1-6}$)haloalkyl, —C(═O)—(C$_{1-6}$)alkyl, —SO$_2$(C$_{1-6}$)alkyl, —C(═O)—NH$_2$, —C(═O)—NH(C$_{1-4}$)alkyl, —C(═O)—N((C$_{1-4}$)alkyl)$_2$, —NH$_2$, —NH(C$_{1-4}$)alkyl, —N((C$_{1-4}$)alkyl)$_2$ or —NH—C(═O)(C$_{1-4}$)alkyl;
ii) (C$_{1-6}$)alkyl optionally substituted with —OH or —O—(C$_{1-6}$)alkyl; and
iii) aryl or Het, wherein each of the aryl and Het is optionally substituted with halo or (C$_{1-6}$)alkyl.

$R^{22}$-F: In this embodiment, $R^{22}$ is selected from:
b) —N($R^7$)$R^8$ wherein
$R^7$ is selected from H, methyl and ethyl; and
$R^8$ is selected from H, (C$_{1-3}$)alkyl, —C(═O)—$R^9$, —C(═O)O$R^9$ and —C(═O)NH$R^9$; the (C$_{1-3}$)alkyl being optionally substituted with —OCH$_3$;
wherein $R^9$ is selected from:
i) (C$_{1-4}$)alkyl optionally substituted with —COOH or —N(CH$_3$)$_2$; and
ii) a 5- or 6-membered heterocycle containing 1 to 3 heteroatoms each independently selected from N, O and S, the heterocycle being optionally substituted with (C$_{1-3}$)alkyl; or
$R^7$ and $R^8$ are linked together with the N to which they are attached to form a 5-, 6- or 7-membered heterocycle optionally containing 1 or 2 additional heteroatoms each independently selected from N, O and S, or a 9- or 10-membered heteropolycycle optionally containing 1 or 2 additional heteroatoms each independently selected from N, O and S; the heterocycle and heteropolycycle each being optionally substituted with 1 to 3 substituents each independently selected from:
i) —OH, —CF$_3$, —C(═O)—(C$_{1-3}$)alkyl, —SO$_2$(C$_{1-3}$)alkyl, —C(═O)—NH$_2$, —C(═O)—NH(C$_{1-3}$)alkyl, —C(═O)—N((C$_{1-3}$)alkyl)$_2$, —NH$_2$, —NH(C$_{1-3}$)alkyl, —N((C$_{1-3}$)alkyl)$_2$ or —NH—C(═O)(C$_{1-3}$)alkyl;
ii) (C$_{1-3}$)alkyl optionally substituted with —OH or —O—(C$_{1-3}$)alkyl; and
iii) a 5- or 6-membered heterocycle containing 1 to 3 heteroatoms each independently selected from N, O and S or phenyl, wherein the phenyl is optionally substituted with fluoro; and
c) Het wherein the Het is a 5-, 6- or 7-membered heterocycle optionally containing 1 or 2 additional heteroatoms each independently selected from N, O and S, or a 9- or 10-membered heteropolycycle optionally containing 1 or 2 additional heteroatoms each independently selected from N, O and S; and wherein the Het is optionally substituted with 1 to 3 substituents each independently selected from
i) —OH, —CF$_3$, —C(═O)—(C$_{1-3}$)alkyl, —SO$_2$(C$_{1-3}$)alkyl, —C(═O)—NH$_2$, —C(═O)—NH(C$_{1-3}$)alkyl, —C(═O)—N((C$_{1-3}$)alkyl)$_2$, —NH$_2$, —NH(C$_{1-3}$)alkyl, —N((C$_{1-3}$)alkyl)$_2$ or —NH—C(═O)(C$_{1-3}$)alkyl;
ii) (C$_{1-3}$)alkyl optionally substituted with —OH or —O—(C$_{1-3}$)alkyl; and
iii) a 5- or 6-membered heterocycle containing 1 to 3 heteroatoms each independently selected from N, O and S or phenyl,
wherein the phenyl is optionally substituted with fluoro.

$R^{22}$-G: In this embodiment, $R^{22}$ is selected from:
b) —N($R^7$)$R^8$ wherein
$R^7$ is selected from H, methyl and ethyl; and
$R^8$ is selected from H, methyl, ethyl, —CH$_2$CH$_2$—OCH$_3$, —C(═O)—CH$_3$, —C(═O)—CH$_2$CH$_2$COOH, —C(═O)OC(CH$_3$)$_3$, —C(═O)NHCH$_2$CH$_2$N(CH$_3$)$_2$, and

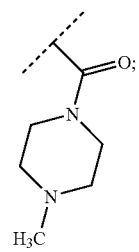

or
$R^7$ and $R^8$ are linked together with the N to which they are attached to form a heterocycle selected from:

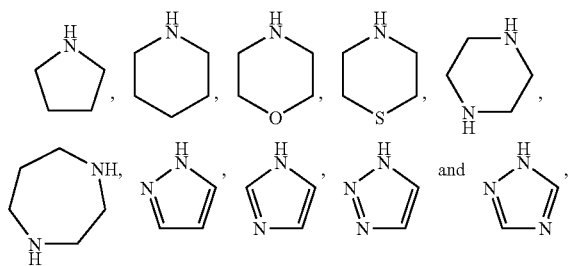

or a heteropolycycle selected from:

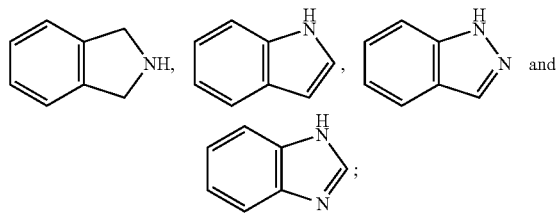

the heterocycle and heteropolycycle each being optionally substituted with 1 to 3 substituents each independently selected from:
CH$_3$, CH$_2$CH$_3$, —CH$_2$OH, —CH$_2$CH$_2$OH, —CH$_2$OCH$_3$, —OH, —CF$_3$, —C(═O)—CH$_3$, —SO$_2$CH$_3$, —C(═O)—NH$_2$, —C(═O)—N(CH$_2$CH$_3$)$_2$, —NH$_2$, —N(CH$_3$)$_2$, —NH—C(═O)CH$_3$,

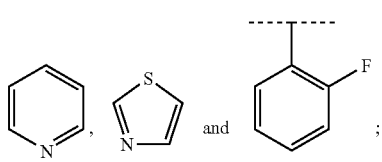

and c) Het wherein the Het is selected from:

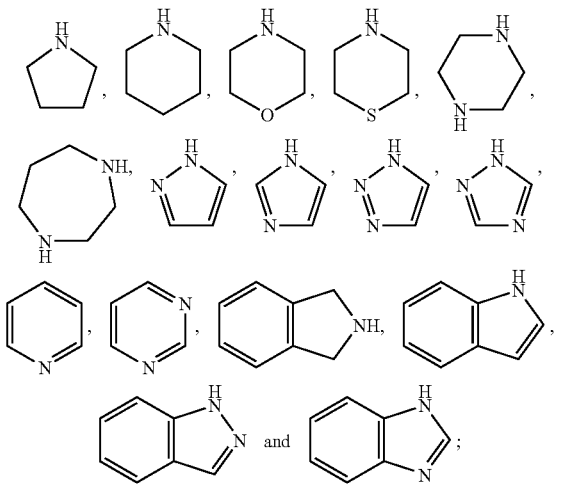

and wherein the Het is optionally substituted with 1 to 3 substituents each independently selected from: $CH_3$, $CH_2CH_3$, $-CH_2OH$, $-CH_2CH_2OH$, $-CH_2OCH_3$, $-OH$, $-CF_3$, $-C(=O)-CH_3$, $-SO_2CH_3$, $-C(=O)-NH_2$, $-C(=O)-N(CH_2CH_3)_2$, $-NH_2$, $-N(CH_3)_2$, $-NH-C(=O)CH_3$,

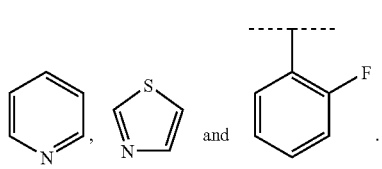

$R^{22}$-H: In this embodiment, $R^{22}$ is selected from
b) $-Y-N(R^7)R^8$ wherein
  Y is selected from $-C(=O)-$, $-SO_2-$ and $-CH_2-$;
  $R^7$ is selected from H and $(C_{1-6})$alkyl; and
  $R^8$ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, $-C(=O)-R^9$, $-C(=O)OR^9$ and $-C(=O)NHR^9$;
  wherein the $(C_{1-6})$alkyl is optionally substituted with $-OH$, $-O-(C_{1-6})$alkyl, cyano, $-NH_2$, $-NH(C_{1-4})$alkyl or $-N((C_{1-4})$alkyl$)_2$; and
  wherein each of the aryl and Het is optionally substituted with 1 to 3 substituents each independently selected from
  i) halo, $-OH$, $(C_{1-6})$haloalkyl, $-C(=O)-(C_{1-6})$alkyl, $-SO_2(C_{1-6})$alkyl, $-C(=O)-NH_2$, $-C(=O)-NH(C_{1-4})$alkyl, $-C(=O)-N((C_{1-4})$alkyl$)_2$, $-NH_2$, $-NH(C_{1-4})$alkyl, $-N((C_{1-4})$alkyl$)_2$ or $-NH-C(=O)(C_{1-4})$alkyl;
  ii) $(C_{1-6})$alkyl optionally substituted with $-OH$ or $-O-(C_{1-6})$alkyl; and
  iii) aryl or Het, wherein each of the aryl and Het is optionally substituted with halo or $(C_{1-6})$alkyl; and
  wherein $R^9$ is selected from:
  i) $(C_{1-6})$alkyl optionally substituted with $-COOH$, $-NH_2$, $-NH(C_{1-4})$alkyl or $-N((C_{1-4})$alkyl$)_2$; and
  ii) Het optionally substituted with $(C_{1-6})$alkyl; or
  $R^7$ and $R^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:
  i) halo, $-OH$, $(C_{1-6})$haloalkyl, $-C(=O)-(C_{1-6})$alkyl, $-SO_2(C_{1-6})$alkyl, $-C(=O)-NH_2$, $-C(=O)-NH(C_{1-4})$alkyl, $-C(=O)-N((C_{1-4})$alkyl$)_2$, $-NH_2$, $-NH(C_{1-4})$alkyl, $-N((C_{1-4})$alkyl$)_2$ or $-NH-C(=O)(C_{1-4})$alkyl;
  ii) $(C_{1-6})$alkyl optionally substituted with $-OH$ or $-O-(C_{1-6})$alkyl; and
  iii) aryl or Het, wherein each of the aryl and Het is optionally substituted with halo or $(C_{1-6})$alkyl; and
c) Het-$(C_{1-6})$alkyl-, optionally substituted with 1 to 3 substituents each independently selected from
  i) halo, $-OH$, $(C_{1-6})$haloalkyl, $-C(=O)-(C_{1-6})$alkyl, $-SO_2(C_{1-6})$alkyl, $-C(=O)-NH_2$, $-C(=O)-NH(C_{1-4})$alkyl, $-C(=O)-N((C_{1-4})$alkyl$)_2$, $-NH_2$, $-NH(C_{1-4})$alkyl, $-N((C_{1-4})$alkyl$)_2$ or $-NH-C(=O)(C_{1-4})$alkyl;
  ii) $(C_{1-6})$alkyl optionally substituted with $-OH$ or $-O-(C_{1-6})$alkyl; and
  iii) aryl or Het, wherein each of the aryl and Het is optionally substituted with halo or $(C_{1-6})$alkyl.

$R^{22}$-I: In this embodiment, $R^{22}$ is $-Y-N(R^7)R^8$ wherein
  Y is selected from $-C(=O)-$ and $-SO_2-$;
  $R^7$ is selected from H and methyl; and
  $R^8$ is selected from H, $(C_{1-6})$alkyl, $(C_{1-6})$haloalkyl, $(C_{3-7})$cycloalkyl, $(C_{3-7})$cycloalkyl-$(C_{1-6})$alkyl- and a 5- or 6-membered heterocycle containing 1 to 3 heteroatoms each independently selected from N, O and S;
  wherein the $(C_{1-6})$alkyl is optionally substituted with $-OH$, $-O-(C_{1-3})$alkyl, cyano or $-N((C_{1-3})$alkyl$)_2$; or
  $R^7$ and $R^8$ are linked together with the N to which they are attached to form a 5- or 6-membered heterocycle optionally containing 1 to 3 additional heteroatoms each independently selected from N, O and S; the heterocycle being optionally substituted with 1 to 3 substituents each independently selected from $-OH$ and $N((C_{1-3})$alkyl$)_2$.

$R^{22}$-J: In this embodiment, $R^{22}$ is $-Y-N(R^7)R^8$ wherein
  Y is selected from $-C(=O)-$ and $-SO_2-$;
  $R^7$ is selected from H and methyl; and
  $R^8$ is selected from H, $(C_{1-4})$alkyl, $-CH_2CF_3$, $(C_{3-5})$cycloalkyl, cyclopropylmethyl,

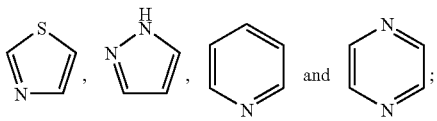

wherein the $(C_{1-4})$alkyl is optionally substituted with —OH, —OCH$_3$, —OCH$_2$CH$_3$, cyano or —N(CH$_3$)$_2$; or R$^7$ and R$^8$ are linked together with the N to which they are attached to form a heterocycle selected from

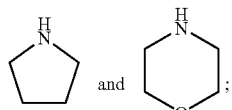

the heterocycle being optionally substituted with 1 to 3 substituents each independently selected from —OH and N(CH$_3$)$_2$.

R$^{22}$-K: In this embodiment, R$^{22}$ is selected from
b) —CH$_2$—N(R$^7$)R$^8$ wherein
R$^7$ is H; and R$^8$ is H or —C(=O)—R$^9$; wherein R$^9$ is $(C_{1-6})$alkyl; or
R$^7$ and R$^8$ are linked together with the N to which they are attached to form a 5- or 6-membered heterocycle optionally containing 1 to 3 additional heteroatoms each independently selected from N, O and S; and
c) Het—CH$_2$—, wherein Het is a 5- or 6-membered heterocycle optionally containing 1 to 3 additional heteroatoms each independently selected from N, O and S.

R$^{22}$-L: In this embodiment, R$^{22}$ is selected from
b) —CH$_2$—N(R$^7$)R$^8$ wherein
R$^7$ is H; and R$^8$ is H or —C(=O)—CH$_3$; or
R$^7$ and R$^8$ are linked together with the N to which they are attached to form a heterocycle selected from

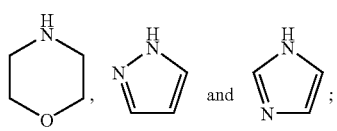

and
c) Het—CH$_2$—, wherein Het is selected from

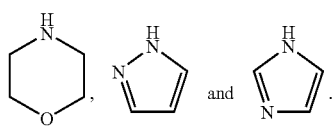

Therefore, examples of further embodiments of R$^2$ are set forth in the following table, wherein each substituent group is defined according to the definitions set forth above:

| Embodiment | R$^{21}$ | R$^{22}$ |
|---|---|---|
| R$^2$-E | R$^{21}$-A | R$^{22}$-A |
| R$^2$-F | R$^{21}$-A | R$^{22}$-D |
| R$^2$-G | R$^{21}$-C | R$^{22}$-A |
| R$^2$-H | R$^{21}$-C | R$^{22}$-E |
| R$^2$-I | R$^{21}$-C | R$^{22}$-F |
| R$^2$-J | R$^{21}$-C | R$^{22}$-H |
| R$^2$-K | R$^{21}$-C | R$^{22}$-I |
| R$^2$-L | R$^{21}$-C | R$^{22}$-K |
| R$^2$-M | R$^{21}$-D | R$^{22}$-B |
| R$^2$-N | R$^{21}$-D | R$^{22}$-E |
| R$^2$-O | R$^{21}$-D | R$^{22}$-F |
| R$^2$-P | R$^{21}$-D | R$^{22}$-H |
| R$^2$-Q | R$^{21}$-D | R$^{22}$-I |
| R$^2$-R | R$^{21}$-D | R$^{22}$-K |

R$^2$-S In still another embodiment, R$^2$ is selected from:

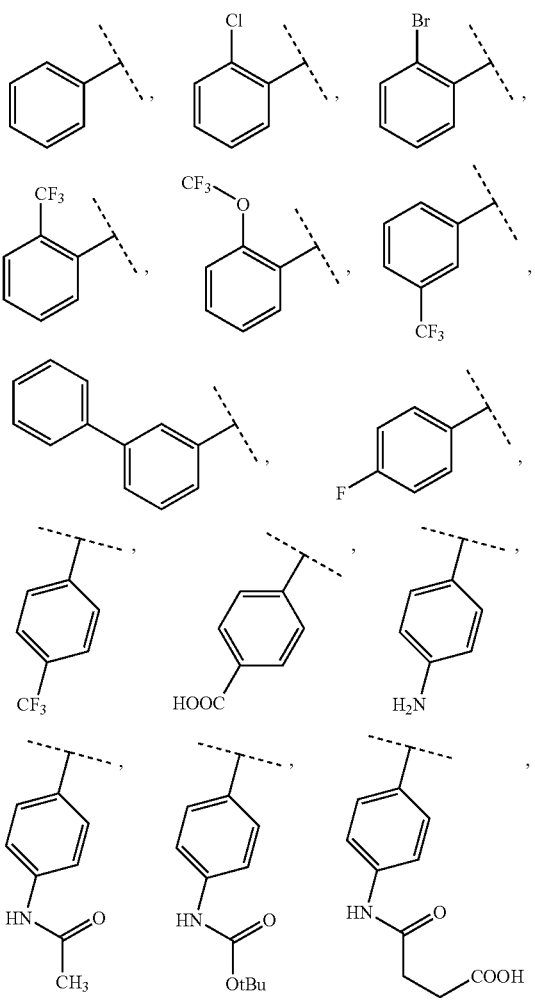

-continued
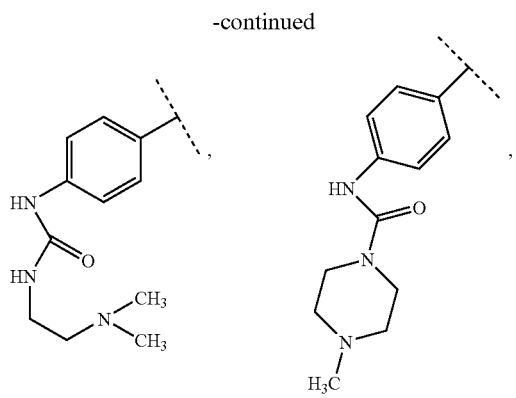
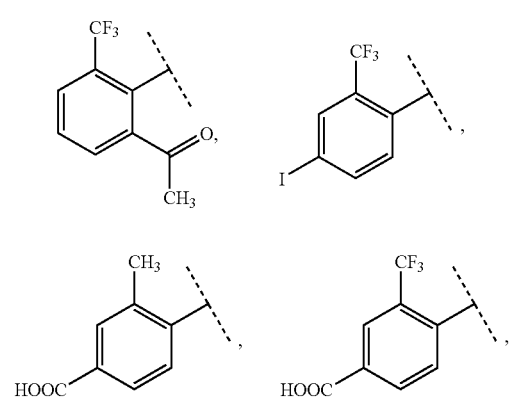
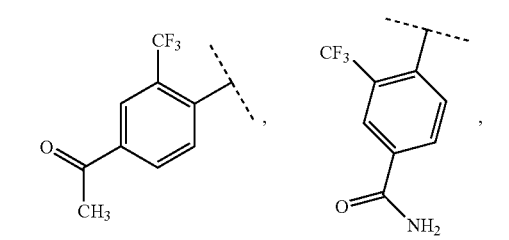
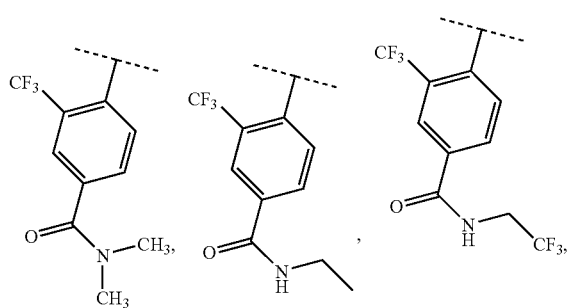
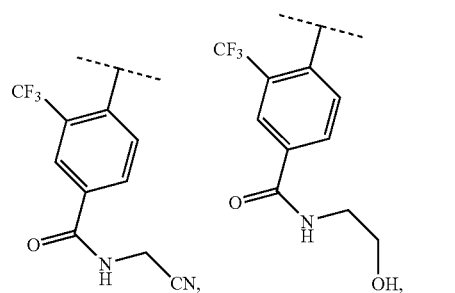
-continued
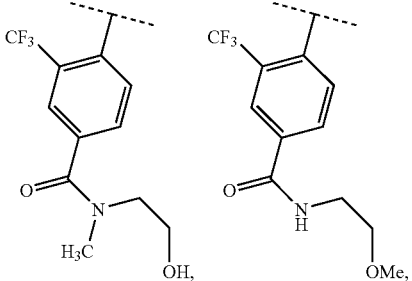
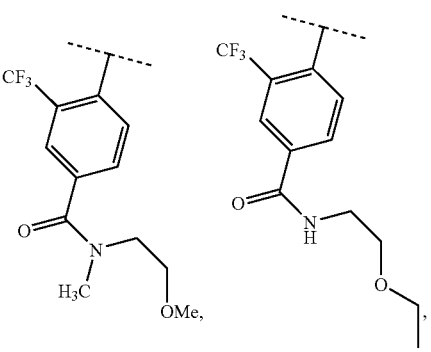
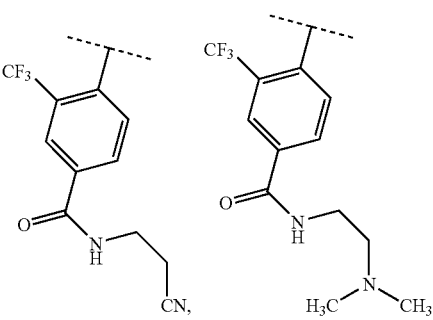
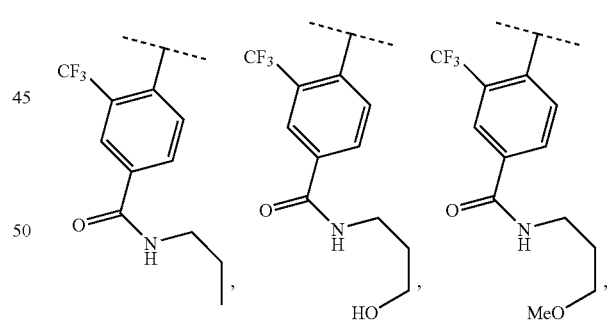
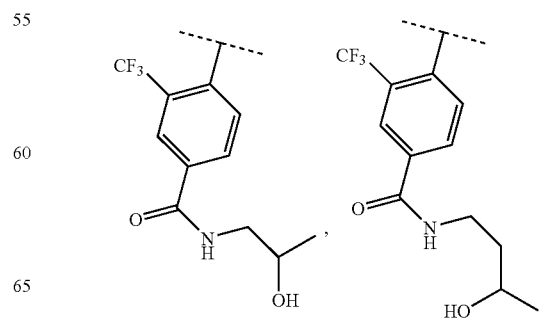

-continued
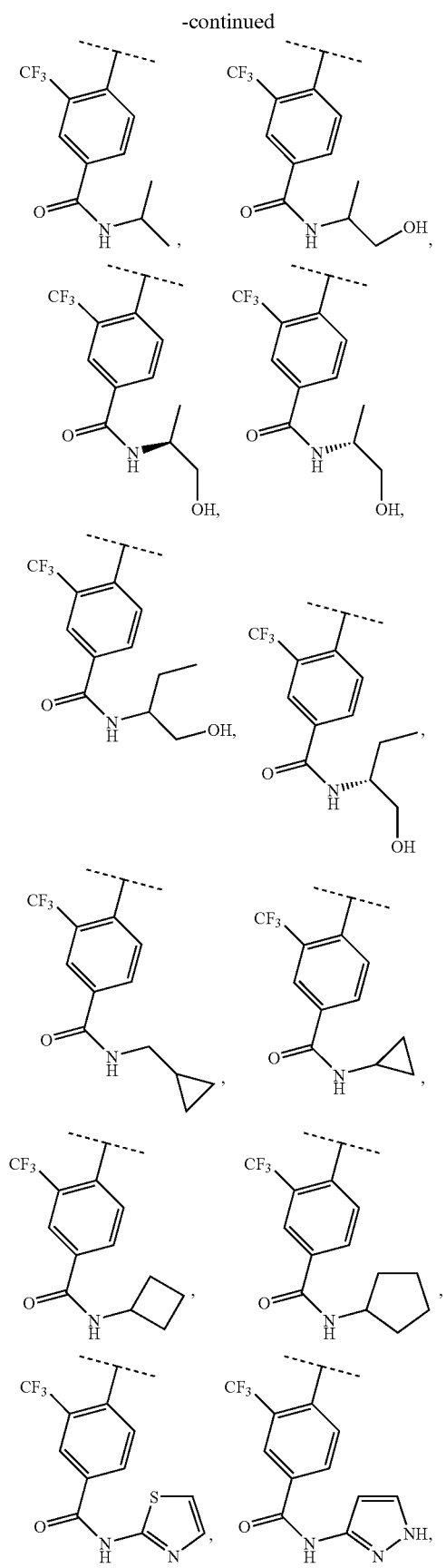
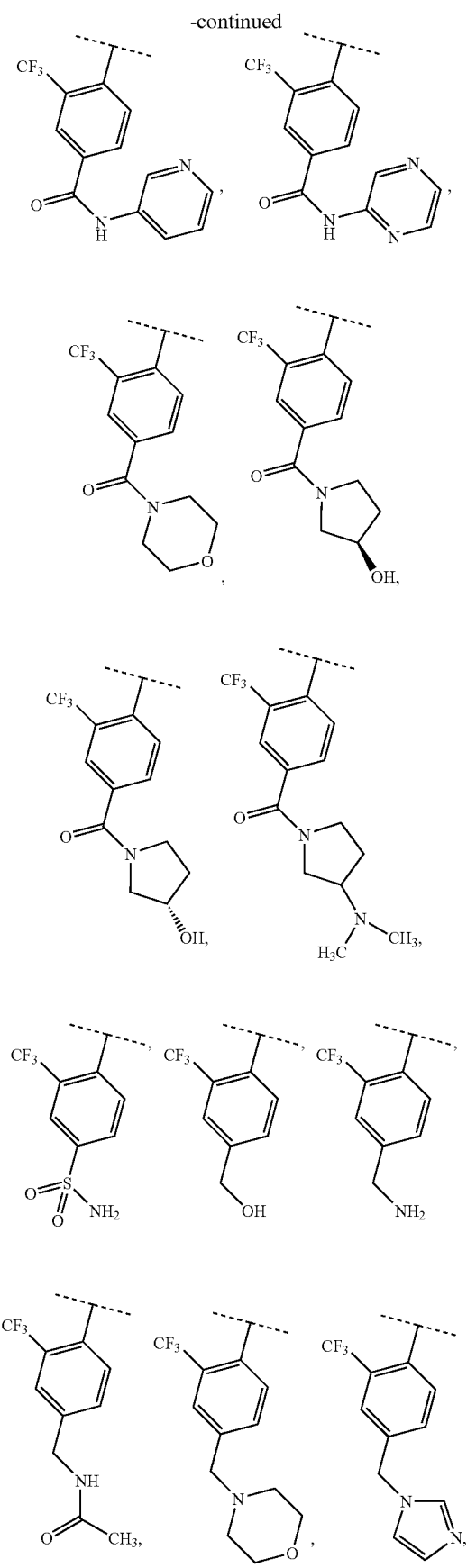

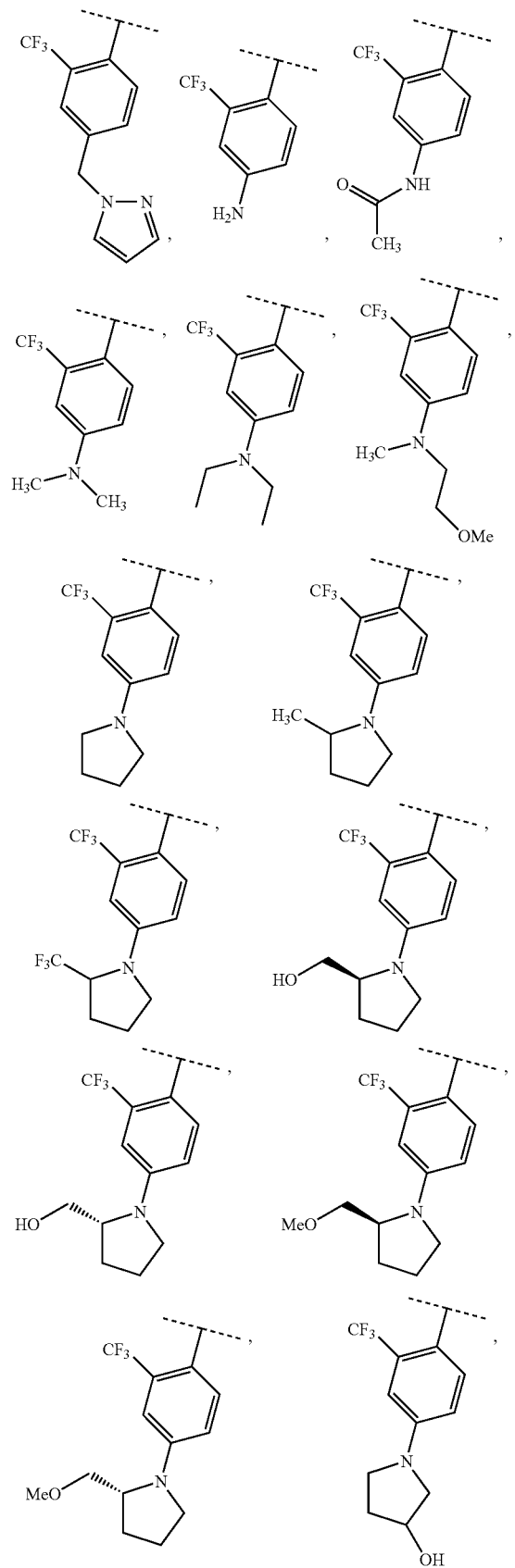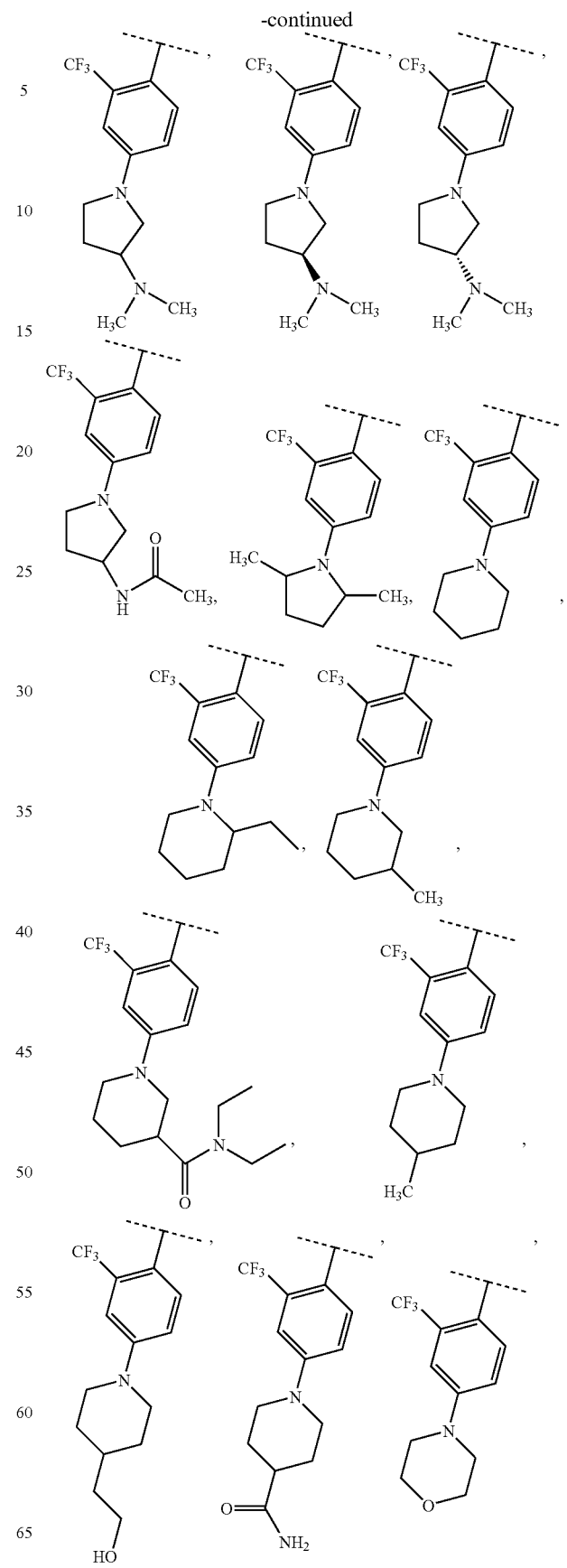

-continued
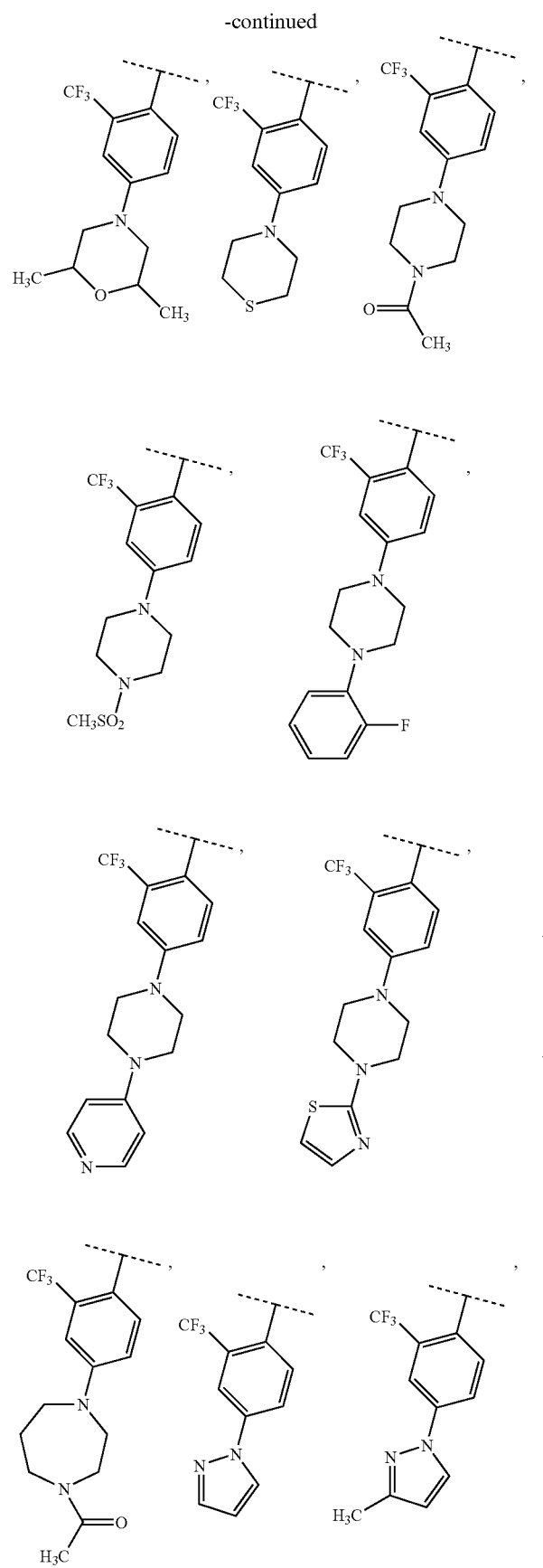
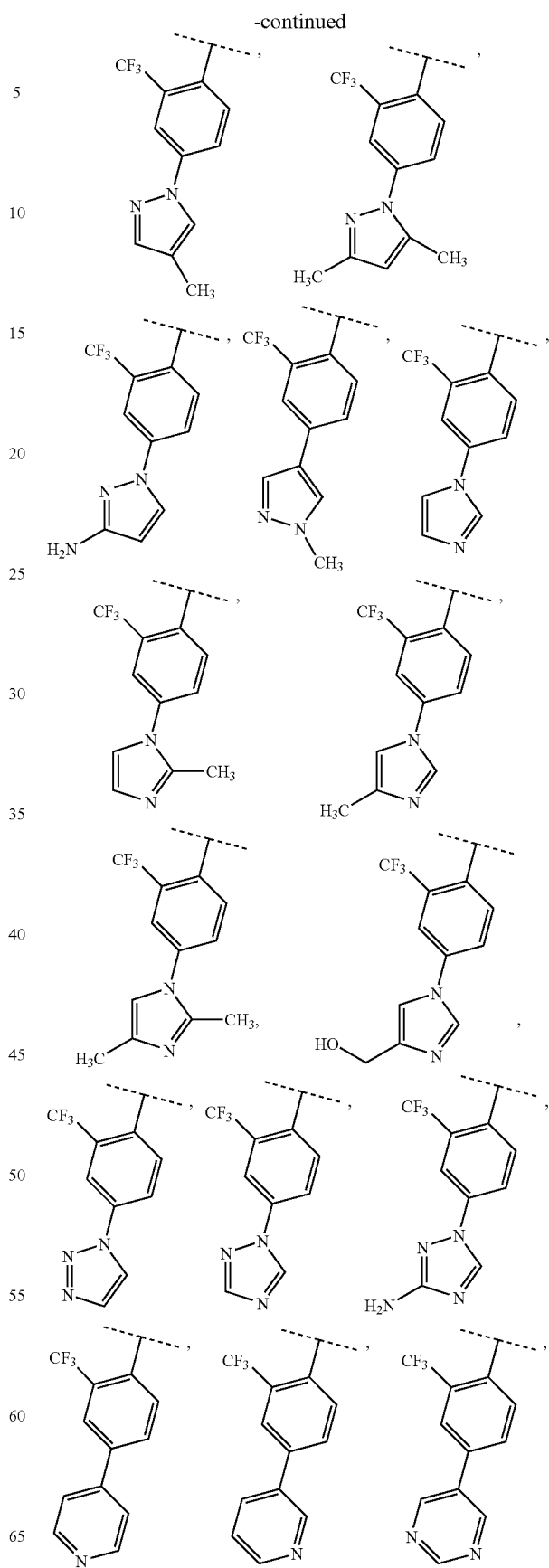

-continued
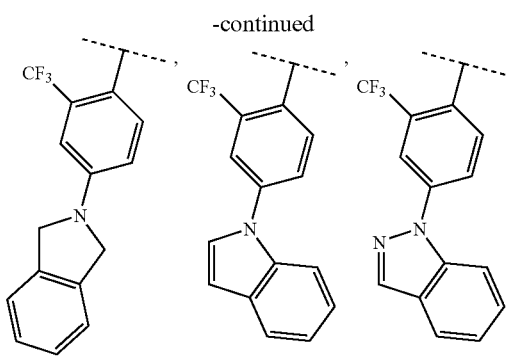
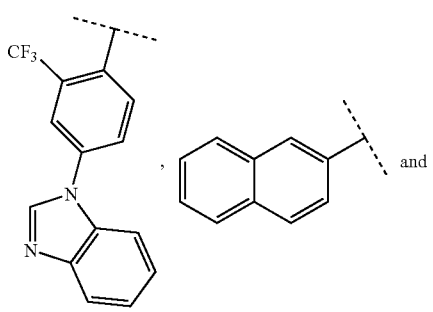
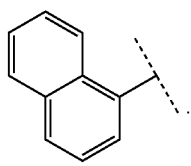
R²-T: In yet another embodiment, R² is selected from:
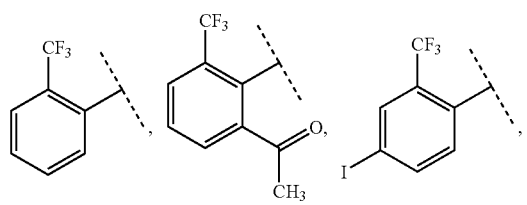
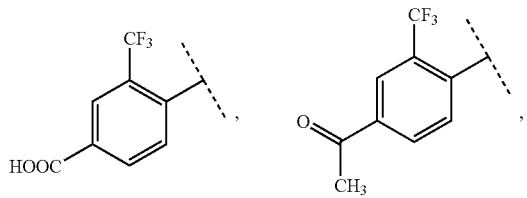
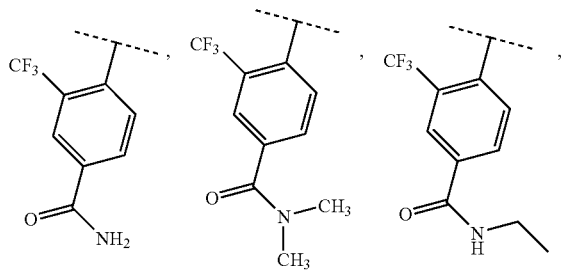
-continued
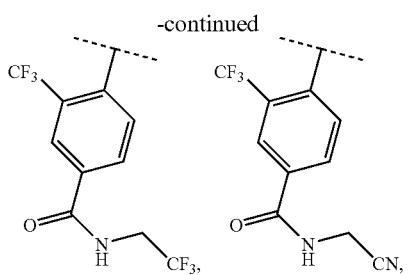
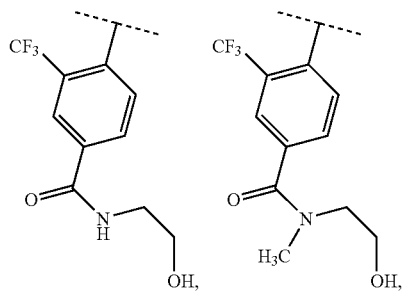
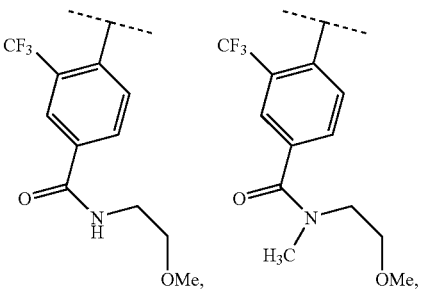
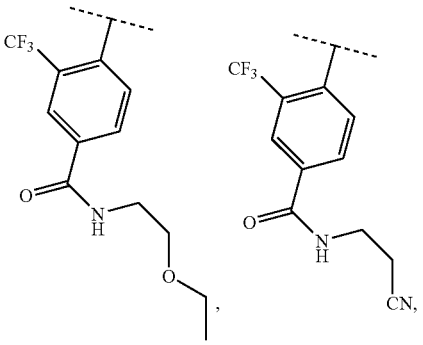
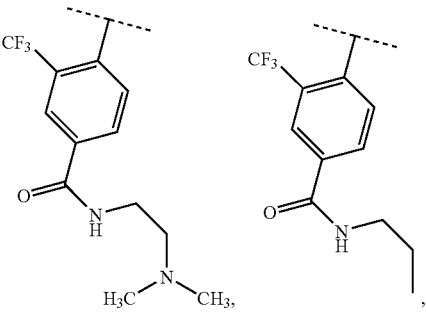

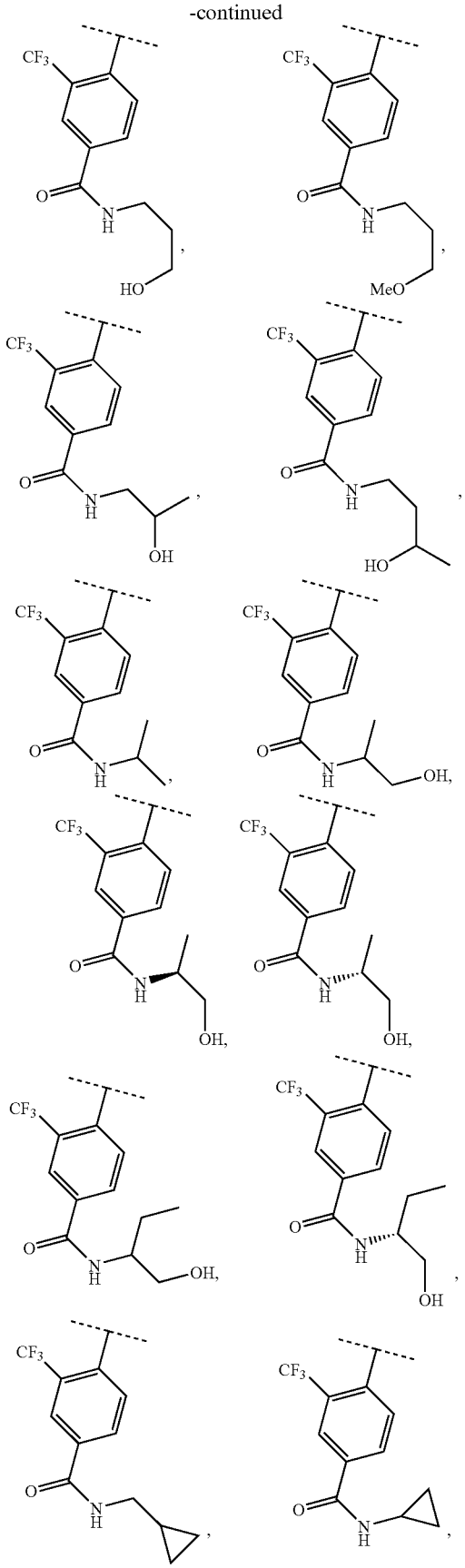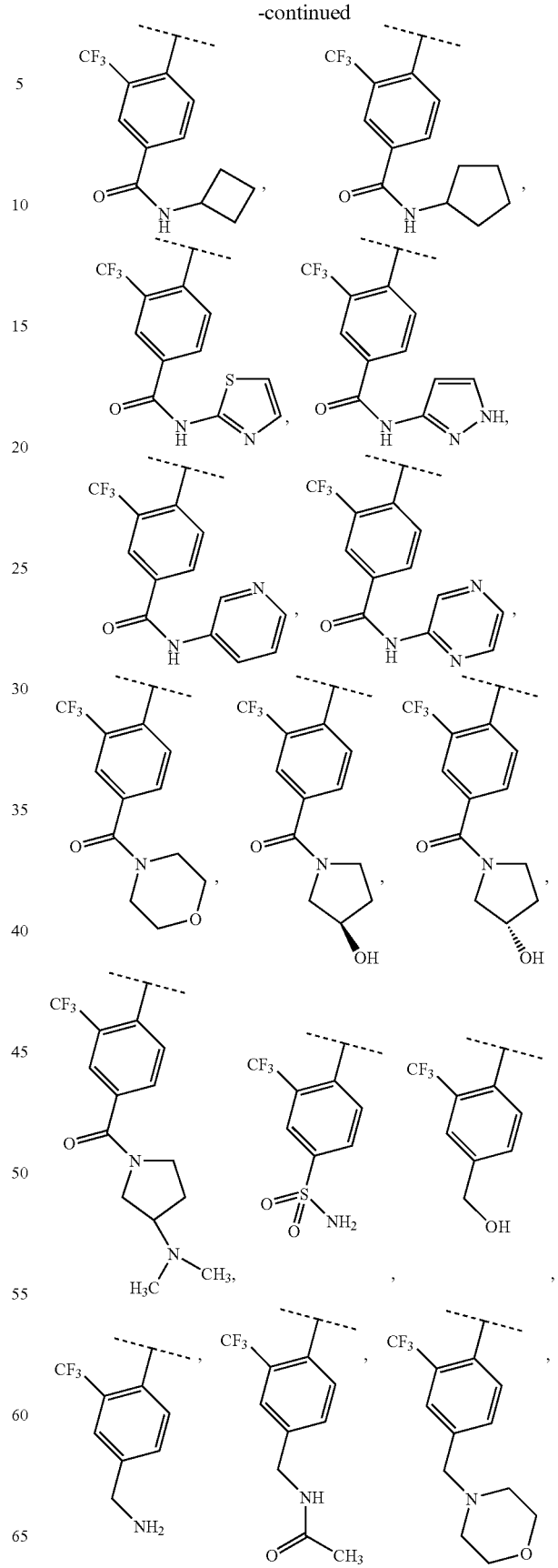

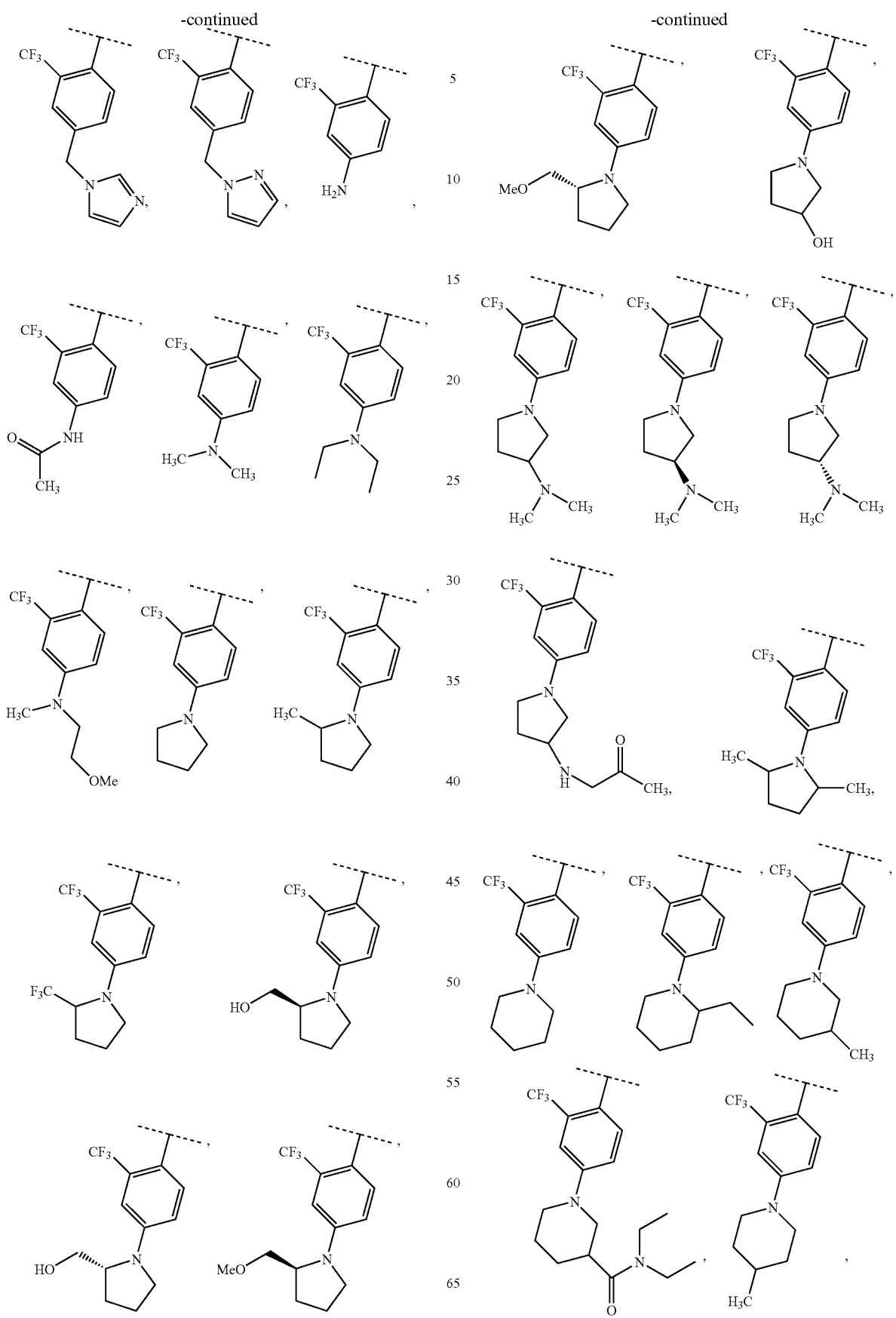

-continued
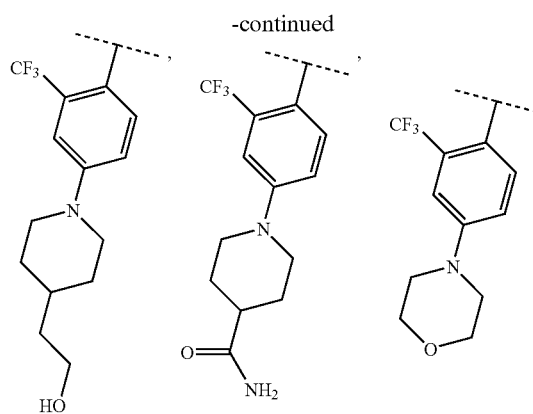
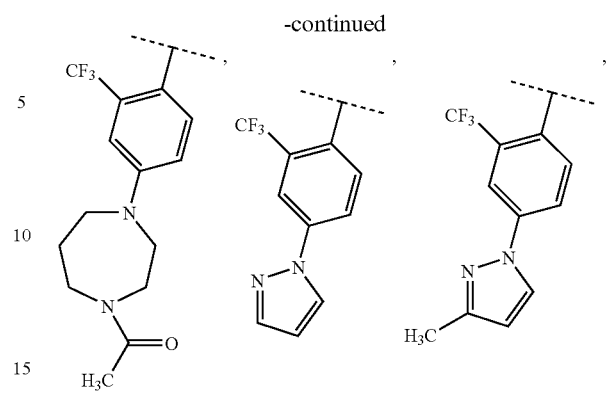
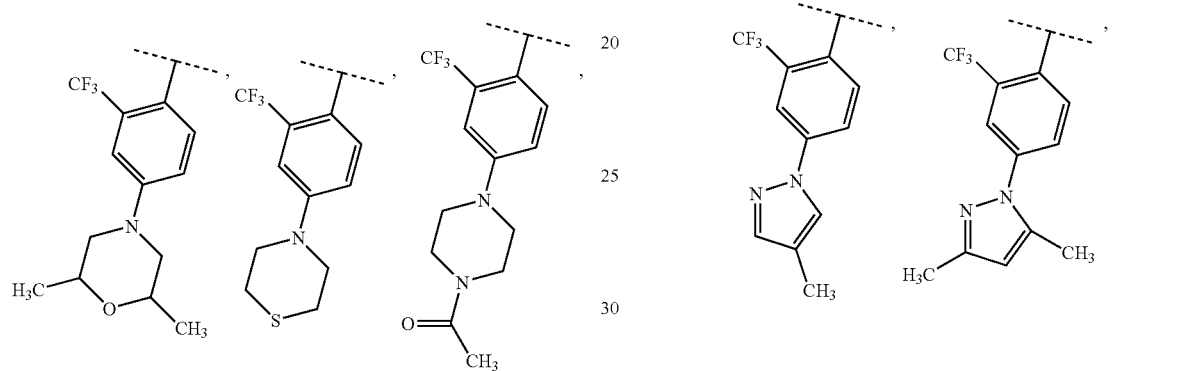
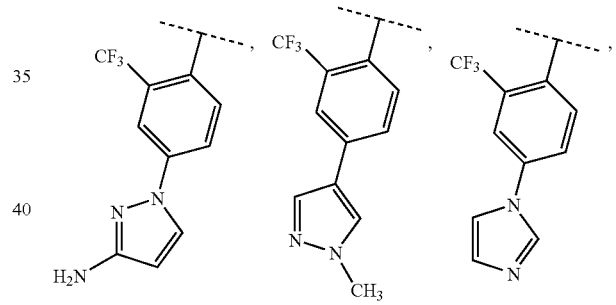
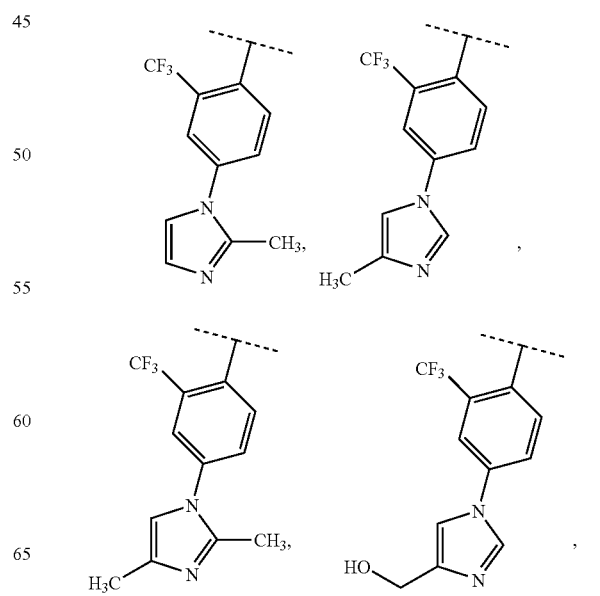

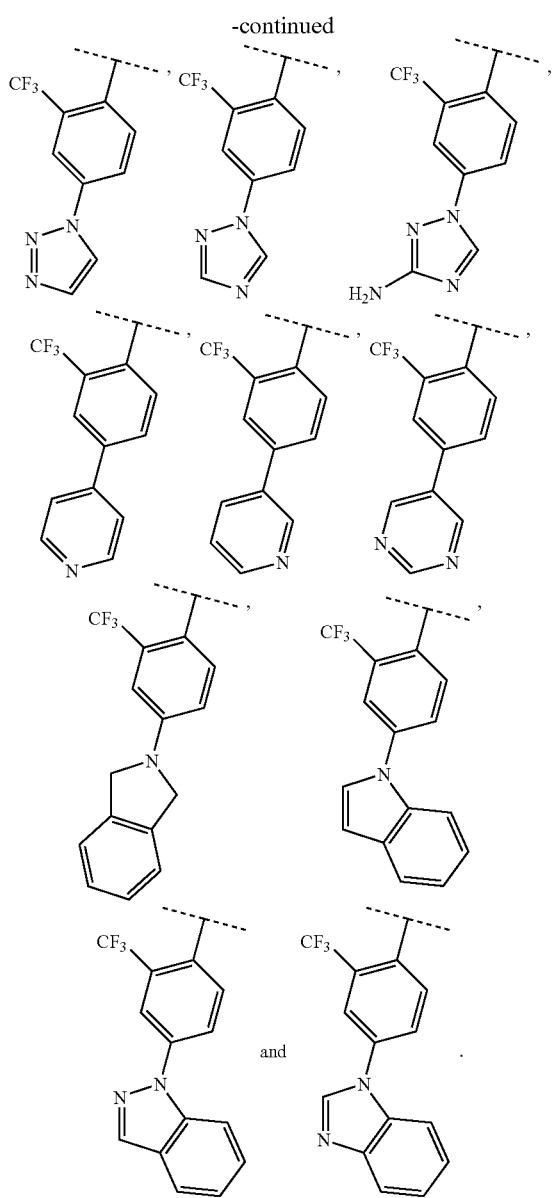

Any and each individual definition of $R^2$ as set out herein may be combined with any and each individual definition of X, $R^3$, $R^5$ and $R^6$ as set out herein.

$R^3$:

$R^3$-A: In one embodiment, $R^3$ is selected from H, halo, $(C_{1-4})$alkyl, —O—$(C_{1-4})$alkyl and —N(($C_{1-4}$)alkyl)$_2$.

$R^3$-B: In another embodiment, $R^3$ is selected from H, F, Br, CH$_3$, OCH$_3$ and —N(CH$_3$)CH$_2$CH$_3$.

$R^3$—C: In an alternative embodiment, $R^3$ is H, F, Cl or Br.

$R^3$-D: In yet another embodiment, $R^3$ is H or F.

$R^3$-E: In still another embodiment, $R^3$ is H.

Any and each individual definition of $R^3$ as set out herein may be combined with any and each individual definition of X, $R^2$, $R^5$ and $R^6$ as set out herein.

$R^5$:

$R^5$-A: In one embodiment, $R^5$ is H or $(C_{1-6})$alkyl, wherein the $(C_{1-6})$alkyl is optionally substituted with 1 to 4 substituents each independently selected from —OH, —COOH, —C(=O)—$(C_{1-6})$alkyl, —C(=O)—O—$(C_{1-6})$alkyl, —C(=O)—NH—$(C_{1-6})$alkyl, —C(=O)—N(($C_{1-6}$)alkyl)$_2$, and —SO$_2$($C_{1-6}$)alkyl.

$R^5$-B: In another embodiment, $R^5$ is selected from H or $(C_{1-4})$alkyl, wherein the $(C_{1-4})$alkyl is optionally substituted with 1 or 2 substituents each independently selected from —OH and —COOH.

$R^5$—C: In still another embodiment, $R^5$ is selected from H, methyl, ethyl, propyl, 1-methylethyl,

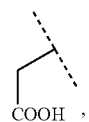

and

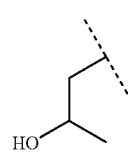

$R^5$-D: In yet another embodiment, $R^5$ is methyl, ethyl, propyl or 1-methylethyl.

$R^5$-E: In a further embodiment, $R^5$ is 1-methylethyl.

$R^5$-F: In an alternative embodiment, $R^5$ is Het optionally substituted with 1 to 4 substituents each independently selected from $(C_{1-6})$alkyl, —OH, —COOH, —C(=O)—$(C_{1-6})$alkyl, —C(=O)—O—$(C_{1-6})$alkyl, —C(=O)—NH—$(C_{1-6})$alkyl, —C(=O)—N(($C_{1-6}$)alkyl)$_2$, and —SO$_2$($C_{1-6}$)alkyl.

$R^5$-G: In another alternative embodiment, $R^5$ is a 5- or 6-membered saturated heterocycle containing 1 to 3 heteroatoms each independently selected from O, N and S, the heterocycle being optionally substituted with 1 to 4 substituents each independently selected from $(C_{1-4})$alkyl, —C(=O)—$(C_{1-4})$alkyl, —C(=O)—O—$(C_{1-4})$alkyl, —C(=O)—NH—$(C_{1-4})$alkyl, —C(=O)—N(($C_{1-4}$)alkyl)$_2$, and —SO$_2$($C_{1-4}$)alkyl.

$R^5$-H: In yet another alternative embodiment, $R^5$ is a 6-membered saturated heterocycle containing 1 or 2 heteroatoms each independently selected from O and N, the heterocycle being optionally substituted with 1 or 2 substituents each independently selected from CH$_3$, —C(=O)—CH$_3$, —C(=O)—O—CH$_3$, —C(=O)—O—C(CH$_3$)$_3$, —C(=O)—NH—CH$_2$CH$_3$ and —SO$_2$CH$_3$.

$R^5$-I: In still another alternative embodiment, $R^5$ is selected from:

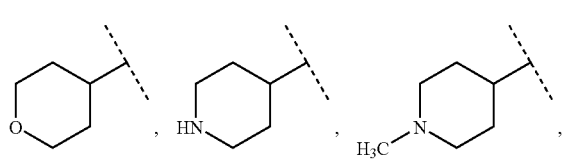

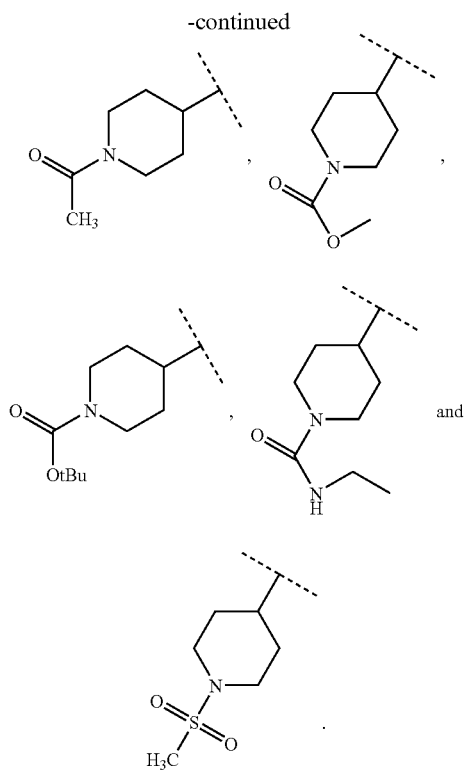

Any and each individual definition of $R^5$ as set out herein may be combined with any and each individual definition of X, $R^2$, $R^3$ and $R^6$ as set out herein.

$R^6$:

$R^6$-A: In one embodiment, $R^6$ is selected from $(C_{5-7})$cycloalkyl and $(C_{5-7})$cycloalkyl-$(C_{1-3})$alkyl-, the $(C_{5-7})$cycloalkyl and $(C_{5-7})$cycloalkyl-$(C_{1-3})$alkyl- each being optionally substituted with 1 to 5 substituents each independently selected from halo, $(C_{1-6})$alkyl, $(C_{1-6})$haloalkyl, —OH, —SH, —O—$(C_{1-4})$alkyl and —S—$(C_{1-4})$alkyl.

$R^6$-B: In another embodiment, $R^6$ is cyclopentyl, cyclohexyl or cycloheptyl, the cyclopentyl, cyclohexyl and cycloheptyl each being optionally substituted with 1 to 3 substituents each independently selected from halo, —OH, $(C_{1-4})$alkyl and $(C_{1-4})$haloalkyl.

$R^6$-C: In yet another embodiment, $R^6$ is cyclohexyl optionally substituted with 1 to 3 substituents each independently selected from fluoro, —OH, $(C_{1-4})$alkyl and $CF_3$.

$R^6$-D: In still another embodiment, $R^6$ is selected from:

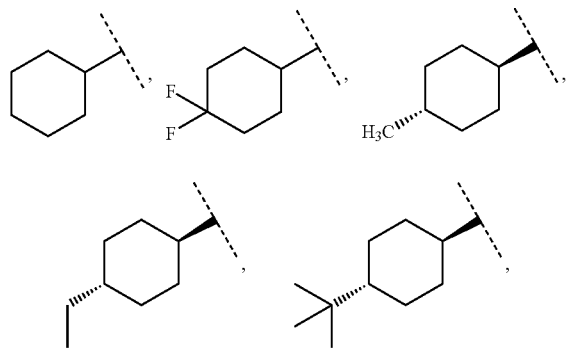

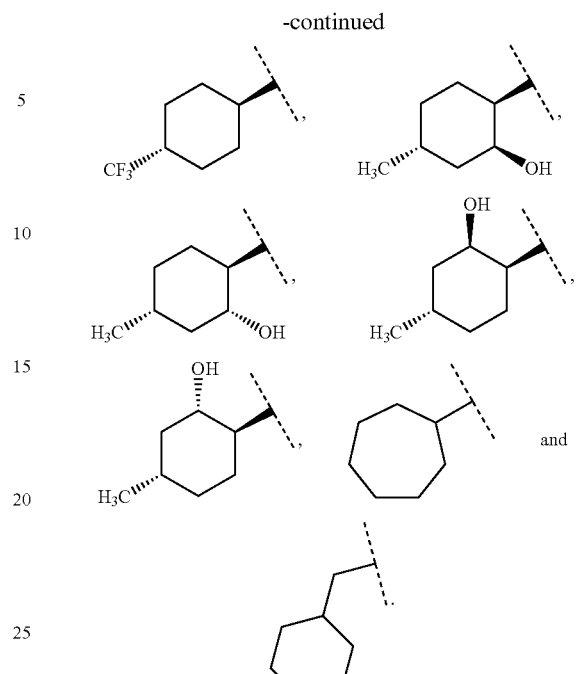

$R^6$-E: In still another embodiment, $R^6$ is

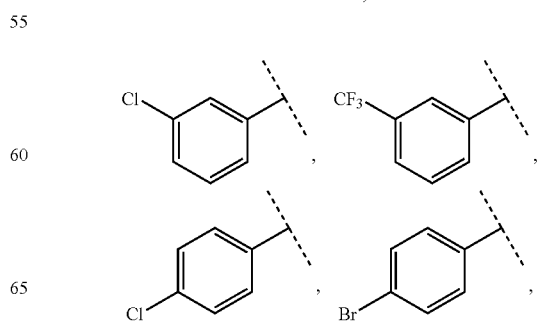

$R^6$-F: In an alternative embodiment, $R^6$ is aryl optionally substituted with 1 to 5 substituents each independently selected from halo, $(C_{1-6})$alkyl, $(C_{1-6})$haloalkyl, —OH, —SH, —O—$(C_{1-4})$alkyl and —S—$(C_{1-4})$alkyl.

$R^6$-G: In another alternative embodiment, $R^6$ is phenyl optionally substituted with 1 to 5 substituents each independently selected from halo, $(C_{1-4})$alkyl, $(C_{1-4})$haloalkyl and —S—$(C_{1-4})$alkyl.

$R^6$-H: In yet another alternative embodiment, $R^6$ is phenyl optionally substituted with 1 to 3 substituents each independently selected from F, Cl, Br, methyl, ethyl, $CF_3$ and —S—$CH_3$.

$R^6$-I: In still another embodiment, $R^6$ is selected from:

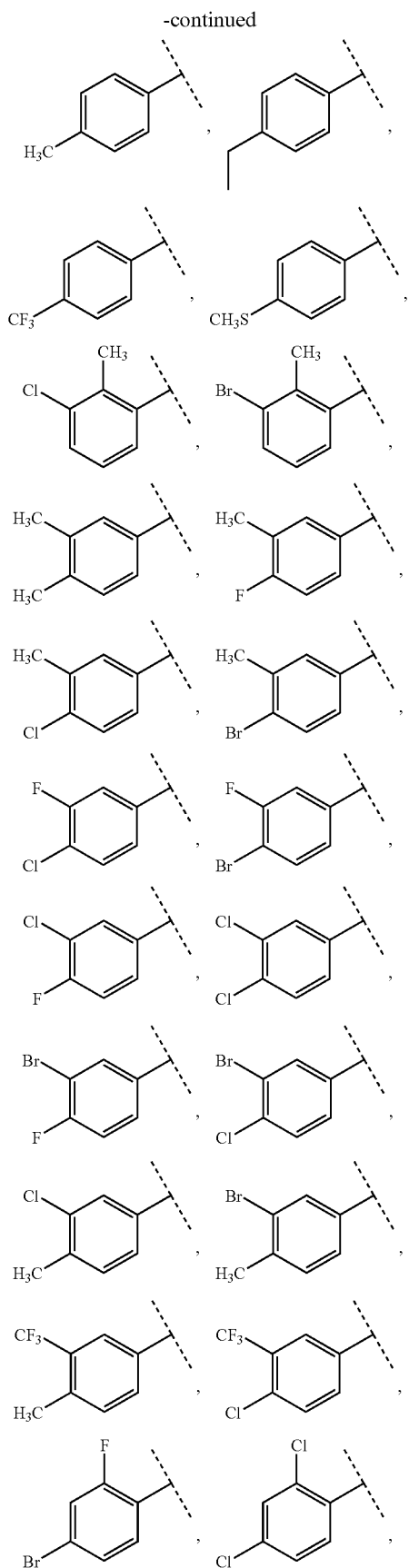

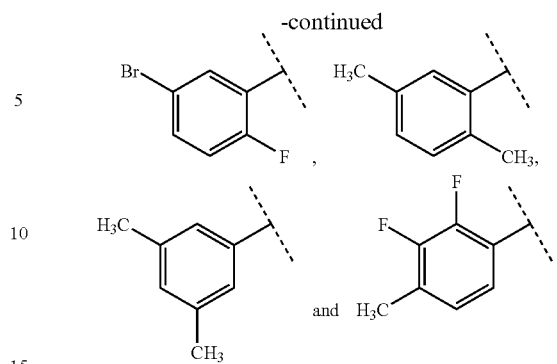

Any and each individual definition of $R^6$ as set out herein may be combined with any and each individual definition of X, $R^2$, $R^3$, and $R^5$ as set out herein.

Examples of preferred subgeneric embodiments of the present invention are set forth in the following table, wherein each substituent group of each embodiment is defined according to the definitions set forth above:

| Embodiment | X | $R^2$ | $R^3$ | $R^5$ | $R^6$ |
|---|---|---|---|---|---|
| E-1 | X-A | $R^2$-A | $R^3$-A | $R^5$-A | $R^6$-A |
| E-2 | X-B | $R^2$-A | $R^3$-A | $R^5$-A | $R^6$-A |
| E-3 | X-A | $R^2$-A | $R^3$-A | $R^5$-F | $R^6$-A |
| E-4 | X-B | $R^2$-A | $R^3$-A | $R^5$-F | $R^6$-A |
| E-5 | X-A | $R^2$-A | $R^3$-A | $R^5$-A | $R^6$-F |
| E-6 | X-B | $R^2$-A | $R^3$-A | $R^5$-A | $R^6$-F |
| E-7 | X-A | $R^2$-A | $R^3$-A | $R^5$-F | $R^6$-F |
| E-8 | X-B | $R^2$-A | $R^3$-A | $R^5$-F | $R^6$-F |
| E-9 | X-A | $R^2$-D | $R^3$-A | $R^5$-B | $R^6$-B |
| E-10 | X-A | $R^2$-D | $R^3$-E | $R^5$-B | $R^6$-B |
| E-11 | X-A | $R^2$-D | $R^3$-A | $R^5$-E | $R^6$-B |
| E-12 | X-A | $R^2$-D | $R^3$-E | $R^5$-E | $R^6$-B |
| E-13 | X-A | $R^2$-D | $R^3$-A | $R^5$-G | $R^6$-B |
| E-14 | X-A | $R^2$-D | $R^3$-E | $R^5$-G | $R^6$-B |
| E-15 | X-A | $R^2$-D | $R^3$-A | $R^5$-B | $R^6$-E |
| E-16 | X-A | $R^2$-D | $R^3$-E | $R^5$-B | $R^6$-E |
| E-17 | X-A | $R^2$-D | $R^3$-A | $R^5$-E | $R^6$-E |
| E-18 | X-A | $R^2$-D | $R^3$-E | $R^5$-E | $R^6$-E |
| E-19 | X-A | $R^2$-D | $R^3$-A | $R^5$-G | $R^6$-E |
| E-20 | X-A | $R^2$-D | $R^3$-E | $R^5$-G | $R^6$-E |
| E-21 | X-A | $R^2$-D | $R^3$-A | $R^5$-B | $R^6$-G |
| E-22 | X-A | $R^2$-D | $R^3$-E | $R^5$-B | $R^6$-G |
| E-23 | X-A | $R^2$-D | $R^3$-A | $R^5$-E | $R^6$-G |
| E-24 | X-A | $R^2$-D | $R^3$-E | $R^5$-E | $R^6$-G |
| E-25 | X-A | $R^2$-D | $R^3$-A | $R^5$-G | $R^6$-G |
| E-26 | X-A | $R^2$-D | $R^3$-E | $R^5$-G | $R^6$-G |
| E-27 | X-A | $R^2$-E | $R^3$-A | $R^5$-B | $R^6$-B |
| E-28 | X-A | $R^2$-E | $R^3$-E | $R^5$-B | $R^6$-B |
| E-29 | X-A | $R^2$-E | $R^3$-A | $R^5$-E | $R^6$-B |
| E-30 | X-A | $R^2$-E | $R^3$-E | $R^5$-E | $R^6$-B |
| E-31 | X-A | $R^2$-E | $R^3$-A | $R^5$-G | $R^6$-B |
| E-32 | X-A | $R^2$-E | $R^3$-E | $R^5$-G | $R^6$-B |
| E-33 | X-A | $R^2$-E | $R^3$-A | $R^5$-B | $R^6$-E |
| E-34 | X-A | $R^2$-E | $R^3$-E | $R^5$-B | $R^6$-E |
| E-35 | X-A | $R^2$-E | $R^3$-A | $R^5$-E | $R^6$-E |
| E-36 | X-A | $R^2$-E | $R^3$-E | $R^5$-E | $R^6$-E |
| E-37 | X-A | $R^2$-E | $R^3$-A | $R^5$-G | $R^6$-E |
| E-38 | X-A | $R^2$-E | $R^3$-E | $R^5$-G | $R^6$-E |
| E-39 | X-A | $R^2$-E | $R^3$-A | $R^5$-B | $R^6$-G |
| E-40 | X-A | $R^2$-E | $R^3$-E | $R^5$-B | $R^6$-G |
| E-41 | X-A | $R^2$-E | $R^3$-A | $R^5$-E | $R^6$-G |
| E-42 | X-A | $R^2$-E | $R^3$-E | $R^5$-E | $R^6$-G |
| E-43 | X-A | $R^2$-E | $R^3$-A | $R^5$-G | $R^6$-G |
| E-44 | X-A | $R^2$-E | $R^3$-E | $R^5$-G | $R^6$-G |
| E-45 | X-A | $R^2$-F | $R^3$-A | $R^5$-B | $R^6$-B |
| E-46 | X-A | $R^2$-F | $R^3$-E | $R^5$-B | $R^6$-B |
| E-47 | X-A | $R^2$-F | $R^3$-A | $R^5$-E | $R^6$-B |
| E-48 | X-A | $R^2$-F | $R^3$-E | $R^5$-E | $R^6$-B |

| Embodiment | X | R² | R³ | R⁵ | R⁶ |
|---|---|---|---|---|---|
| E-49 | X-A | R²-F | R³-A | R⁵-G | R⁶-B |
| E-50 | X-A | R²-F | R³-E | R⁵-G | R⁶-B |
| E-51 | X-A | R²-F | R³-A | R⁵-B | R⁶-E |
| E-52 | X-A | R²-F | R³-E | R⁵-B | R⁶-E |
| E-53 | X-A | R²-F | R³-A | R⁵-E | R⁶-E |
| E-54 | X-A | R²-F | R³-E | R⁵-E | R⁶-E |
| E-55 | X-A | R²-F | R³-A | R⁵-G | R⁶-E |
| E-56 | X-A | R²-F | R³-E | R⁵-G | R⁶-E |
| E-57 | X-A | R²-F | R³-A | R⁵-B | R⁶-G |
| E-58 | X-A | R²-F | R³-E | R⁵-B | R⁶-G |
| E-59 | X-A | R²-F | R³-A | R⁵-E | R⁶-G |
| E-60 | X-A | R²-F | R³-E | R⁵-E | R⁶-G |
| E-61 | X-A | R²-F | R³-A | R⁵-G | R⁶-G |
| E-62 | X-A | R²-F | R³-E | R⁵-G | R⁶-G |
| E-63 | X-A | R²-G | R³-A | R⁵-B | R⁶-B |
| E-64 | X-A | R²-G | R³-E | R⁵-B | R⁶-B |
| E-65 | X-A | R²-G | R³-A | R⁵-E | R⁶-B |
| E-66 | X-A | R²-G | R³-E | R⁵-E | R⁶-B |
| E-67 | X-A | R²-G | R³-A | R⁵-G | R⁶-B |
| E-68 | X-A | R²-G | R³-E | R⁵-G | R⁶-B |
| E-69 | X-A | R²-G | R³-A | R⁵-B | R⁶-E |
| E-70 | X-A | R²-G | R³-E | R⁵-B | R⁶-E |
| E-71 | X-A | R²-G | R³-A | R⁵-E | R⁶-E |
| E-72 | X-A | R²-G | R³-E | R⁵-E | R⁶-E |
| E-73 | X-A | R²-G | R³-A | R⁵-G | R⁶-E |
| E-74 | X-A | R²-G | R³-E | R⁵-G | R⁶-E |
| E-75 | X-A | R²-G | R³-A | R⁵-B | R⁶-G |
| E-76 | X-A | R²-G | R³-E | R⁵-B | R⁶-G |
| E-77 | X-A | R²-G | R³-A | R⁵-E | R⁶-G |
| E-78 | X-A | R²-G | R³-E | R⁵-E | R⁶-G |
| E-79 | X-A | R²-G | R³-A | R⁵-G | R⁶-G |
| E-80 | X-A | R²-G | R³-E | R⁵-G | R⁶-G |
| E-81 | X-A | R²-H | R³-A | R⁵-B | R⁶-B |
| E-82 | X-A | R²-H | R³-E | R⁵-B | R⁶-B |
| E-83 | X-A | R²-H | R³-A | R⁵-E | R⁶-B |
| E-84 | X-A | R²-H | R³-E | R⁵-E | R⁶-B |
| E-85 | X-A | R²-H | R³-A | R⁵-G | R⁶-B |
| E-86 | X-A | R²-H | R³-E | R⁵-G | R⁶-B |
| E-87 | X-A | R²-H | R³-A | R⁵-B | R⁶-E |
| E-88 | X-A | R²-H | R³-E | R⁵-B | R⁶-E |
| E-89 | X-A | R²-H | R³-A | R⁵-E | R⁶-E |
| E-90 | X-A | R²-H | R³-E | R⁵-E | R⁶-E |
| E-91 | X-A | R²-H | R³-A | R⁵-G | R⁶-E |
| E-92 | X-A | R²-H | R³-E | R⁵-G | R⁶-E |
| E-93 | X-A | R²-H | R³-A | R⁵-B | R⁶-G |
| E-94 | X-A | R²-H | R³-E | R⁵-B | R⁶-G |
| E-95 | X-A | R²-H | R³-A | R⁵-E | R⁶-G |
| E-96 | X-A | R²-H | R³-E | R⁵-E | R⁶-G |
| E-97 | X-A | R²-H | R³-A | R⁵-G | R⁶-G |
| E-98 | X-A | R²-H | R³-E | R⁵-G | R⁶-G |
| E-99 | X-A | R²-I | R³-A | R⁵-B | R⁶-B |
| E-100 | X-A | R²-I | R³-E | R⁵-B | R⁶-B |
| E-101 | X-A | R²-I | R³-A | R⁵-E | R⁶-B |
| E-102 | X-A | R²-I | R³-E | R⁵-E | R⁶-B |
| E-103 | X-A | R²-I | R³-A | R⁵-G | R⁶-B |
| E-104 | X-A | R²-I | R³-E | R⁵-G | R⁶-B |
| E-105 | X-A | R²-I | R³-A | R⁵-B | R⁶-E |
| E-106 | X-A | R²-I | R³-E | R⁵-B | R⁶-E |
| E-107 | X-A | R²-I | R³-A | R⁵-E | R⁶-E |
| E-108 | X-A | R²-I | R³-E | R⁵-E | R⁶-E |
| E-109 | X-A | R²-I | R³-A | R⁵-G | R⁶-E |
| E-110 | X-A | R²-I | R³-E | R⁵-G | R⁶-E |
| E-111 | X-A | R²-I | R³-A | R⁵-B | R⁶-G |
| E-112 | X-A | R²-I | R³-E | R⁵-B | R⁶-G |
| E-113 | X-A | R²-I | R³-A | R⁵-E | R⁶-G |
| E-114 | X-A | R²-I | R³-E | R⁵-E | R⁶-G |
| E-115 | X-A | R²-I | R³-A | R⁵-G | R⁶-G |
| E-116 | X-A | R²-I | R³-E | R⁵-G | R⁶-G |
| E-117 | X-A | R²-J | R³-A | R⁵-B | R⁶-B |
| E-118 | X-A | R²-J | R³-E | R⁵-B | R⁶-B |
| E-119 | X-A | R²-J | R³-A | R⁵-E | R⁶-B |
| E-120 | X-A | R²-J | R³-E | R⁵-E | R⁶-B |
| E-121 | X-A | R²-J | R³-A | R⁵-G | R⁶-B |
| E-122 | X-A | R²-J | R³-E | R⁵-G | R⁶-B |
| E-123 | X-A | R²-J | R³-A | R⁵-B | R⁶-E |
| E-124 | X-A | R²-J | R³-E | R⁵-B | R⁶-E |
| E-125 | X-A | R²-J | R³-A | R⁵-E | R⁶-E |
| E-126 | X-A | R²-J | R³-E | R⁵-E | R⁶-E |
| E-127 | X-A | R²-J | R³-A | R⁵-G | R⁶-E |
| E-128 | X-A | R²-J | R³-E | R⁵-G | R⁶-E |
| E-129 | X-A | R²-J | R³-A | R⁵-B | R⁶-G |
| E-130 | X-A | R²-J | R³-E | R⁵-B | R⁶-G |
| E-131 | X-A | R²-J | R³-A | R⁵-E | R⁶-G |
| E-132 | X-A | R²-J | R³-E | R⁵-E | R⁶-G |
| E-133 | X-A | R²-J | R³-A | R⁵-G | R⁶-G |
| E-134 | X-A | R²-J | R³-E | R⁵-G | R⁶-G |
| E-135 | X-A | R²-K | R³-A | R⁵-B | R⁶-B |
| E-136 | X-A | R²-K | R³-E | R⁵-B | R⁶-B |
| E-137 | X-A | R²-K | R³-A | R⁵-E | R⁶-B |
| E-138 | X-A | R²-K | R³-E | R⁵-E | R⁶-B |
| E-139 | X-A | R²-K | R³-A | R⁵-G | R⁶-B |
| E-140 | X-A | R²-K | R³-E | R⁵-G | R⁶-B |
| E-141 | X-A | R²-K | R³-A | R⁵-B | R⁶-E |
| E-142 | X-A | R²-K | R³-E | R⁵-B | R⁶-E |
| E-143 | X-A | R²-K | R³-A | R⁵-E | R⁶-E |
| E-144 | X-A | R²-K | R³-E | R⁵-E | R⁶-E |
| E-145 | X-A | R²-K | R³-A | R⁵-G | R⁶-E |
| E-146 | X-A | R²-K | R³-E | R⁵-G | R⁶-E |
| E-147 | X-A | R²-K | R³-A | R⁵-B | R⁶-G |
| E-148 | X-A | R²-K | R³-E | R⁵-B | R⁶-G |
| E-149 | X-A | R²-K | R³-A | R⁵-E | R⁶-G |
| E-150 | X-A | R²-K | R³-E | R⁵-E | R⁶-G |
| E-151 | X-A | R²-K | R³-A | R⁵-G | R⁶-G |
| E-152 | X-A | R²-K | R³-E | R⁵-G | R⁶-G |
| E-153 | X-A | R²-L | R³-A | R⁵-B | R⁶-B |
| E-154 | X-A | R²-L | R³-E | R⁵-B | R⁶-B |
| E-155 | X-A | R²-L | R³-A | R⁵-E | R⁶-B |
| E-156 | X-A | R²-L | R³-E | R⁵-E | R⁶-B |
| E-157 | X-A | R²-L | R³-A | R⁵-G | R⁶-B |
| E-158 | X-A | R²-L | R³-E | R⁵-G | R⁶-B |
| E-159 | X-A | R²-L | R³-A | R⁵-B | R⁶-E |
| E-160 | X-A | R²-L | R³-E | R⁵-B | R⁶-E |
| E-161 | X-A | R²-L | R³-A | R⁵-E | R⁶-E |
| E-162 | X-A | R²-L | R³-E | R⁵-E | R⁶-E |
| E-163 | X-A | R²-L | R³-A | R⁵-G | R⁶-E |
| E-164 | X-A | R²-L | R³-E | R⁵-G | R⁶-E |
| E-165 | X-A | R²-L | R³-A | R⁵-B | R⁶-G |
| E-166 | X-A | R²-L | R³-E | R⁵-B | R⁶-G |
| E-167 | X-A | R²-L | R³-A | R⁵-E | R⁶-G |
| E-168 | X-A | R²-L | R³-E | R⁵-E | R⁶-G |
| E-169 | X-A | R²-L | R³-A | R⁵-G | R⁶-G |
| E-170 | X-A | R²-L | R³-E | R⁵-G | R⁶-G |
| E-171 | X-A | R²-M | R³-A | R⁵-B | R⁶-B |
| E-172 | X-A | R²-M | R³-E | R⁵-B | R⁶-B |
| E-173 | X-A | R²-M | R³-A | R⁵-E | R⁶-B |
| E-174 | X-A | R²-M | R³-E | R⁵-E | R⁶-B |
| E-175 | X-A | R²-M | R³-A | R⁵-G | R⁶-B |
| E-176 | X-A | R²-M | R³-E | R⁵-G | R⁶-B |
| E-177 | X-A | R²-M | R³-A | R⁵-B | R⁶-E |
| E-178 | X-A | R²-M | R³-E | R⁵-B | R⁶-E |
| E-179 | X-A | R²-M | R³-A | R⁵-E | R⁶-E |
| E-180 | X-A | R²-M | R³-E | R⁵-E | R⁶-E |
| E-181 | X-A | R²-M | R³-A | R⁵-G | R⁶-E |
| E-182 | X-A | R²-M | R³-E | R⁵-G | R⁶-E |
| E-183 | X-A | R²-M | R³-A | R⁵-B | R⁶-G |
| E-184 | X-A | R²-M | R³-E | R⁵-B | R⁶-G |
| E-185 | X-A | R²-M | R³-A | R⁵-E | R⁶-G |
| E-186 | X-A | R²-M | R³-E | R⁵-E | R⁶-G |
| E-187 | X-A | R²-M | R³-A | R⁵-G | R⁶-G |
| E-188 | X-A | R²-M | R³-E | R⁵-G | R⁶-G |
| E-189 | X-A | R²-N | R³-A | R⁵-B | R⁶-B |
| E-190 | X-A | R²-N | R³-E | R⁵-B | R⁶-B |
| E-191 | X-A | R²-N | R³-A | R⁵-E | R⁶-B |
| E-192 | X-A | R²-N | R³-E | R⁵-E | R⁶-B |
| E-193 | X-A | R²-N | R³-A | R⁵-G | R⁶-B |
| E-194 | X-A | R²-N | R³-E | R⁵-G | R⁶-B |
| E-195 | X-A | R²-N | R³-A | R⁵-B | R⁶-E |
| E-196 | X-A | R²-N | R³-E | R⁵-B | R⁶-E |
| E-197 | X-A | R²-N | R³-A | R⁵-E | R⁶-E |
| E-198 | X-A | R²-N | R³-E | R⁵-E | R⁶-E |
| E-199 | X-A | R²-N | R³-A | R⁵-G | R⁶-E |
| E-200 | X-A | R²-N | R³-E | R⁵-G | R⁶-E |
| E-201 | X-A | R²-N | R³-A | R⁵-B | R⁶-G |
| E-202 | X-A | R²-N | R³-E | R⁵-B | R⁶-G |

-continued

| Embodiment | X | $R^2$ | $R^3$ | $R^5$ | $R^6$ |
|---|---|---|---|---|---|
| E-203 | X-A | $R^2$-N | $R^3$-A | $R^5$-E | $R^6$-G |
| E-204 | X-A | $R^2$-N | $R^3$-E | $R^5$-E | $R^6$-G |
| E-205 | X-A | $R^2$-N | $R^3$-A | $R^5$-G | $R^6$-G |
| E-206 | X-A | $R^2$-N | $R^3$-E | $R^5$-G | $R^6$-G |
| E-207 | X-A | $R^2$-O | $R^3$-A | $R^5$-B | $R^6$-B |
| E-208 | X-A | $R^2$-O | $R^3$-E | $R^5$-B | $R^6$-B |
| E-209 | X-A | $R^2$-O | $R^3$-A | $R^5$-E | $R^6$-B |
| E-210 | X-A | $R^2$-O | $R^3$-E | $R^5$-E | $R^6$-B |
| E-211 | X-A | $R^2$-O | $R^3$-A | $R^5$-G | $R^6$-B |
| E-212 | X-A | $R^2$-O | $R^3$-E | $R^5$-G | $R^6$-B |
| E-213 | X-A | $R^2$-O | $R^3$-A | $R^5$-B | $R^6$-E |
| E-214 | X-A | $R^2$-O | $R^3$-E | $R^5$-B | $R^6$-E |
| E-215 | X-A | $R^2$-O | $R^3$-A | $R^5$-E | $R^6$-E |
| E-216 | X-A | $R^2$-O | $R^3$-E | $R^5$-E | $R^6$-E |
| E-217 | X-A | $R^2$-O | $R^3$-A | $R^5$-G | $R^6$-E |
| E-218 | X-A | $R^2$-O | $R^3$-E | $R^5$-G | $R^6$-E |
| E-219 | X-A | $R^2$-O | $R^3$-A | $R^5$-B | $R^6$-G |
| E-220 | X-A | $R^2$-O | $R^3$-E | $R^5$-B | $R^6$-G |
| E-221 | X-A | $R^2$-O | $R^3$-A | $R^5$-E | $R^6$-G |
| E-222 | X-A | $R^2$-O | $R^3$-E | $R^5$-E | $R^6$-G |
| E-223 | X-A | $R^2$-O | $R^3$-A | $R^5$-G | $R^6$-G |
| E-224 | X-A | $R^2$-O | $R^3$-E | $R^5$-G | $R^6$-G |
| E-225 | X-A | $R^2$-P | $R^3$-A | $R^5$-B | $R^6$-B |
| E-226 | X-A | $R^2$-P | $R^3$-E | $R^5$-B | $R^6$-B |
| E-227 | X-A | $R^2$-P | $R^3$-A | $R^5$-E | $R^6$-B |
| E-228 | X-A | $R^2$-P | $R^3$-E | $R^5$-E | $R^6$-B |
| E-229 | X-A | $R^2$-P | $R^3$-A | $R^5$-G | $R^6$-B |
| E-230 | X-A | $R^2$-P | $R^3$-E | $R^5$-G | $R^6$-B |
| E-231 | X-A | $R^2$-P | $R^3$-A | $R^5$-B | $R^6$-E |
| E-232 | X-A | $R^2$-P | $R^3$-E | $R^5$-B | $R^6$-E |
| E-233 | X-A | $R^2$-P | $R^3$-A | $R^5$-E | $R^6$-E |
| E-234 | X-A | $R^2$-P | $R^3$-E | $R^5$-E | $R^6$-E |
| E-235 | X-A | $R^2$-P | $R^3$-A | $R^5$-G | $R^6$-E |
| E-236 | X-A | $R^2$-P | $R^3$-E | $R^5$-G | $R^6$-E |
| E-237 | X-A | $R^2$-P | $R^3$-A | $R^5$-B | $R^6$-G |
| E-238 | X-A | $R^2$-P | $R^3$-E | $R^5$-B | $R^6$-G |
| E-239 | X-A | $R^2$-P | $R^3$-A | $R^5$-E | $R^6$-G |
| E-240 | X-A | $R^2$-P | $R^3$-E | $R^5$-E | $R^6$-G |
| E-241 | X-A | $R^2$-P | $R^3$-A | $R^5$-G | $R^6$-G |
| E-242 | X-A | $R^2$-P | $R^3$-E | $R^5$-G | $R^6$-G |
| E-243 | X-A | $R^2$-Q | $R^3$-A | $R^5$-B | $R^6$-B |
| E-244 | X-A | $R^2$-Q | $R^3$-E | $R^5$-B | $R^6$-B |
| E-245 | X-A | $R^2$-Q | $R^3$-A | $R^5$-E | $R^6$-B |
| E-246 | X-A | $R^2$-Q | $R^3$-E | $R^5$-E | $R^6$-B |
| E-247 | X-A | $R^2$-Q | $R^3$-A | $R^5$-G | $R^6$-B |
| E-248 | X-A | $R^2$-Q | $R^3$-E | $R^5$-G | $R^6$-B |
| E-249 | X-A | $R^2$-Q | $R^3$-A | $R^5$-B | $R^6$-E |
| E-250 | X-A | $R^2$-Q | $R^3$-E | $R^5$-B | $R^6$-E |
| E-251 | X-A | $R^2$-Q | $R^3$-A | $R^5$-E | $R^6$-E |
| E-252 | X-A | $R^2$-Q | $R^3$-E | $R^5$-E | $R^6$-E |
| E-253 | X-A | $R^2$-Q | $R^3$-A | $R^5$-G | $R^6$-E |
| E-254 | X-A | $R^2$-Q | $R^3$-E | $R^5$-G | $R^6$-E |
| E-255 | X-A | $R^2$-Q | $R^3$-A | $R^5$-B | $R^6$-G |
| E-256 | X-A | $R^2$-Q | $R^3$-E | $R^5$-B | $R^6$-G |
| E-257 | X-A | $R^2$-Q | $R^3$-A | $R^5$-E | $R^6$-G |
| E-258 | X-A | $R^2$-Q | $R^3$-E | $R^5$-E | $R^6$-G |
| E-259 | X-A | $R^2$-Q | $R^3$-A | $R^5$-G | $R^6$-G |
| E-260 | X-A | $R^2$-Q | $R^3$-E | $R^5$-G | $R^6$-G |
| E-261 | X-A | $R^2$-R | $R^3$-A | $R^5$-B | $R^6$-B |
| E-262 | X-A | $R^2$-R | $R^3$-E | $R^5$-B | $R^6$-B |
| E-263 | X-A | $R^2$-R | $R^3$-A | $R^5$-E | $R^6$-B |
| E-264 | X-A | $R^2$-R | $R^3$-E | $R^5$-E | $R^6$-B |
| E-265 | X-A | $R^2$-R | $R^3$-A | $R^5$-G | $R^6$-B |
| E-266 | X-A | $R^2$-R | $R^3$-E | $R^5$-G | $R^6$-B |
| E-267 | X-A | $R^2$-R | $R^3$-A | $R^5$-B | $R^6$-E |
| E-268 | X-A | $R^2$-R | $R^3$-E | $R^5$-B | $R^6$-E |
| E-269 | X-A | $R^2$-R | $R^3$-A | $R^5$-E | $R^6$-E |
| E-270 | X-A | $R^2$-R | $R^3$-E | $R^5$-E | $R^6$-E |
| E-271 | X-A | $R^2$-R | $R^3$-A | $R^5$-G | $R^6$-E |
| E-272 | X-A | $R^2$-R | $R^3$-E | $R^5$-G | $R^6$-E |
| E-273 | X-A | $R^2$-R | $R^3$-A | $R^5$-B | $R^6$-G |
| E-274 | X-A | $R^2$-R | $R^3$-E | $R^5$-B | $R^6$-G |
| E-275 | X-A | $R^2$-R | $R^3$-A | $R^5$-E | $R^6$-G |
| E-276 | X-A | $R^2$-R | $R^3$-E | $R^5$-E | $R^6$-G |
| E-277 | X-A | $R^2$-R | $R^3$-A | $R^5$-G | $R^6$-G |
| E-278 | X-A | $R^2$-R | $R^3$-E | $R^5$-G | $R^6$-G |

Examples of most preferred compounds according to this invention are each single compound listed in the following Tables 1 and 2.

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

The compounds according to the present invention are inhibitors of the hepatitis C virus NS5B RNA-dependent RNA polymerase and thus may be used to inhibit replication of hepatitis C viral RNA.

A compound according to the present invention may also be used as a laboratory reagent or a research reagent. For example, a compound of the present invention may be used as positive control to validate assays, including but not limited to surrogate cell-based assays and in vitro or in vivo viral replication assays.

Compounds according to the present invention may also be used as probes to study the hepatitis C virus NS5B polymerase, including but not limited to the mechanism of action of the polymerase, conformational changes undergone by the polymerase under various conditions and interactions with entities which bind to or otherwise interact with the polymerase.

Compounds of the invention used as probes may be labelled with a label which allows recognition either directly or indirectly of the compound such that it can be detected, measured and quantified. Labels contemplated for use with the compounds of the invention include, but are not limited to, fluorescent labels, chemiluminescent labels, colorimetric labels, enzymatic markers, radioactive isotopes, affinity tags and photoreactive groups.

Compounds of the invention used as probes may also be labelled with an affinity tag whose strong affinity for a receptor can be used to extract from a solution the entity to which the ligand is attached. Affinity tags include but are not limited to biotin or a derivative thereof, a histidine polypeptide, a polyarginine, an amylose sugar moiety or a defined epitope recognizable by a specific antibody.

Furthermore, compounds of the invention used as probes may be labelled with a photoreactive group which is transformed, upon activation by light, from an inert group to a reactive species, such as a free radical. Photoreactive groups include but are not limited to photoaffinity labels such as benzophenone and azide groups.

Furthermore, a compound according to the present invention may be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

Pharmaceutical Composition

Compounds of the present invention may be administered to a mammal in need of treatment for hepatitis C viral infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

For oral administration, the compound, or a pharmaceutically acceptable salt or ester thereof, can be formulated in any orally acceptable dosage form including but not limited to aqueous suspensions and solutions, capsules or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.01 to about 200 milligrams per kilogram of body weight, with the preferred dose being about 0.1 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, α-, β-, δ-, ω-, and τ-interferons, while examples of class II interferons include, but are not limited to, γ-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085 (all by Boehringer Ingelheim), WO 02/060926, WO 03/053349, WO 03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune), WO 01/77113, WO 01/81325, WO 02/08187, WO 02/08198, WO 02/08244, WO 02/08256, WO 02/48172, WO 03/062228, WO 03/062265, WO 2005/021584, WO 2005/030796, WO 2005/058821, WO 2005/051980, WO 2005/085197, WO 2005/085242, WO 2005/085275, WO 2005/087721, WO 2005/087725, WO 2005/087730, WO 2005/087731, WO 2005/107745 and WO 2005/113581 (all by Schering); and the candidates VX-950 and SCH-503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 (all by Boehringer Ingelheim), WO 01/47883 (Japan Tobacco), WO 03/000254 (Japan Tobacco), WO 03/026587 (BMS), WO 03/101993 (Neogenesis), WO 2004/087714 (IRBM), WO 2005/012288 (Genelabs), WO 2005/014543 (Japan Tobacco), WO 2005/049622 (Japan Tobacco), and WO 2005/121132 (Shionogi), and the candidates HCV 796 (ViroPharma/Wyeth), R-1626 and R-1656 (Roche), XTL-2125 (XTL), VCH-759 (Virochem) and NM 283 (Idenix/Novartis).

Inhibitors of another target in the HCV life cycle include agents (compounds or biologicals) that are effective to inhibit the formation and/or replication of HCV other than by inhibiting the function of the HCV NS3 protease or HCV polymerase. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

HIV inhibitors include agents (compounds or biologicals) that are effective to inhibit the formation and/or replication of HIV. This includes but is not limited to agents that interfere with either host or viral mechanisms necessary for the formation and/or replication of HIV in a mammal. HIV inhibitors include, but are not limited to:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, capravirine, etravirine, rilpivirine and BILR 355);

protease inhibitors (including but not limited to ritonavir, tipranavir, saquinavir, nelfinavir, indinavir, amprenavir, fosamprenavir, atazanavir, lopinavir, VX-385 and TMC-114);

entry inhibitors including but not limited to CCR5 antagonists (including but not limited to maraviroc (UK-427, 857) and TAK-652), CXCR4 antagonists (including but not limited to AMD-11070), fusion inhibitors (including but not limited to enfuvirtide (T-20)) and others (including but not limited to BMS-488043);

integrase inhibitors (including but not limited to MK-0518, c-1605, BMS-538158 and GS 9137);

TAT inhibitors;

maturation inhibitors (including but not limited to PA-457); and immunomodulating agents (including but not limited to levamisole).

HAV inhibitors include agents (compounds or biologicals) that are effective to inhibit the formation and/or replication of HAV. This includes but is not limited to agents that interfere with either host or viral mechanisms necessary for the formation and/or replication of HAV in a mammal. HAV inhibitors include but are not limited to Hepatitis A vaccines.

HBV inhibitors include agents (compounds or biologicals) that are effective to inhibit the formation and/or replication of HBV in a mammal. This includes but is not limited to agents that interfere with either host or viral mechanisms necessary for the formation and/or replication of HBV in a mammal. HBV inhibitors include, but are not limited to, agents that inhibit the HBV viral DNA polymerase and HBV vaccines.

Therefore, according to one embodiment, the pharmaceutical composition of this invention additionally comprises a therapeutically effective amount of one or more antiviral agents.

A further embodiment provides the pharmaceutical composition of this invention wherein the one or more antiviral agent comprises at least one other anti-HCV agent.

According to a more specific embodiment of the pharmaceutical composition of this invention, the at least one other anti-HCV agent comprises at least one immunomodulatory agent.

According to another more specific embodiment of the pharmaceutical composition of this invention, the at least one other anti-HCV agent comprises at least one other inhibitor of HCV polymerase.

According to yet another more specific embodiment of the pharmaceutical composition of this invention, the at least one other anti-HCV agent comprises at least one inhibitor of HCV NS3 protease.

According to still another more specific embodiment of the pharmaceutical composition of this invention, the at least one other anti-HCV agent comprises at least one inhibitor of another target in the HCV life cycle.

Methodology and Synthesis

The synthesis of compounds of formula (I) according to this invention is conveniently accomplished following the general procedure outlined in Scheme 1 below wherein $R^2$, X, $R^3$, $R^5$ and $R^6$ are as defined herein. Further instruction is provided to one skilled in the art by the specific examples set out hereinbelow.

forth in the examples below, at any chemically convenient intermediate stage in the scheme.

The nitro group of intermediates (III) is reduced to an amino group under well-known conditions to provide intermediates of formula (IV), or their salts with acids such as hydrochloric acid. The $R^5$ group may be added to the amino group of intermediates of formula (IV) by a reductive amination reaction with an appropriately substituted aldehyde or ketone or suitable derivative thereof, followed by treatment with sodium triacetoxyborohydride, according to Abdel-Magid, A. F.; Carson, K. G.; Harris, B. D.; Maryanoff, C. A.;

Scheme 1:

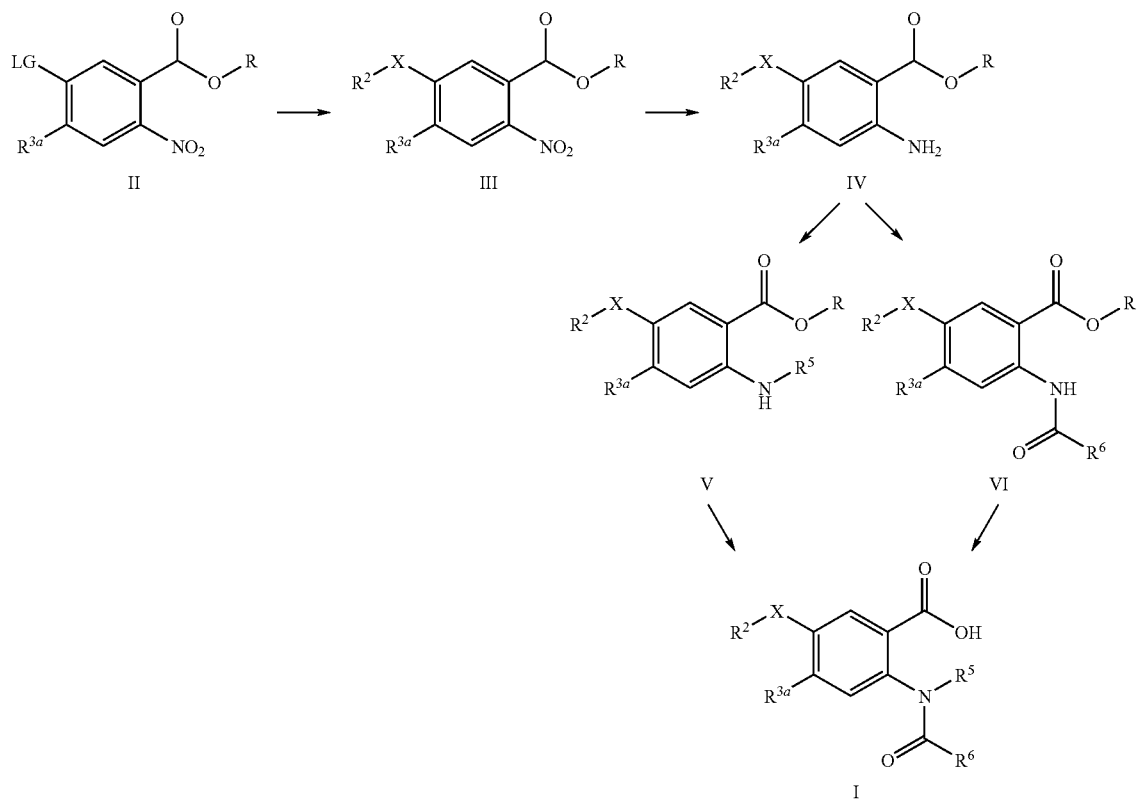

Intermediates of formula (II) wherein $R^{3a}$ is $R^3$ as defined herein or is a precursor group transformable to $R^3$ as defined herein, R is an ester protecting group, such as methyl or ethyl, and LG is a leaving group such as F or Cl, are commercially available or may be prepared by procedures well known in the art or as set forth in the examples below. It will be apparent to one skilled in the art that when the group $R^{3a}$ is a precursor group, it may be transformed to $R^3$ as defined herein at any chemically convenient intermediate stage in the scheme prior to formation of the compounds of formula (I), by procedures well known in the art or as set forth in the examples below.

Reaction of intermediates (II) with reactants of the formula $R^2X$—H, wherein $R^2$ and X are as defined herein, under $S_NAr$ reaction conditions well known to those skilled in the art, provides intermediates of formula (III). One skilled in the art will appreciate that $R^2$ groups of the compounds according to the invention differ in their substitution patterns and that it is contemplated that one $R^2$ group may be transformed to another $R^2$ group by procedures well known in the art or as set Shah, R. D. *J. Org. Chem.* 1996, 61, 3849, to provide intermediates of formula (V). Suitable derivatives of aldehydes and ketones are well known in the art and include, but are not limited to, enol ethers and the like. The aldehydes, ketones, or suitable derivatives thereof are commercially available or obtainable by procedures well known in the art or as set forth in the examples below. Intermediates (V) are acylated with appropriate acylating agents, which are commercially available or obtainable by procedures well known in the art or as set forth in the examples below. The ester protecting group R is then hydrolysed, by procedures well known in the art or as set forth in the examples below, to provide compounds of formula (I).

Alternatively, the amino group of intermediates of formula (IV) may be acylated as previously described to provide intermediates of formula (VI). Alkylation of the amide nitrogen atom of intermediates of formula (VI), by procedures well known in the art or as set forth in the examples below, followed by hydrolysis of the ester protecting group as previously described, provides compounds of formula (I).

One skilled in the art will appreciate that $R^5$ and $R^6$ groups of the compounds according to the invention differ in their substitution patterns and that it is contemplated that one $R^5$ group may be transformed to another $R^5$ group, or that one $R^6$ group may be transformed to another $R^6$ group, by procedures well known in the art or as set forth in the examples below, at any chemically convenient intermediate stage in the scheme.

Alternatively, the preparation of compounds of formula (I) may be accomplished by the procedure outlined in Scheme 2 below, wherein $R^2$, X, $R^3$, $R^5$ and $R^6$ are as defined herein, R is an ester protecting group such as methyl or ethyl and PG is a suitable protecting group for the XH functionality, well known to one skilled in the art, including but not limited to a benzyl group.

Scheme 2:

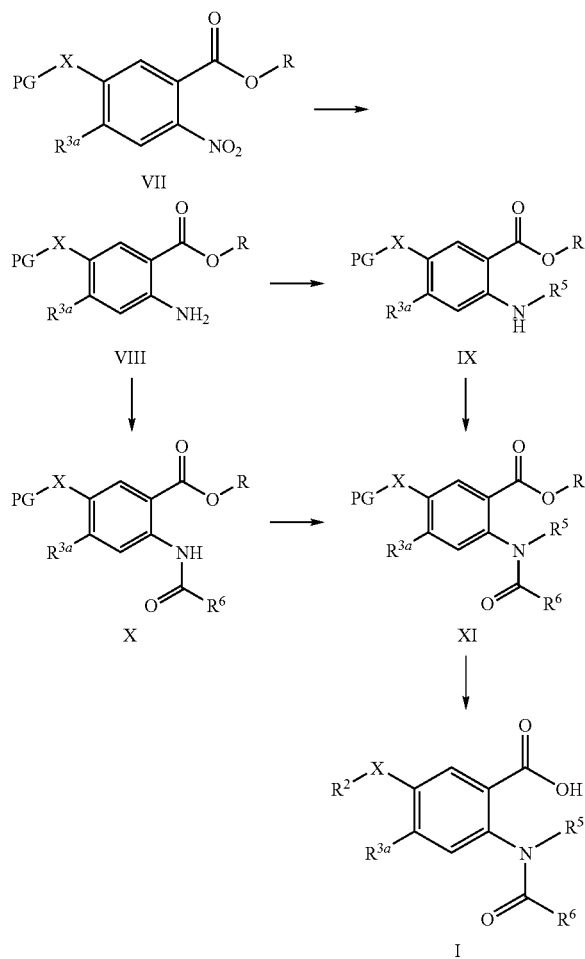

Intermediates of formula VII are commercially available or may be prepared by procedures well known in the art or as set forth in the examples below. Reduction of the nitro group to the amino group and introduction of the $R^5$ and —C(=O)$R^6$ groups is achieved as described above to give intermediates of formula (XI). The intermediates of formula (XI) are transformed to compounds of formula (I) by deprotecting the XH group by procedures well known in the art or as set forth in the examples below, coupling the resulting free phenol or thiol to a reactant of formula $R^2$-LG wherein LG is a leaving group such as F or Cl, using procedures well known in the art or as set forth in the examples below, and deprotecting the ester by hydrolysis as previously described.

EXAMPLES

Other features of the present invention will become apparent from the following non-limiting examples which illustrate, by way of example, the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923. Mass spectral analyses are recorded using electrospray mass spectrometry. Analytical HPLC is carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
| --- | --- | --- | --- |
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein include:
Ac: acetyl;
AcCl: acetyl chloride;
AcOH: acetic acid;
$Ac_2O$: acetic anhydride;
BINAP: 2,2'-bis(diphenylphosphino)-1,1'-binaphthyl;
Bn: benzyl (phenylmethyl);
BnBr: benzyl bromide;
BOC or Boc: tert-butyloxycarbonyl;
Bu: butyl;
DBU: 1,8-diazabicyclo[5.4.0]undec-7-ene;
DCM: dichloromethane;
DMAP: 4-dimethylaminopyridine;
DME: dimethoxyethane;
DMF: N,N-dimethylformamide;
DMSO: dimethylsulfoxide;
$EC_{50}$: 50% effective concentration;
EEDQ: 2-ethoxy-1-ethoxycarbonyl-1,2-dihydroquinoline;
Et: ethyl;
$Et_3N$: triethylamine;
$Et_2O$: diethyl ether;
EtOAc: ethyl acetate;
EtOH: ethanol;
HPLC: high performance liquid chromatography;
$IC_{50}$: 50% inhibitory concentration;
$_i$Pr or i-Pr: 1-methylethyl (iso-propyl);
Me: methyl;
MeCN: acetonitrile;
MeI: iodomethane;
MeOH: methanol;

MS: mass spectrometry (MALDI-TOF: Matrix Assisted Laser Desorption Ionization-Time of Flight, FAB: Fast Atom Bombardment);
NIS: N-iodosuccinamide;
NMR: nuclear magnetic resonance spectroscopy;
Ph: phenyl;
PG: protecting group;
Pr: propyl;
RT: room temperature (approximately 18° C. to 25° C.);
TBTU: O-benzotriazol-1-yl-N,N,N',N'-tetramethyluronium tetrafluoroborate;
tert-butyl or t-butyl: 1,1-dimethylethyl;
TFA: trifluoroacetic acid;
THF: tetrahydrofuran;
TLC: thin layer chromatography.

Example 1

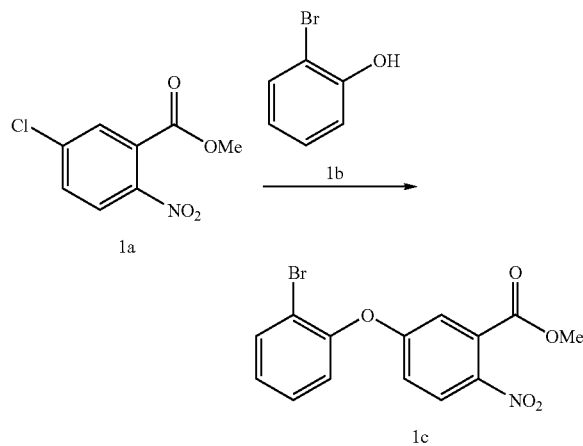

A mixture of methyl 5-chloro-2-nitrobenzoate 1a (2.27 g, 10.5 mmol), K$_2$CO$_3$ (2.19 g, 15.8 mmol) and 2-bromophenol 1b (1.83 mL, 15.8 mmol) in dry DMSO (30 mL) is heated to 80° C. After stirring overnight at 80° C., the mixture is diluted in EtOAc and washed with water and brine. The organic phase is dried with MgSO$_4$, filtered and concentrated under reduced pressure. Purification by flash chromatography (EtOAc/Hex) affords diarylether 1c.

Other intermediates of formula (III) wherein X is O and R$^{3a}$ is H are prepared using the procedure of Example 1 by replacing 2-bromophenol with other appropriately substituted phenols.

Example 2

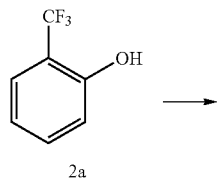

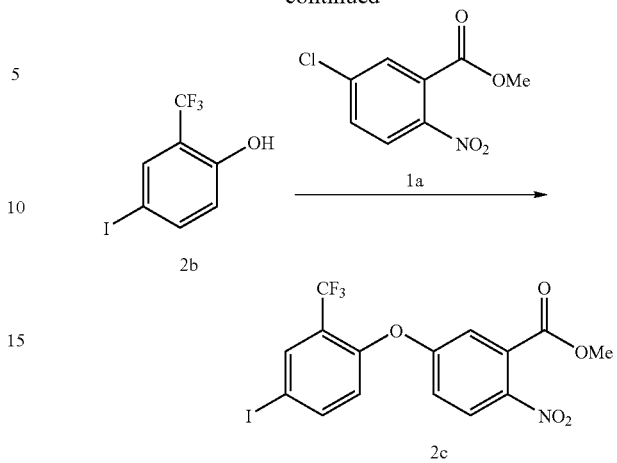

To 2-trifluoromethylphenol 2a (5.04 g, 31.1 mmol) in DMF (50 mL) is added NIS (7.0 g, 31.1 mmol). The reaction mixture is stirred overnight at ambient temperature then poured into 700 mL of water. The mixture is extracted three times with EtOAc and the combined organic extracts are successively washed with 10% aqueous Na$_2$S$_2$O$_3$, water (3×) and brine. The organic phase is dried with MgSO$_4$, filtered and concentrated under reduced pressure. Purification by flash chromatography (EtOAc/Hex) affords iodide 2b.

A mixture of methyl 5-chloro-2-nitrobenzoate 1a (Example 1) (750 mg, 3.5 mmol), K$_2$CO$_3$ (720 mg, 5.2 mmol) and phenol 2b (1.0 g, 3.5 mmol) in dry DMSO (8 mL) is heated to 95° C. The mixture is allowed to stir 7.5 hours at 95° C., then at room temperature overnight, then is added to saturated aqueous NH$_4$Cl. The mixture is extracted three times with EtOAc and the combined organic extracts are washed with water and brine. The organic phase is dried with MgSO$_4$, filtered and concentrated under reduced pressure. Purification by flash chromatography (8% EtOAc/Hex) affords diarylether 2c.

Example 3

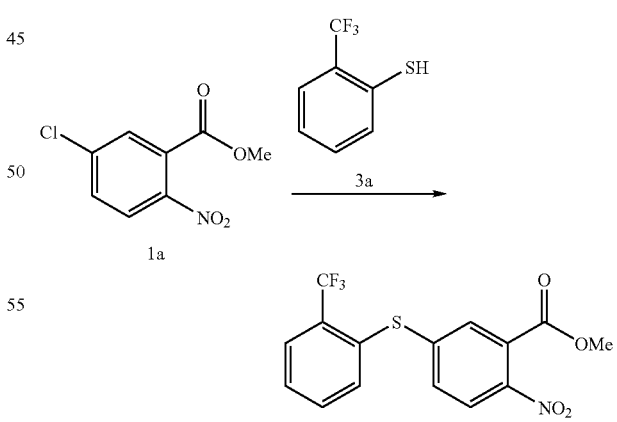

A mixture of methyl 5-chloro-2-nitrobenzoate 1a (Example 1) (1.08 g, 5.0 mmol), K$_2$CO$_3$ (0.90 g, 6.5 mmol) and 2-trifluoromethylthiophenol 3a (1.07 g, 6.0 mmol) in dry DMSO (10 mL) is stirred at ambient temperature for 1 hour. The mixture is diluted with EtOAc and washed with 1N HCl, water, 1N NaOH and brine. The organic phase is dried with MgSO$_4$, filtered and concentrated under reduced pressure. Purification by flash chromatography (EtOAc/Hex) affords diarylthioether 3b.

Other intermediates of formula (III) wherein X is S and R$^{3a}$ is H may be prepared using the procedures of Example 3 by replacing 2-trifluoromethylthiophenol with appropriately substituted thiophenols.

Example 4

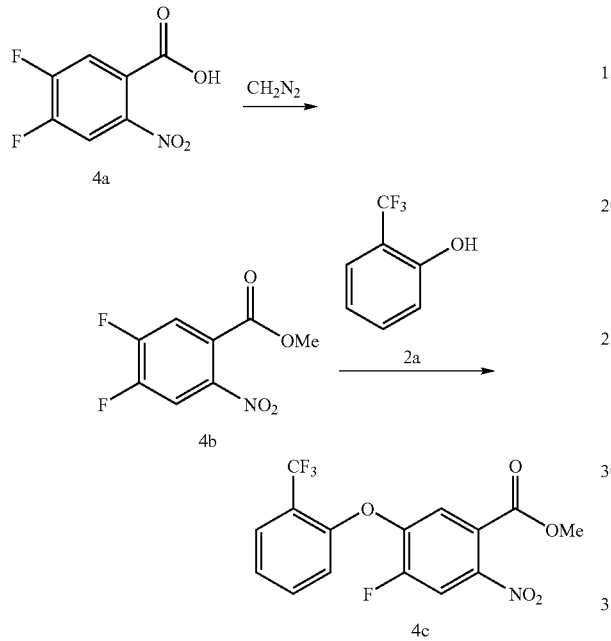

Excess of a solution of CH$_2$N$_2$ in Et$_2$O (100 mL) is added to a mixture of acid 4a (2.0 g, 10 mmol), MeOH (15 mL) and EtOAc (50 mL) at 0° C. The mixture is allowed to stir for 10 minutes then concentrated under reduced pressure, providing the ester 4b.

2-Trifluoromethylphenol 2a (Example 2) (973 mg, 6.0 mmol) is added to a mixture of K$_2$CO$_3$ (967 mg, 7.0 mmol) and anhydrous DMSO (10 mL) and the mixture is heated at 65° C. for 30 minutes. To this mixture is added a mixture of ester 4b (1.1 g, 5.0 mmol) and DMSO (4 mL) and heating is continued at 65° C. for 1 hour. The mixture is cooled to room temperature, diluted with EtOAc (60 mL) and Et$_2$O (30 mL), and washed with 1N HCl, water, 1N NaOH and brine. The organic extract is dried (MgSO$_4$) and concentrated under reduced pressure. The residue is purified by flash chromatography (10% EtOAc/hexane) to afford compound 4c.

Example 5

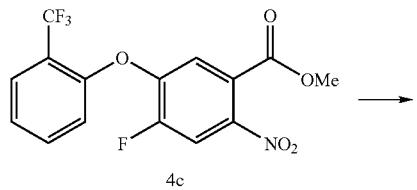

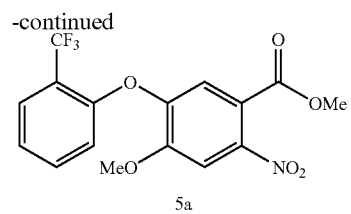

To a solution of the fluoroarene 4c (Example 4) (0.36 g, 1.0 mmol) in DMSO (5 mL) in a screw cap sealed tube is added NaOCH$_3$ (1M solution in MeOH, 1.5 mL, 1.5 mmol). The mixture is heated to 65° C. and stirred overnight, then allowed to cool to ambient temperature. The mixture is diluted with EtOAc and washed with 1N aqueous HCl, water and brine. The organic phase is dried with MgSO$_4$, filtered and concentrated under reduced pressure. Purification by flash chromatography (EtOAc/Hex) affords compound 5a.

Example 6

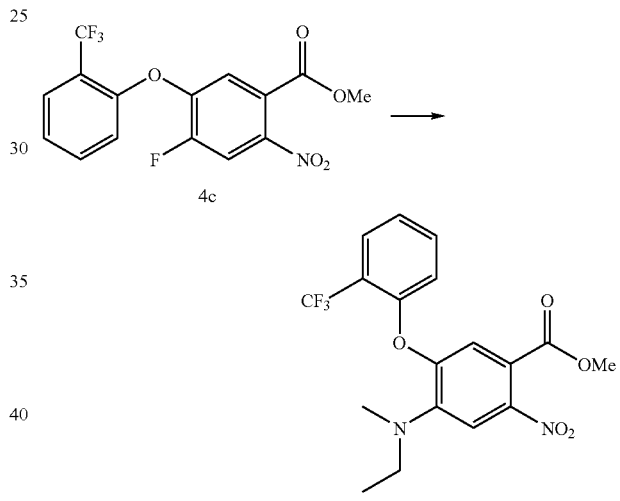

To a solution of the fluoroarene 4c (Example 4) (0.27 g, 0.8 mmol) in DMSO (5 mL) in a screw cap sealed tube is added CH$_3$CH$_2$NHCH$_3$ (0.11 mL, 1.1 mmol). The mixture is stirred overnight at ambient temperature, then diluted with EtOAc and washed with saturated aqueous NaHCO$_3$, water and brine. The organic phase is dried with MgSO$_4$, filtered and concentrated under reduced pressure. Purification by flash chromatography (EtOAc/Hex) affords 6a.

Example 7

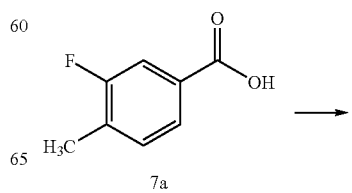

-continued

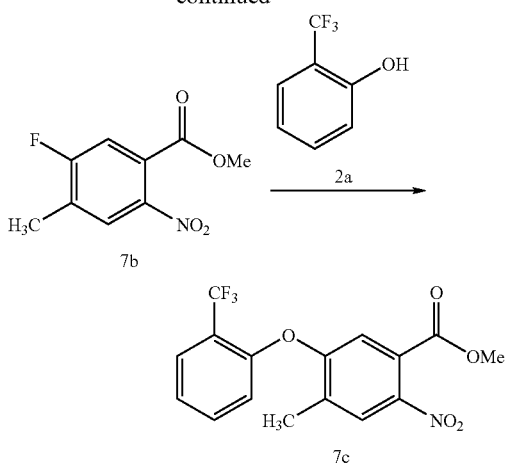

To 3-fluoro-4-methylbenzoic acid 7a (0.55 g, 3.6 mmol) in concentrated H$_2$SO$_4$ (3 mL) at 0° C. is added KNO$_3$ (0.36 g, 3.6 mmol). The mixture is stirred at 0° C. for 30 minutes then poured into MeOH (15 mL). The mixture is refluxed for 24 h, then allowed to cool to ambient temperature and concentrated under reduced pressure. The residue is dissolved in EtOAc and successively washed with water (2×), saturated aqueous NaHCO$_3$, water (2×) and brine. The organic phase is dried (MgSO$_4$), filtered and concentrated under reduced pressure to afford the nitroarene 7b.

Compound 7b is allowed to react with 2-trifluoromethylphenol 2a (Example 2) using the method described in Example 1, to give compound 7c.

Intermediates of formula (III) wherein R$_{3a}$ is Br are prepared using the method of Example 7 but replacing 3-fluoro-4-methylbenzoic acid 7a with 4-bromo-3-fluorobenzoic acid.

Example 8

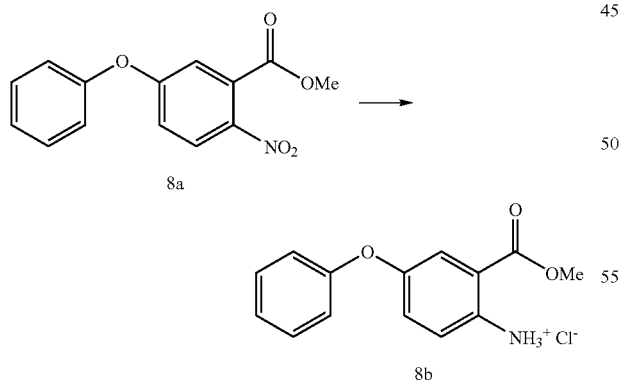

Nitroarene 8a (prepared from phenol and compound 1a using the method of Example 1) (1.26 g, 4.6 mmol) is combined with 10% palladium on carbon (0.1 g) in methanol (20 mL). The mixture is shaken under a hydrogen atmosphere for 1 hour then filtered through a pad of Celite™. The solution is concentrated under reduced pressure then is dissolved in Et$_2$O (35 mL). Hydrogen chloride in Et$_2$O (1 N, 15 mL, 15 mmol) is added slowly. Filtration of the resulting solid provides intermediate 8b.

Example 9

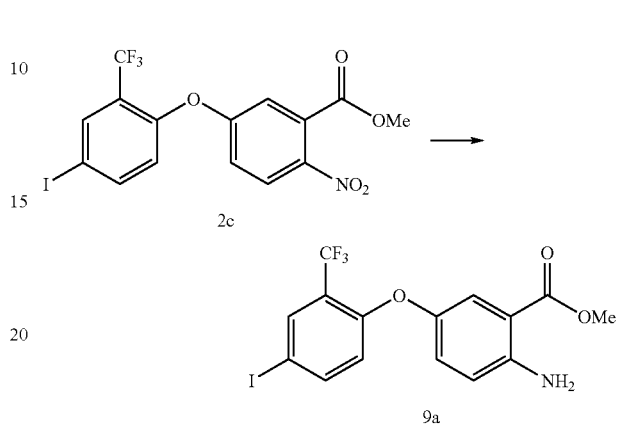

To a mixture of nitroarene 2c (Example 2) (0.88 g, 1.9 mmol) in methanol (140 mL) is added SnCl$_2$.2H$_2$O (4.25 g, 18.8 mmol) and the mixture is heated at reflux for 2 hours. After concentration, the residue is taken up in EtOAc and poured onto saturated aqueous NH$_4$Cl. The aqueous layer is extracted twice more with EtOAc and the combined organic extracts are filtered through a short pad of silica gel. After concentration, the residue is purified by flash chromatography (15% EtOAc-hexane) to afford the desired aniline 9a.

Example 10

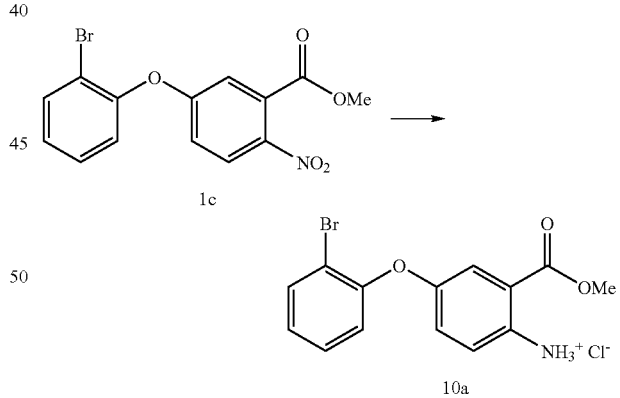

To a mixture of nitroarene 1c (Example 1) (1.26 g, 3.6 mmol) and ethanol (15 mL) is added saturated aqueous NH$_4$Cl (2 mL), water (2 mL) and Fe powder (0.60 g, 10.8 mmol) and the mixture is stirred 4 hours at 80° C. The mixture is diluted in EtOAc and washed with saturated aqueous NaHCO$_3$ and brine and the combined organic phase is dried with MgSO$_4$, filtered, and concentrated under reduced pressure. The residue is dissolved in Et$_2$O and is treated with 1N HCl in Et$_2$O (5.4 mL, 5.39 mmol) to provide the hydrochloride salt 10a which is recovered by filtration.

Other intermediates of formula (IV) are prepared from the appropriate intermediates of formula (III) using the procedures of Examples 8, 9 and/or 10.

Example 11

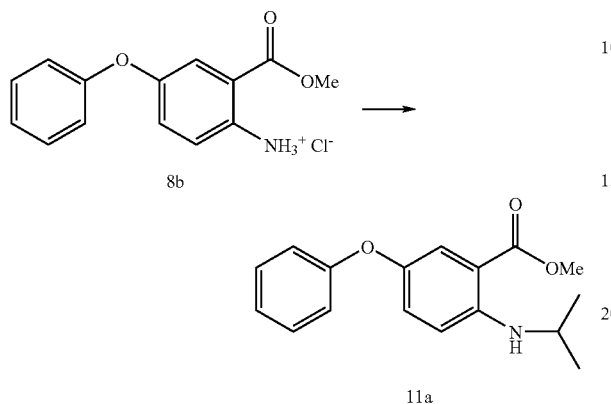

Compound 8b (Example 8) (663 mg, 2.4 mmol) is suspended in CH$_2$Cl$_2$ (15 mL) and 2-methoxypropene (908 µL, 9.5 mmol) is added, followed by NaBH(OAc)$_3$ (1.0 g, 4.7 mmol). The reaction mixture is allowed to stir at room temperature overnight, then is diluted with EtOAc and washed with NaHCO$_3$ and brine. The organic phase is dried over MgSO$_4$, filtered and concentrated under reduced pressure. The residue is purified by flash chromatography (5% EtOAc/hexane) to give compound 11a.

Example 12

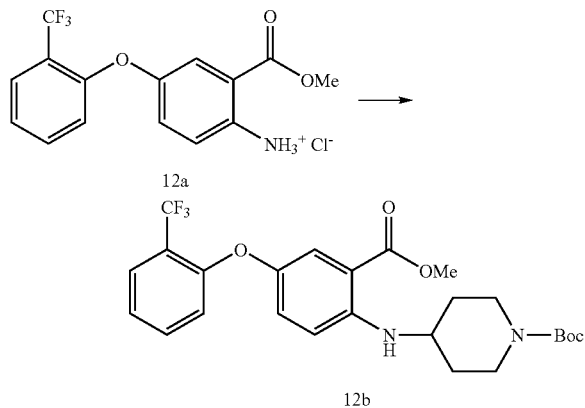

Compound 12a (prepared from 2-trifluoromethylphenol 2a using the methods of Examples 1 and 8) (278 mg, 0.80 mmol) is suspended in anhydrous CH$_2$Cl$_2$ (6 mL) under nitrogen atmosphere and 1-tert-butyloxycarbonyl-4-piperidone (319 mg, 1.60 mmol) is added followed by Ti(OMe)$_4$ (275 mg, 4.60 mmol). The mixture is heated at 80° C. for 5 h, NaBH(OAc)$_3$ (339 mg, 1.60 mmol) is added and the mixture is heated at 80° C. overnight. The mixture is cooled to room temperature, diluted with EtOAc and washed with saturated NaHCO$_3$, water and brine. The organic extract is dried over MgSO$_4$ and concentrated under reduced pressure. The residue is purified by flash chromatography (25% EtOAc/hexane) to provide compound 12b.

Other intermediates of formula (V) are prepared from the appropriate intermediates of formula (IV) using the procedures of Examples 11 and/or 12 and appropriate aldehydes, ketones or suitable derivatives thereof.

Example 13

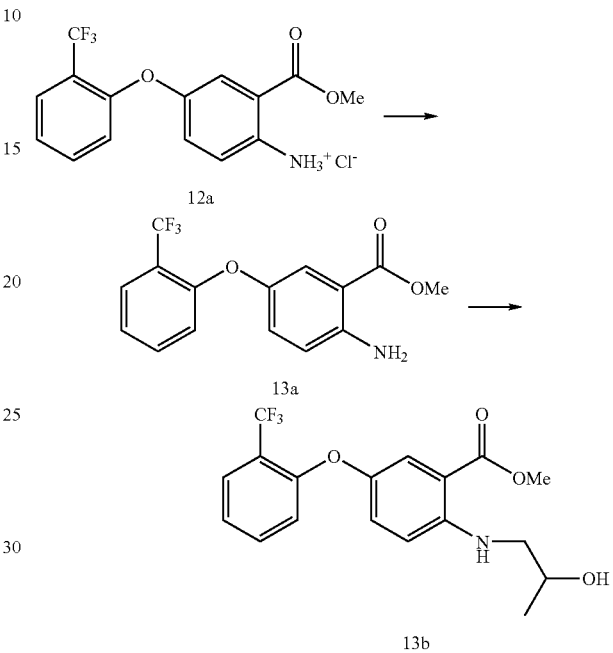

To a solution of compound 12a (Example 12) (300 mg, 0.86 mmol) in EtOAc (50 mL) is added saturated aqueous NaHCO$_3$ (6.0 mL). The layers are separated and the organic layer is washed with water and brine, then dried (MgSO$_4$) and concentrated under reduced pressure to give compound 13a.

The procedure used in the second step is adapted from: Chandrasekhar, S.; RamaChandar, T.; Jaya Prakash, S *Synthesis* 2000, 1817. Compound 13a (0.052 g, 0.17 mmol) is combined with anhydrous CH$_2$Cl$_2$ (6 mL), propylene oxide (0.058 mL, 0.84 mmol), silica gel (0.01 g) and TaCl$_5$ (0.063 g, 0.18 mmol). The mixture is stirred at ambient temperature for 60 hours, then filtered through Celite™, diluted with EtOAc and washed with 1N HCl, water, saturated NaHCO$_3$ and brine. The organic extract is dried over MgSO$_4$ and concentrated under reduced pressure to provide compound 13b.

Example 14

Preparation of Compound 1008 (Table 1):

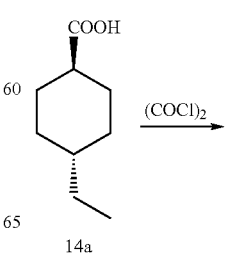

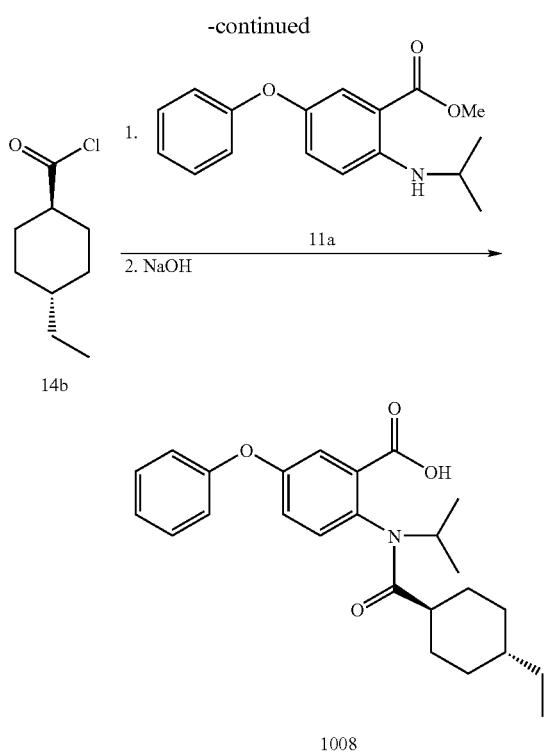

To a mixture of carboxylic acid 14a (1.00 g, 6.4 mmol) and CH$_2$Cl$_2$ (10 mL) under an N$_2$ atmosphere is added oxalyl chloride (2M in CH$_2$Cl$_2$, 6.4 mL, 12.87 mmol) followed by a drop of DMF. The solution is stirred for 3 hours at ambient temperature, then concentrated under reduced pressure. The residue is diluted in pentanes (~2 mL) and filtered. The solution is concentrated, and the residue is diluted in pentanes and concentrated to afford acid chloride 14b.

Acid chloride 14b (87 mg, 0.5 mmol) is added to a solution of aniline 11a (Example 11) (0.03 g, 0.1 mmol) in pyridine (0.5 mL). The mixture is warmed to 60° C. and stirred overnight. Aqueous sodium hydroxide (10N, 0.15 mL, 1.5 mmol) and water (0.15 mL) are added and stirring is continued overnight at 50° C. The mixture is diluted in EtOAc and washed with 1N aqueous HCl and brine and the organic phase is dried with MgSO$_4$, filtered and concentrated under reduced pressure. The residue is dissolved in DMSO and purified by preparative HPLC to provide compound 1008 (Table 1).

Example 15

Preparation of Compound 1039 (Table 1):

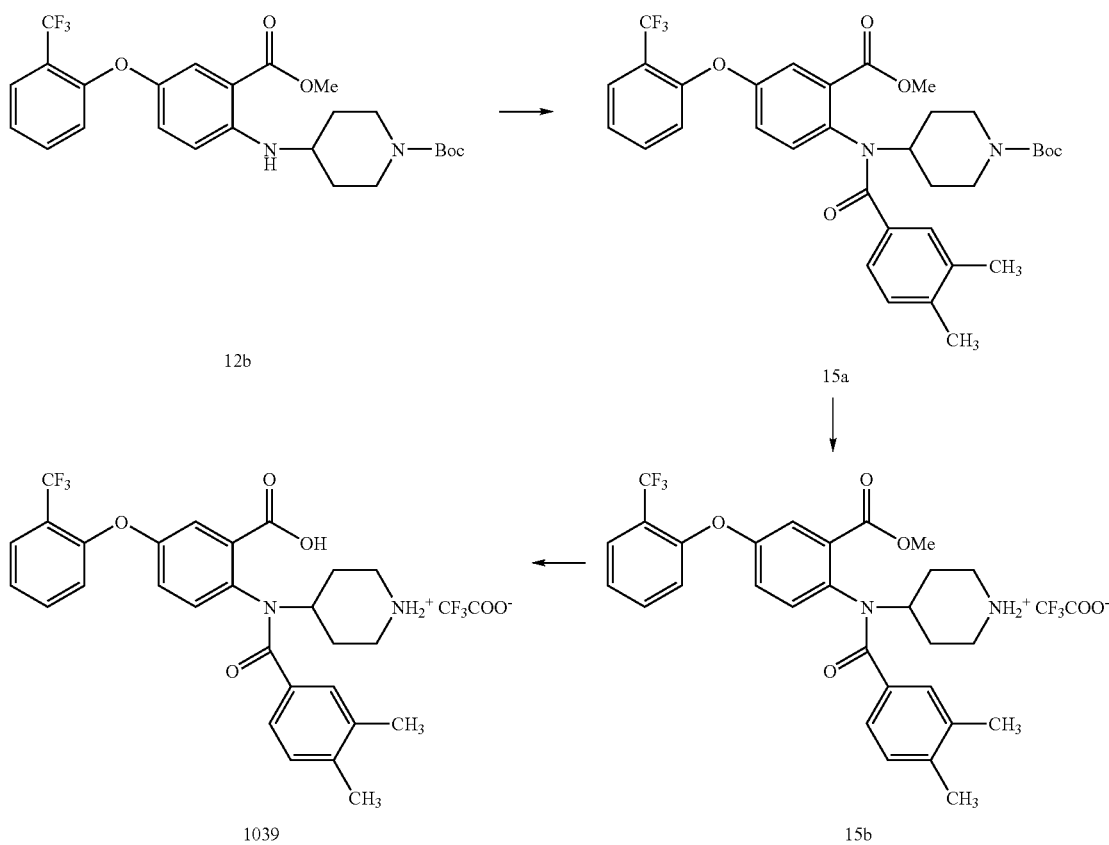

To a solution of compound 12b (Example 12) (100 mg, 0.20 mmol) in anhydrous pyridine (6 mL) is added 3,4-dimethylbenzoyl chloride (50.6 mg, 0.30 mmol) and DMAP (35 mg, 0.29 mmol). The reaction mixture is stirred overnight at 60° C., then cooled to room temperature and diluted with EtOAc (50 mL). The mixture is washed sequentially with 1N HCl, water, 1N NaOH, water and brine, then dried (MgSO$_4$), filtered and concentrated under reduced pressure. The residue is purified by flash chromatography to provide compound 15a. Trifluoroacetic acid (0.5 mL) is added to a mixture of compound 15a (64 mg, 0.1 mmol) and CH$_2$Cl$_2$ (0.5 mL) and the mixture is stirred at ambient temperature for 1 hour. Concentration under reduced pressure affords compound 15b as the trifluoroacetate salt.

To a solution of compound 15b (21.6 mg, 0.03 mmol) in THF (0.70 mL) and MeOH (0.30 mL) is added 10N NaOH (30 μL, 0.30 mmol) and the mixture is allowed to stir at room temperature for 2 days. The mixture is acidified with TFA (28 μL, 0.36 mmol) and concentrated under reduced pressure. The residue is dissolved in DMSO and purified by preparative HPLC to provide compound 1039 (Table 1) as the trifluoroacetate salt.

Other compounds of formula (I) are prepared from the appropriate intermediates of formula (V) using the procedures of Examples 13 and/or 14 and/or the first and last steps of Example 15 and appropriate acylating agents.

Example 16

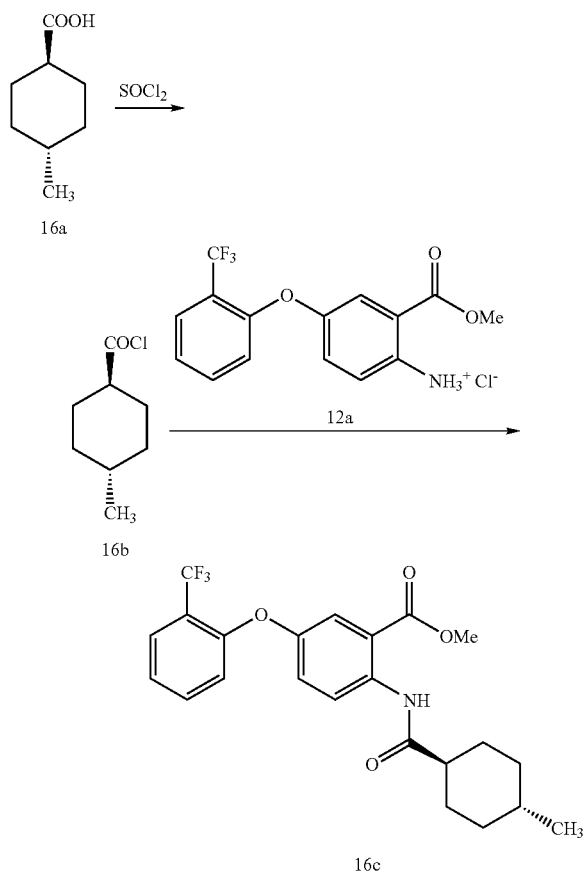

A mixture of thionyl chloride (7.7 mL, 105 mmol) and acid 16a (5.0 g, 35 mmol) is heated at 80° C. for 1 hour. Concentration of the mixture under reduced pressure provides acid chloride 16b.

Acid chloride 16b (361 mg, 2.25 mmol) is added slowly to a solution of compound 12a (Example 12) (521 mg, 1.50 mmol) in anhydrous pyridine (10 mL) at 60° C. and the mixture is stirred at 60° C. for 15 minutes. The mixture is cooled to room temperature, diluted with EtOAc (75 mL) and washed with 1N HCl, water, 1N NaOH, water and brine. The organic phase is dried over MgSO$_4$, filtered and concentrated under reduced pressure to afford compound 16c.

Other intermediates of formula (VI) are prepared from the appropriate intermediates of formula (IV) using the procedures of Example 16 and appropriate acylating agents.

Example 17

Preparation of Compound 2063 (Table 2):

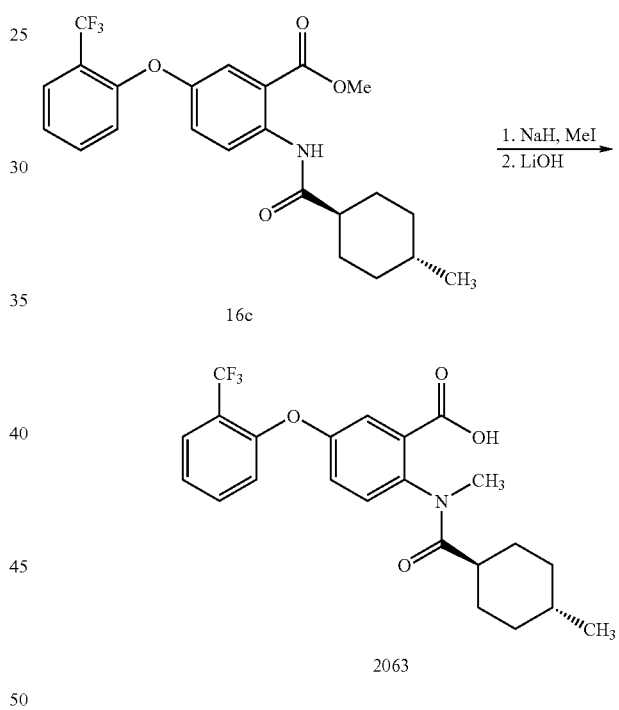

To a mixture of compound 16c (Example 16) (50 mg, 0.12 mmol) and anhydrous DMF (2.0 mL) is added NaH (4.2 mg, 0.17 mmol) and the mixture is stirred at room temperature for 5 minutes. MeI (38 μL, 0.58 mmol) is added and stirring is continued for 1.5 hours. To the mixture is added H$_2$O (0.5 mL), MeOH (1.0 mL) and 5N LiOH (400 μL) and stirring is continued at room temperature for 1 hour. The mixture is acidified with TFA, concentrated and purified by preparative HPLC to afford compound 2063 (Table 2).

Other compounds of formula (I) are prepared from the appropriate intermediates of formula (VI) using the procedures of Example 17 and appropriate alkylating agents. When the alkylating agent is tert-butyl 2-bromoacetate, the intermediate ester may be deprotected by treatment with an acid, such as trifluoroacetic acid, under well-known conditions.

Example 18

Preparation of Compound 1040 (Table 1):

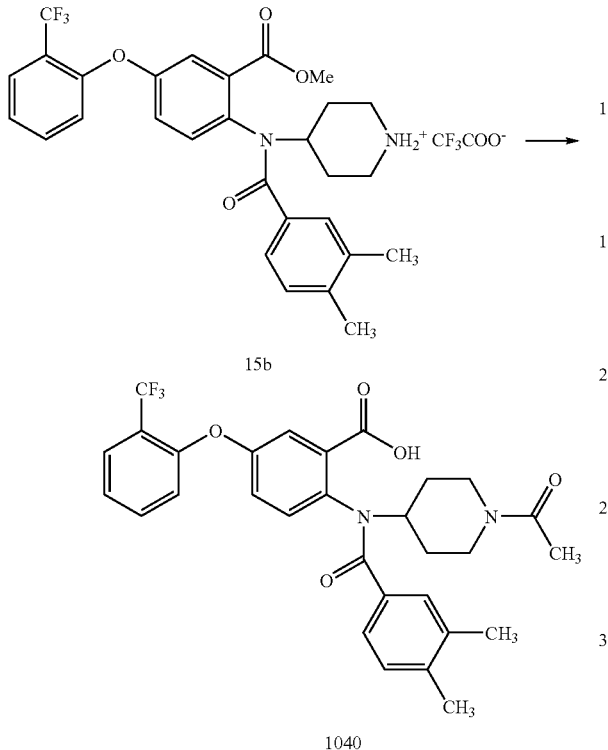

To a solution of compound 15b (Example 15) (27 mg, 0.04 mmol) in THF (0.7 mL) is added Ac₂O (0.02 mL, 0.20 mmol), Et₃N (0.017 mL, 0.12 mmol) and DMAP (1 mg, cat.) and the mixture is stirred at ambient temperature for 1 hour. Aqueous NaOH (10N, 0.06 mL, 0.6 mmol) is added and the mixture is stirred overnight. The mixture is acidified with TFA (0.062 mL, 0.8 mmol) and concentrated under reduced pressure. The residue is dissolved in DMSO (1 mL) and purified by preparative HPLC to afford compound 1040 (Table 1).

Example 19

Preparation of Compound 1041 (Table 1):

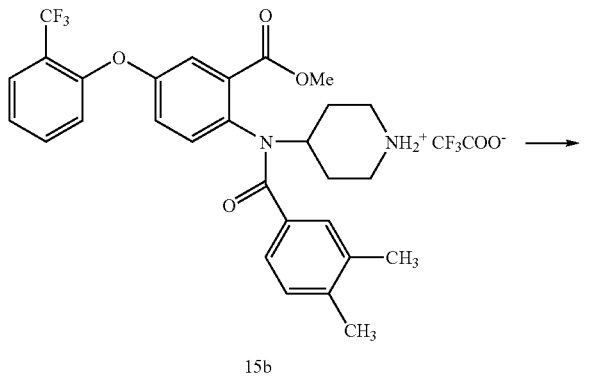

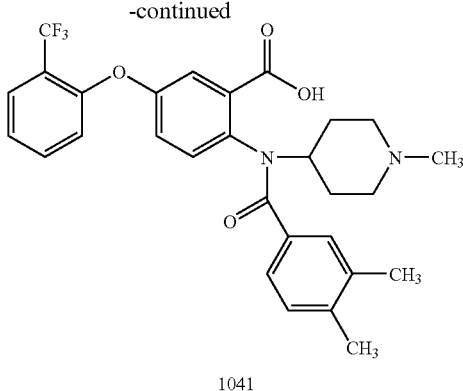

To a solution of compound 15b (0.036 g, 0.6 mmol) in EtOH (0.7 mL) is added HCHO (37% aqueous solution, 0.024 mL, 0.3 mmol), NaBH₃CN (0.023 g, 0.36 mmol) and AcOH (0.055 mL, 0.1 mmol). The mixture is stirred overnight at ambient temperature, then diluted in EtOAc and washed with saturated aqueous NaHCO₃, and brine. The organic phase is dried with MgSO₄, filtered and concentrated under reduced pressure. The residue is dissolved in THF/MeOH (4:1; 1 mL), aqueous NaOH (10N, 0.06 mL, 0.6 mmol) is added and the solution is stirred 60 hours at ambient temperature. The reaction is acidified with TFA (0.055 mL, 0.7 mmol) and concentrated under reduced pressure. The residue is dissolved in DMSO and purified by preparative HPLC to afford compound 1041 (Table 1).

Example 20

Preparation of Compound 2059 (Table 2):

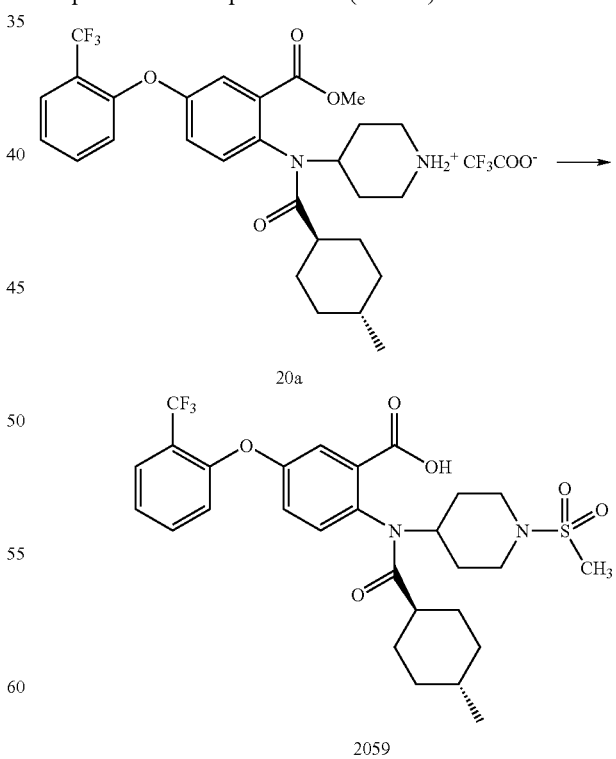

To a solution of compound 20a (prepared from compound 12b (Example 12) using the method of Example 15, but replacing 3,4-dimethylbenzoyl chloride with compound 16b (Example 16)) (30 mg, 0.05 mmol) in DMSO (2 mL) is added CH₃SO₂Cl (0.006 mL, 0.07 mmol) and Et₃N (0.067 mL, 0.46 mmol) and the mixture is stirred at ambient temperature for 30 minutes. Aqueous LiOH (5N, 0.45 mL, 2.3 mmol) and MeOH (1 mL) are added and the mixture is warmed to 50° C. and stirred for 1 hour. The MeOH is removed under reduced pressure and the mixture is acidified with TFA (0.23 mL, 3 mmol), filtered and purified by preparative HPLC to afford compound 2059 (Table 2).

Example 21

Preparation of Compound 2060 (Table 2):

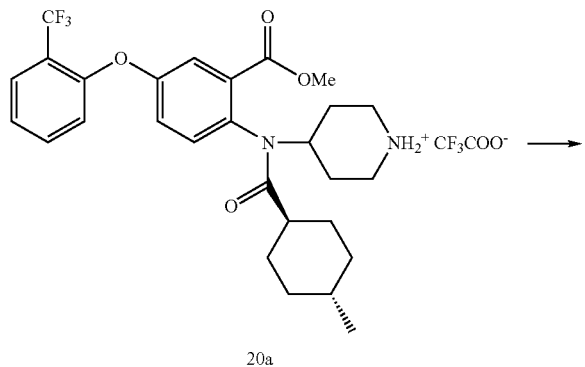

20a

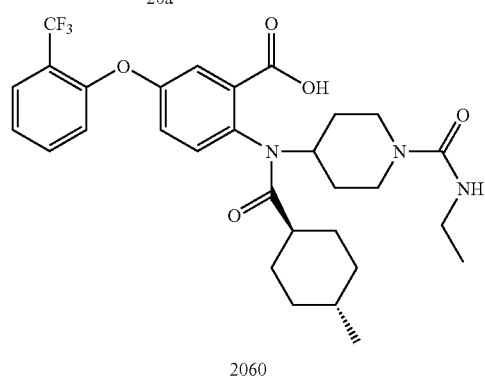

2060

To a solution of compound 20a (Example 20) (30 mg, 0.05 mmol) in DMSO (2 mL) is added Et-N=C=O (0.007 mL, 0.09 mmol) and Et₃N (0.067 mL, 0.46 mmol) and the mixture is stirred at ambient temperature for 1 hour. Aqueous LiOH (5N, 0.45 mL, 2.3 mmol) and MeOH (1 mL) are added and the mixture is warmed to 50° C. and stirred for 1 hour. The MeOH is removed under reduced pressure and the mixture is acidified with TFA (0.23 mL, 3 mmol), filtered and purified by preparative HPLC to afford compound 2060 (Table 2).

Example 22

Preparation of Compound 2061 (Table 2):

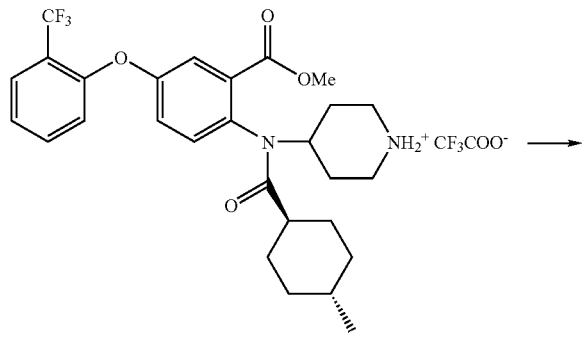

20a

-continued

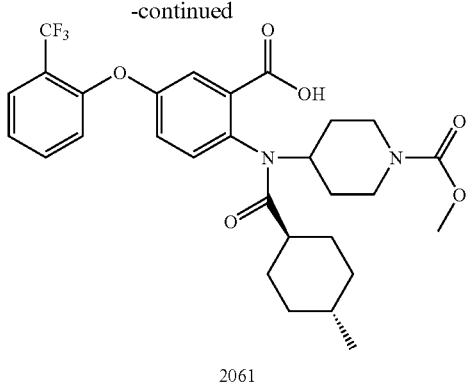

2061

To a solution of compound 20a (Example 20) (30 mg, 0.05 mmol) in DMSO (2 mL) is added methyl chloroformate (0.013 mL, 0.16 mmol) and Et₃N (0.066 mL, 0.46 mmol) and the mixture is stirred at ambient temperature for 30 minutes. Aqueous LiOH (5N, 0.45 mL, 2.3 mmol) and MeOH (1 mL) are added and the mixture is warmed to 55° C. and stirred for 2 hours. The MeOH is removed under reduced pressure and the mixture is acidified with TFA (0.23 mL, 3 mmol), filtered and purified by preparative HPLC to afford compound 2061 (Table 2).

Example 23

Preparation of Compound 2022 (Table 2):

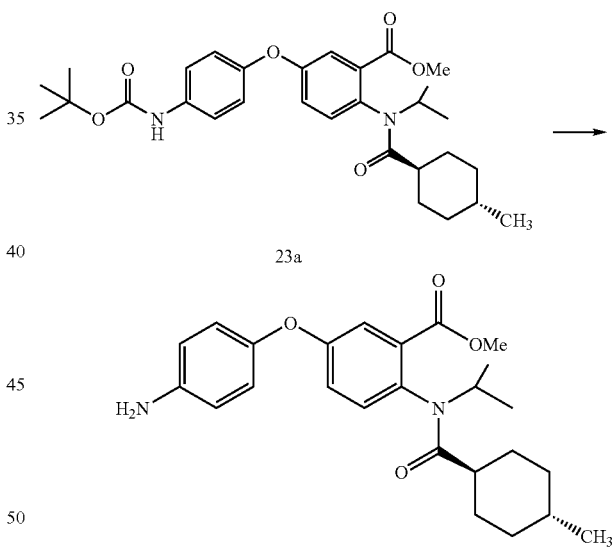

Compound 23a is prepared by using the method of Example 1, but replacing 2-bromophenol with 4-aminophenol; protecting the amino group of the corresponding compound of formula (III) as a tert-butyloxycarbamate, by treatment with $Boc_2O$ and $NaHCO_3$ using procedures well known in the art; and transforming the protected compound of formula (III) to compound 23a using the procedures of Examples 8, 11 and 14, but replacing compound 14b with compound 16b.

To a solution of compound 23a (0.51 g, 0.97 mmol) in $CH_2Cl_2$ (2 mL) is added TFA (2 mL).

The mixture is stirred at ambient temperature for 1 hour, then concentrated under reduced pressure. The residue is triturated in $Et_2O$ and the solid is isolated by filtration affording compound 23b as the trifluoroacetate salt.

To a solution of compound 23b (0.045 mg, 0.08 mmol) in pyridine (3 mL) is added AcCl (0.036 mL, 0.50 mmol). The mixture is stirred at 55° C. for 15 minutes and allowed to cool to ambient temperature, then diluted with EtOAc and washed with 1N HCl, water, 1N NaOH and brine. The organic phase is dried with $MgSO_4$, filtered and concentrated under reduced pressure. The residue is dissolved in DMSO/MeOH (2:1, 3.0 mL) followed by the addition of aqueous LiOH (5N, 0.4 mL, 2.0 mmol). The mixture is stirred at 55° C. for 1 hour and allowed to cool to ambient temperature. TFA (0.030 mL, 0.4 mmol) is added and the mixture is concentrated. Purification of the residue by preparative HPLC affords compound 2022 (Table 2).

It will be apparent to one skilled in the art that compound 23a is transformed to compound 2018 of Table 2 by hydrolysis using the method of the last step of Example 15. Likewise, compound 23b is converted to compound 2019 of Table 2, using the hydrolysis method of the last step of Example 15. Compound 23b is also used to synthesize urea derivatives such as compounds 2025 and 2026 of Table 2 using procedures described in Thavonekham, B. *Synthesis* 1997, 1189.

Example 24

Preparation of Compound 2015 (Table 2):

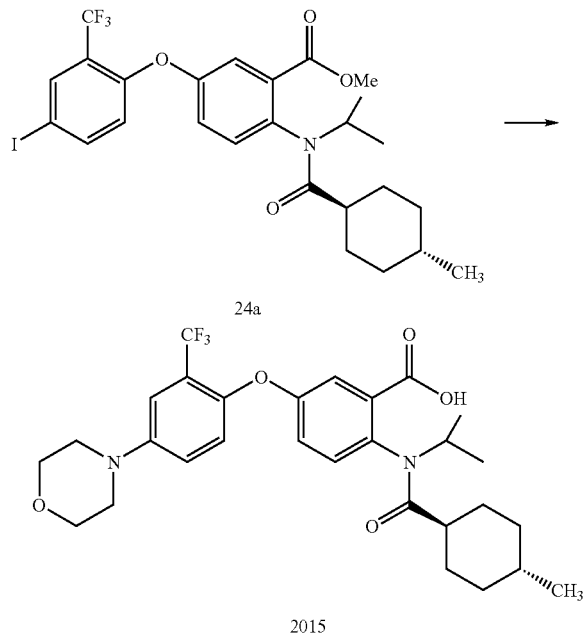

Compound 24a is prepared from compound 9a (Example 9) using the methods of Examples 11 and 14, but replacing compound 14b with compound 16b (Example 16).

A mixture of racemic BINAP (0.011 g, 2 μmol) and $Pd(OAc)_2$ (4 mg, 2 μmol) is sonicated for 10 minutes in dry toluene (1.5 mL). This mixture is combined with a mixture of compound 24a (0.10 g, 0.17 mmol), morpholine (0.020 mL, 0.22 mmol) and $Cs_2CO_3$ (0.28 g, 0.85 mmol) in dry toluene (6.5 mL) and the resulting mixture is stirred at 110° C. for 16 h. The mixture is allowed to cool to ambient temperature and filtered through Celite™. The filtrate is concentrated under reduced pressure and the residue dissolved in DMSO (1.50 mL). Aqueous NaOH (10N, 0.17 mL, 1.7 mmol) is added and the mixture is warmed to 50° C. and allowed to stir for 1 hour. The mixture is acidified with TFA (0.16 mL, 2.0 mmol) and purified by preparative HPLC to provide compound 2015 (Table 2).

Other compounds of formula (I) wherein $R_2$ is a phenyl group bearing a cyclic or acyclic amine group at the 4-position are prepared using the method of Example 24 but replacing morpholine with an appropriate amine.

Example 25

Preparation of Compound 2074 (Table 2):

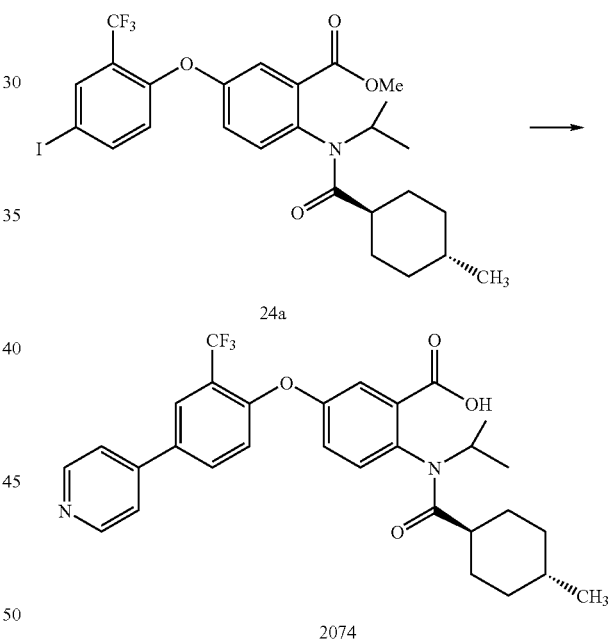

To a solution of compound 24a (Example 24) (0.025 g, 0.04 mmol) in DMF (0.5 mL) are successively added 4-pyridyl boronic acid (0.007 g, 0.06 mmol), 2M aqueous $Na_2CO_3$ (0.082 mL, 0.16 mmol) and bis-(tri-tert-butylphosphino)palladium (0.002 mg, 10 mol %). The mixture is heated at 125° C. for 8 min in a microwave (Biotage Initiator™ Sixty). DMSO (0.3 mL) and 5N aqueous NaOH (0.82 mL, 0.41 mmol) are added and the mixture is stirred at 50° C. for 30 min. The mixture is acidified with AcOH then purified by preparative HPLC to afford compound 2074 (Table 2).

Compounds 2075, 2076 and 2077 of Table 2 are also prepared using the method of Example 25 but replacing 4-pyridyl boronic acid with an appropriate boronic acid.

Example 26

Preparation of Compound 2087 (Table 2):

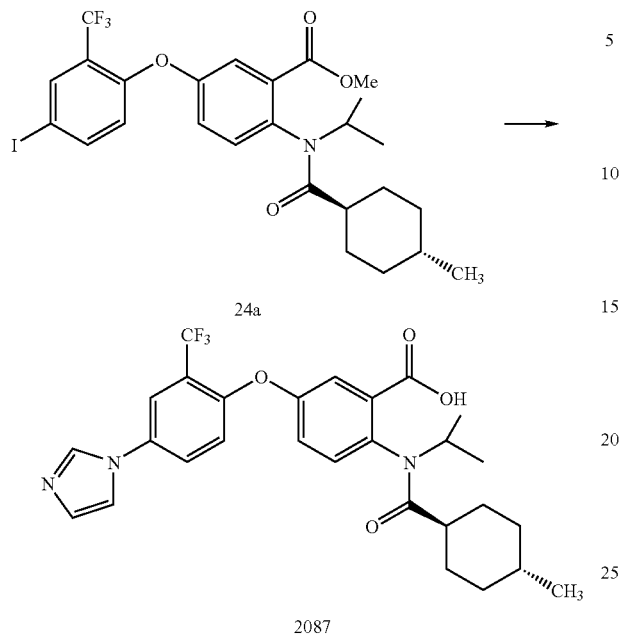

The procedure is adapted from: Antilla, J. C.; Baskin, J. M.; Barder, T. E.; Buchwald, S. W. *J. Org. Chem.* 2004, 69, 5578.

A mixture of compound 24a (Example 24) (21.7 mg, 0.036 mmol), imidazole (2.5 mg, 0.037 mmol), cesium carbonate (24.0 mg, 0.074 mmol), copper (I) iodide (1.8 mg, 0.009 mmol), DMF (1.0 mL) and trans-N,N-dimethyl-1,2-cyclohexanediamine (3.0 mg, 0.021 mmol) under $N_2$ atmosphere is heated overnight at 100° C. Aqueous NaOH (5N, 0.072 mL, 0.36 mmol) is added and the mixture is heated at 55° C. for 30 min. then quenched with AcOH. The mixture is purified using a semi-preparative LC-MS system to afford compound 2087 (Table 2).

Compounds 2089 to 2102 of Table 2 are also prepared using the method of Example 26 but replacing imidazole with an appropriate heterocycle.

Example 27

Preparation of Compound 2064 (Table 2):

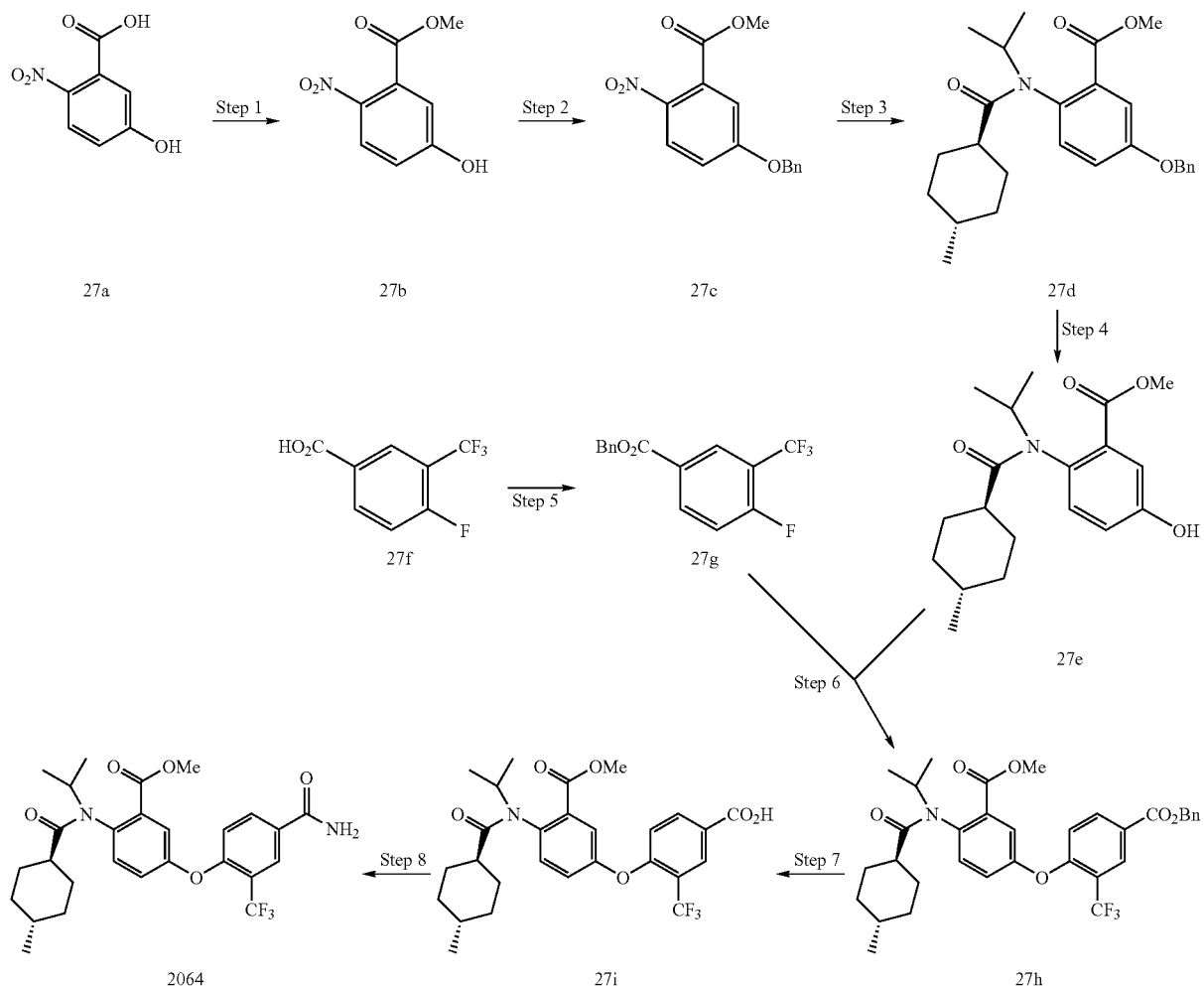

Step 1:

A mixture of carboxylic acid 27a (5.0 g, 27 mmol) and concentrated H₂SO₄ (4 mL) in MeOH (80 mL) is stirred at reflux for 12 hours. The mixture is concentrated under reduced pressure and poured onto a mixture of ice and saturated aqueous NaHCO₃. The aqueous mixture is acidified with citric acid and extracted twice with EtOAc. The combined organic extracts are washed with water and brine, dried with MgSO₄, filtered, and concentrated under reduced pressure. Purification by flash chromatography (3:7 EtOAc/Hexane) affords ester 27b.

Step 2:

To a solution of phenol 27b (4.30 g, 22 mmol) in acetone (50 mL) is added K₂CO₃ (12.1 g, 87 mmol), followed by BnBr (3.1 mL, 26 mmol). The mixture is stirred 72 hours at ambient temperature, then diluted with EtOAc and washed with water and brine. The organic phase is dried with MgSO₄, filtered and concentrated under reduced pressure to afford the benzyl ether 27c.

Step 3:

Compound 27c is converted into amide 27d using the methods of Examples 10, 11 and 14, but replacing compound 14b with compound 16b (Example 16).

Step 4:

Pd/C (10%, 0.035 g) is added to a solution of benzyl ether 27d (0.35 g, 0.83 mmol) in MeOH/EtOAc (2:5, 14 mL). The mixture is stirred at ambient temperature for 5 h under 1 atm of H₂, then filtered through Celite™. The filtrate is concentrated under reduced pressure and the resulting residue is triturated with Et₂O/hexanes. Filtration of the solid affords the desired phenol 27e.

Step 5:

A mixture of carboxylic acid 27f (1.00 g, 4.8 mmol), DBU (0.86 mL, 5.8 mmol) and BnBr (0.63 mmol, 5.3 mmol) in MeCN (10 mL) is stirred at ambient temperature for 16 hours. The mixture is diluted with EtOAc and washed with 1N HCl, 1N NaOH and brine. The organic phase is dried with MgSO₄, filtered and concentrated in vacuo to afford the benzyl ester 27g.

Step 6:

A mixture of phenol 27e (Step 4) (1.17 g, 3.5 mmol), fluoroarene 27g (Step 5) (1.15 g, 3.9 mmol) and K₂CO₃ (1.21 g, 8.8 mmol) in DMSO (11 mL) is stirred at 100° C. for 2 hours. The mixture is diluted with aqueous citric acid and the resulting solid is collected by filtration, washed with water, and dried. Purification by flash chromatography affords compound 27h.

Step 7:

A mixture of benzyl ester 27h (3.5 mmol) and 10% Pd/C (0.11 g) in EtOAc is stirred under 1 atm of H₂ for 16 hours. The mixture is filtered and the filtrate is concentrated under reduced pressure to afford carboxylic acid 27i.

Step 8:

A mixture of carboxylic acid 27i (0.025 g, 0.05 mmol), NH₄HCO₃ (0.015 g, 0.19 mmol) and EEDQ (0.018 g, 0.07 mmol) in CHCl₃ (1 mL) is stirred for 16 hours at ambient temperature. The CHCl₃ is removed under reduced pressure and DMSO (1 mL) is added to the residue followed by aqueous NaOH (10N, 0.050 mL, 0.50 mmol). The mixture is stirred at 55° C. for 60 hours, then purified by preparative HPLC to afford compound 2064 (Table 2).

Example 28

Preparation of Compound 2065 (Table 2):

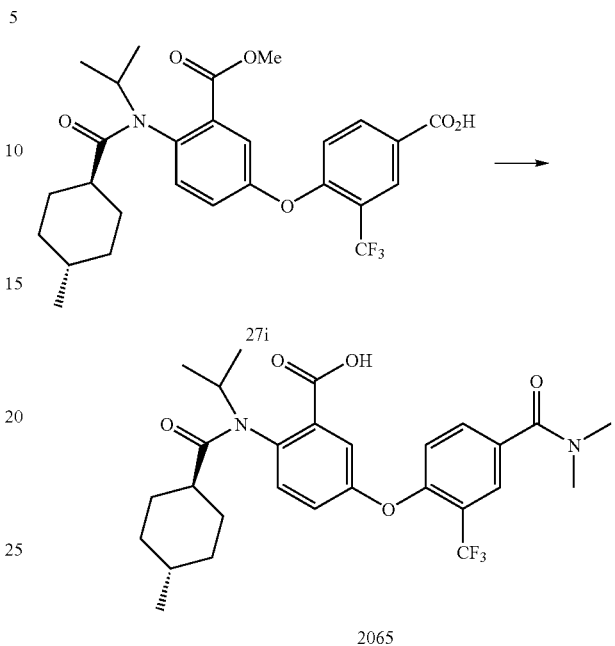

A mixture of carboxylic acid 27i (Example 27) (0.025 g, 0.05 mmol), (CH₃)₂NH.HCl (0.005 g, 0.06 mmol) and TBTU (0.019 g, 0.06 mmol) in DMSO (1 mL) is stirred for 2 hours at ambient temperature and aqueous NaOH (10N, 0.050 mL, 0.50 mmol) and water (0.2 mL) are added. The mixture is warmed to 55° C. and stirred for 60 hours, then purified by preparative HPLC to afford compound 2065 (Table 2).

Example 29

Preparation of Compound 2081 (Table 2):

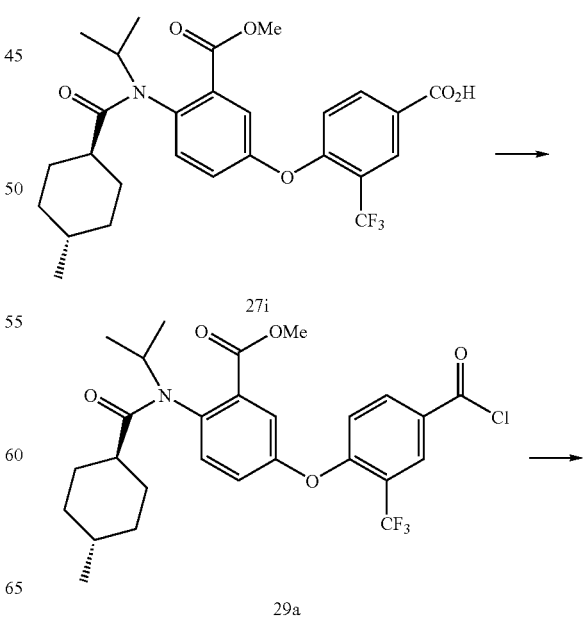

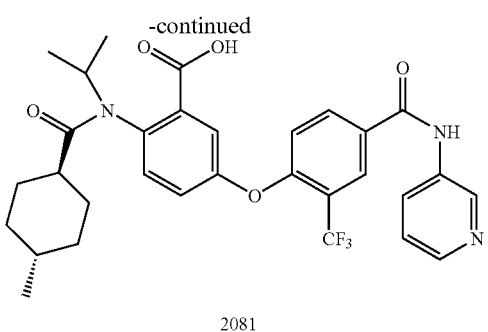

2081

A mixture of carboxylic acid 27i (Example 27) (101 mg, 0.194 mmol), SOCl$_2$ (1.0 mL, 13.7 mmol) and DMF (10 µL) is allowed to stir at room temperature for 1 h. The reaction mixture was concentrated under reduced pressure, CH$_2$Cl$_2$ was added to the residue and the mixture was again concentrated under reduced pressure to give the acid chloride 29a.

A mixture of acid chloride 29a (26 mg, 0.048 mmol), 3-aminopyridine (5.5 mg, 0.058 mmol) and Et$_3$N (9.0 µL, 0.065 mmol) in CH$_2$Cl$_2$ (1.0 mL) is allowed to react at 70° C. overnight. The mixture is concentrated under reduced pressure and to the residue is added NaOH (10N, 50 µL, 0.50 mmol), DMSO (0.5 mL) and water (50 µL). The mixture is heated at 55° C. for 1 h, acidified with AcOH and purified by preparative HPLC to give compound 2081 (Table 2).

Other compounds of formula (I) wherein R$^2$ is a phenyl group bearing an amide group at the 4-position are prepared using the methods of Example 28 or 29 but replacing (CH$_3$)$_2$NH.HCl or 3-aminopyridine with an appropriate amine or amine salt.

Example 30

Preparation of Compound 2071 (Table 2):

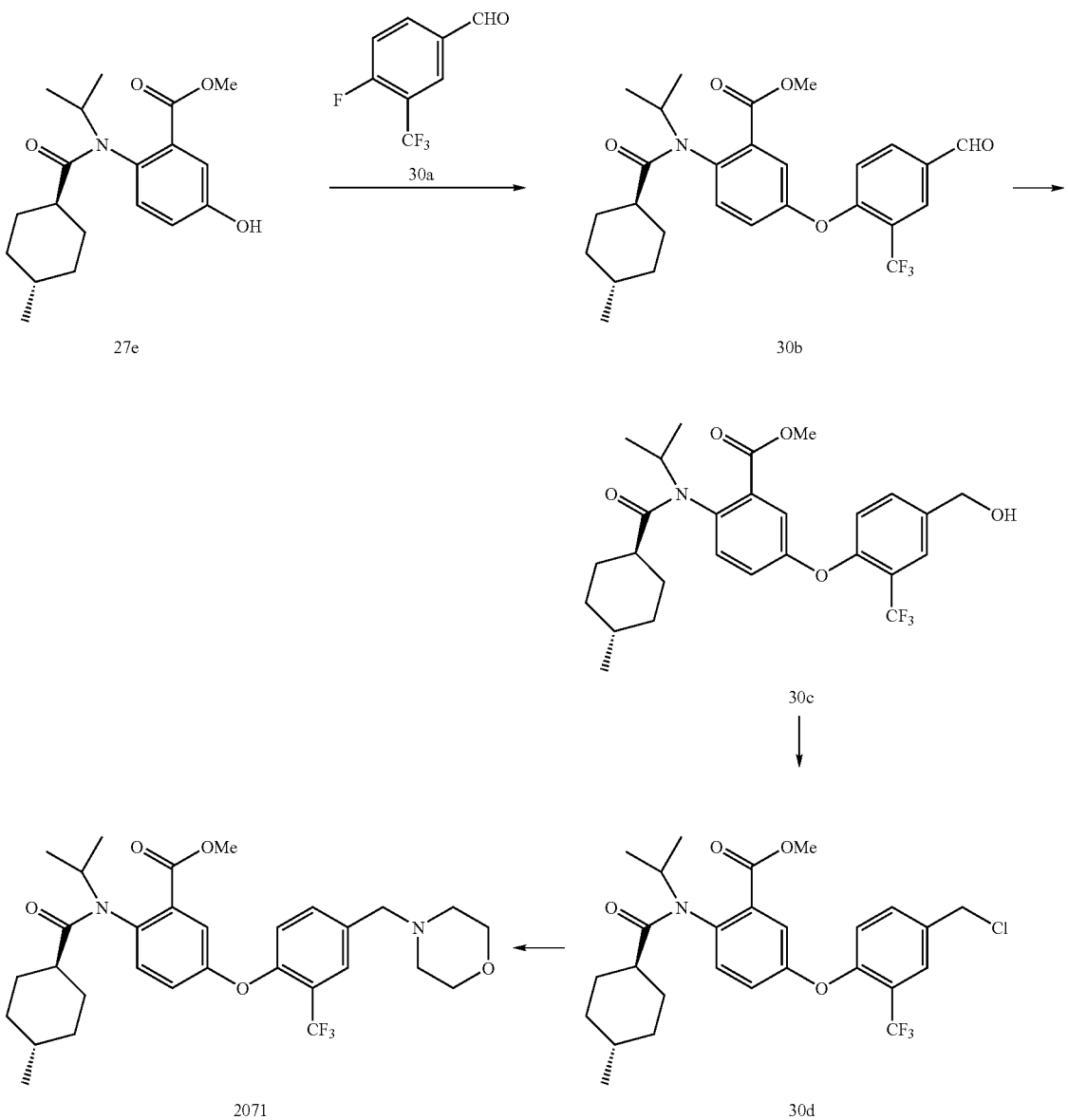

A mixture of phenol 27e (Example 27) (0.50 g, 1.5 mmol), fluoroarene 30a (0.35 g, 1.8 mmol) and K₂CO₃ (0.52 g, 3.8 mmol) in DMSO (10 mL) is stirred at 100° C. for 45 minutes. The mixture is diluted with saturated aqueous citric acid and the resulting solid is collected by filtration, washed with water then dried to afford compound 30b.

A mixture of aldehyde 30b (0.30 g, 0.6 mmol) and NaBH₄ (0.5M in Et₂O, 1.4 mL, 0.71 mmol) in MeOH (10 mL) is stirred for 1 hour, then concentrated under reduced pressure. The residue is diluted with concentrated aqueous citric acid and extracted twice with EtOAc. The combined organic extracts are washed with brine, dried with MgSO₄, filtered and concentrated under reduced pressure to afford alcohol 30c.

To a mixture of alcohol 30c (0.31 g, 0.6 mmol) in CH₂Cl₂ (3 mL) are added DMF (0.03 mL) and SOCl₂ (0.059 mL, 0.8 mmol). The mixture is stirred for 15 minutes and concentrated under reduced pressure. The residue is diluted with water and extracted twice with EtOAc. The combined organic extracts are washed with water and brine, dried with MgSO₄, filtered and concentrated under reduced pressure to afford compound 30d.

A mixture of compound 30d (0.025 g, 0.05 mmol), morpholine (0.005 mL, 0.06 mmol) and Et₃N (0.01 mL, 0.07 mmol) in THF (1 mL) is stirred at 65° C. for 1 day. Morpholine (0.005 mL, 0.06 mmol) and KI (0.03 g, 0.02 mmol) are added and stirring is continued at 65° C. for an additional day. The solution is concentrated under reduced pressure and to the residue is added DMSO (0.5 mL), aqueous NaOH (10N, 0.1 mL, 1.0 mmol) and water (0.1 mL). The mixture is stirred 1 hour at 55° C., then acidified with AcOH and purified by preparative HPLC to afford compound 2071 (Table 2).

Compound 30c is transformed to compound 2135 (Table 2) by hydrolysis with 10N NaOH as described in the last step of Example 30.

Example 31

Preparation of Compound 2085 (Table 2):

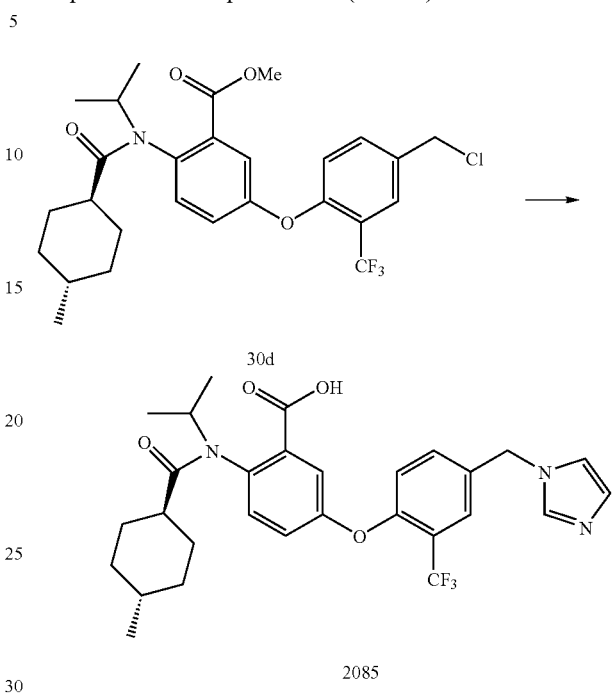

A mixture of compound 30d (Example 30) (25 mg, 0.048 mmol), imidazole (3.9 mg, 0.058 mmol), Cs₂CO₃ (19 mg, 0.058 mmol) and KI (0.80 mg, 0.005 mmol) in DMF (0.50 mL) is allowed to react at 70° C. overnight. The mixture is concentrated under reduced pressure and to the residue is added NaOH (10N, 50 μL, 0.50 mmol), DMSO (0.5 mL) and water (50 μL). The mixture is heated at 55° C. for 1 h, acidified with AcOH and purified by preparative HPLC to give compound 2085 (Table 2).

Compound 2086 (Table 2) is prepared by the method of Example 31 but replacing imidazole with pyrazole.

Example 32

Preparation of Compound 2073 (Table 2):

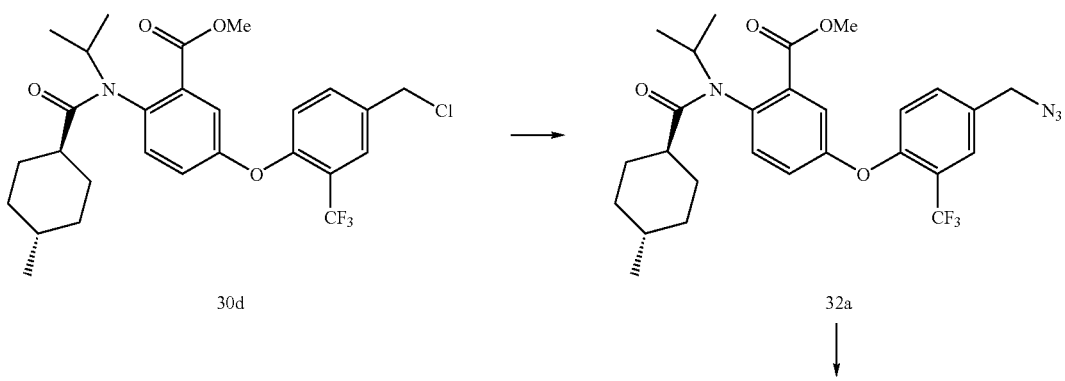

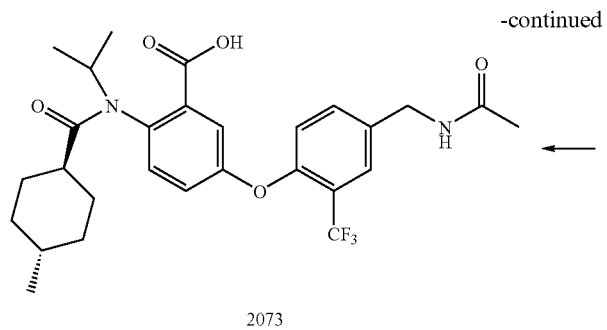

2073

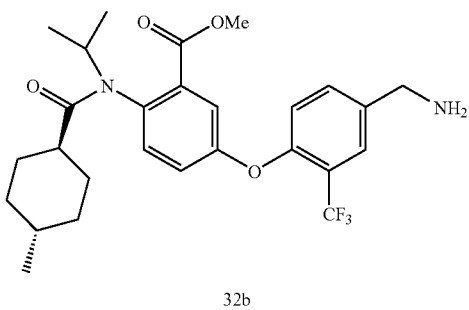

32b

A mixture of compound 30d (Example 30) (0.050 g, 0.10 mmol) and NaN$_3$ (0.008 g, 0.06 mmol) in DMSO (1 mL) is allowed to stir at 65° C. for 40 minutes. The residue is diluted with water and extracted twice with EtOAc. The combined organic extracts are washed with water and brine, dried with MgSO$_4$, filtered and concentrated under reduced pressure to afford azide 32a.

A mixture of azide 32a (0.052 g, 0.1 mmol) and 10% Pd/C (9 mg) in MeOH (1 mL) is stirred under 1 atm of H$_2$ at ambient temperature for 2 hours. The mixture is filtered and concentrated under reduced pressure to afford amine 32b.

A mixture of amine 32b (0.023 g, 0.04 mmol), Ac$_2$O (0.042 mL, 0.44 mmol) and Et$_3$N (0.061 mL, 0.44 mmol) in THF (1 mL) is stirred at room temperature for 16 hours. The mixture is concentrated under reduced pressure and DMSO (0.50 mL), aqueous NaOH (10N, 0.1 mL, 1.0 mmol) and water (0.1 mL) are added to the residue. The mixture is stirred 1 hour at 55° C., then acidified with AcOH and purified by preparative HPLC to afford compound 2073 (Table 2).

Compound 32b is transformed to compound 2072 (Table 2) by hydrolysis with 10N NaOH as described in the last step of Example 32.

Example 33

Inhibition of NS5B RNA Dependent RNA Polymerase Activity

Representative compounds of the invention are tested for inhibitory activity against the hepatitis C virus RNA dependent polymerase (NS5B), according to the protocol described below.

The HCV His-NS5BΔ21 polymerase [SEQ ID NO.1] lacks the C-terminal 21 amino acids and is expressed with an N-terminal hexa-histidine tag from a pET-based vector in *E. coli* strain JM109(DE3) and purified as described in McKercher et al., (2004) Nucleic Acids Res. 32: 422-431. The homogeneous enzyme preparation is stored at −20° C. in storage buffer (25 mM Tris/HCl pH 7.5, 300 mM NaCl, 5 mM DTT, 1 M EDTA and 30% (v/v) glycerol). The purified His-NS5BΔ21 polymerase is reconstituted in an assay that measures the incorporation of $_3$H-UTP during the elongation of a biotin-oligo-(U)$_{12}$ RNA primer annealed to a homopolymeric poly(A) template. The test compound is added first, followed by the substrate, then the enzyme. At the end of the reaction, streptavidin scintillation proximity assay (SPA) beads are added and the radioactivity from the captured double-stranded RNA product is quantified on TopCount instrument (Packard).

The components of the assay reaction are: 20 mM Tris-HCl pH 7.5, 1 mM TCEP, 1 mM EDTA, 5 mM MgCl$_2$, 0.01% w/v BSA, 5% v/v DMSO, 10 µg/mL Poly(A), 1 µg/mL Biotin-oligo-(U)$_{12}$, 333 nM UTP, 0.01 mCi/mL, (300 nM) $_3$H-UTP, 80 units/mL Rnasin, 12.5 nM His-NS5BΔ21 polymerase and test inhibitor compound that is serially diluted over a large concentration range. The assay is performed in 384-well plates with a 1.5 hour incubation at 22° C., and then stopped with a solution of 0.5 M EDTA and the products captured with Streptavidin-coated beads. Following the addition of 6 M CsCl to the bottom of each well, the plate is left at room temperature for 90 minutes before counting for 60 seconds on a TopCount. The calculated % inhibition values are then used to determine IC$_{50}$, slope factor (n) and maximum inhibition (I$_{max}$) by the non-linear regression routine NLIN procedure of SAS.

Example 34

Specificity of NS5B RNA Dependent RNA Polymerase Inhibition

Representative compounds of the invention are tested for inhibitory activity against polio virus RNA dependent RNA polymerase and calf thymus DNA dependent RNA polymerase II as described in McKercher et al., (2004) Nucleic Acids Res. 32: 422-431.

Example 35

Cell-based Luciferase Reporter HCV RNA Replication Assay

Representative compounds of the invention are tested for activity as inhibitors of hepatitis C virus RNA replication in cells expressing a stable subgenomic HCV replicon, using the assay described in WO 2005/028501.

TABLES OF COMPOUNDS

The following tables list compounds representative of the invention. Representative compounds listed in Tables 1 and 2 below are tested in the NS5B polymerase activity inhibition assay of Example 33, and are found to have IC$_{50}$ values below 30 µM. Retention times (t$_R$) for each compound are measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.
TABLE 1
| Cpd | R² | R⁵ | R⁶ | t_R (min) | MS (M + H)⁺ |
|---|---|---|---|---|---|
| 1001 |  | 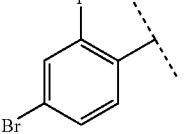 |  | 6.5 | 474.1 |
| 1002 | 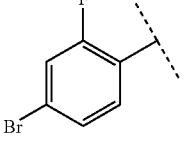 | CH₃ |  | 6.0 | 446.0 |
| 1003 | 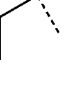 | 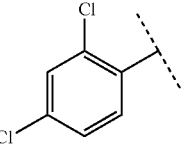 |  | 6.7 | 444.0 |
| 1004 | 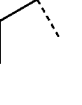 | 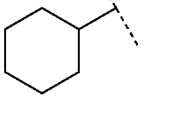 |  | 6.4 | 382.1 |
| 1005 |  | 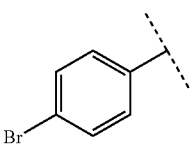 |  | 6.3 | 456.0 |
| 1006 | 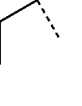 | 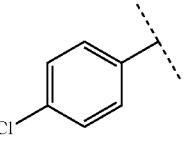 |  | 6.2 | 410.1 |
| 1007 |  | 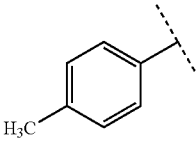 |  | 6.1 | 390.2 |
| 1008 |  | 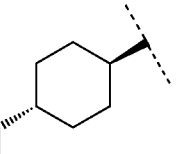 | | 7.0 | 410.2 |

TABLE 1-continued
| Cpd | R² | R⁵ | R⁶ | $t_R$ (min) | MS (M + H)⁺ |
|---|---|---|---|---|---|
| 1009 |  | 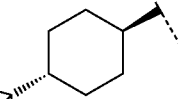 |  | 7.4 | 438.3 |
| 1010 |  | 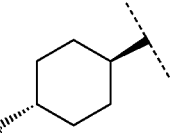 | 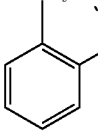 | 6.7 | 450.2 |
| 1011 |  | 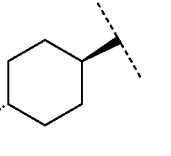 | 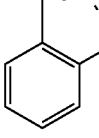 | 7.2 | 478.1 |
| 1012 | 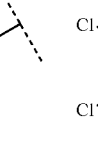 | 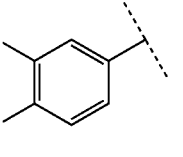 | 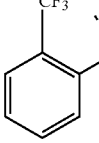 | 7.3 | 512.0 |
| 1013 | 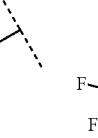 | 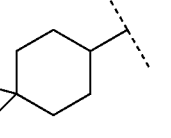 | 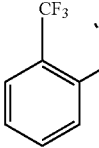 | 6.5 | 484.1 |
| 1014 | 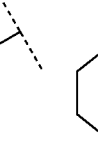 | 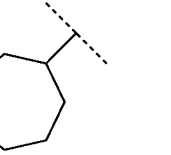 | 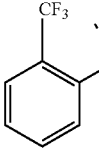 | 7.3 | 464.2 |
| 1015 |  | 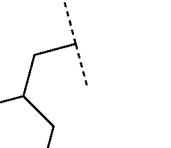 | | 7.4 | 464.2 |

TABLE 1-continued

| Cpd | R² | R⁵ | R⁶ | tR (min) | MS (M + H)⁺ |
|---|---|---|---|---|---|
| 1016 | 2-CF₃-phenyl | isobutyl | 3-CF₃-4-Cl-phenyl | 7.4 | 546.1 |
| 1017 | 2-CF₃-phenyl | isobutyl | 2-Br-4-F... (5-Br-2-F-phenyl) | 7.1 | 540 |
| 1018 | 2-CF₃-phenyl | isobutyl | 3,4-dimethylphenyl | 7.0 | 472.1 |
| 1019 | 2-CF₃-phenyl | isobutyl | 3-Cl-phenyl | 7.0 | 478.1 |
| 1020 | 2-CF₃-phenyl | isobutyl | 4-CF₃-phenyl | 7.1 | 512.1 |
| 1021 | 2-CF₃-phenyl | isobutyl | 4-ethylphenyl | 7.1 | 472.1 |
| 1022 | 2-CF₃-phenyl | isobutyl | 3-CF₃-phenyl | 7.2 | 512.1 |
| 1023 | 2-CF₃-phenyl | isobutyl | 3,5-dimethylphenyl | 7.1 | 472.2 |

TABLE 1-continued
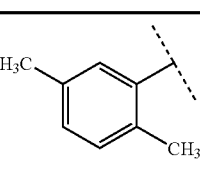
| Cpd | R² | R⁵ | R⁶ | $t_R$ (min) | MS (M + H)⁺ |
|---|---|---|---|---|---|
| 1024 | 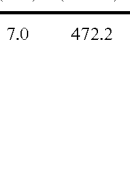 | 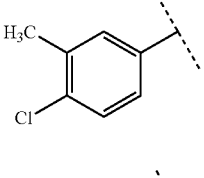 |  | 7.0 | 472.2 |
| 1025 | 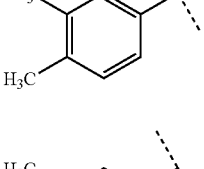 | |  | 7.2 | 492.1 |
| 1026 | 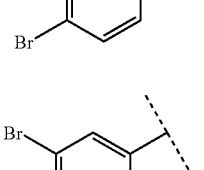 | | 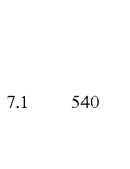 | 7.3 | 526.1 |
| 1027 | 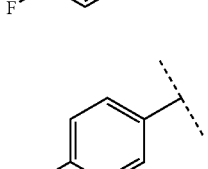 | | 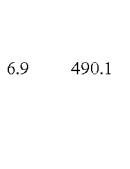 | 7.2 | 536 |
| 1028 | 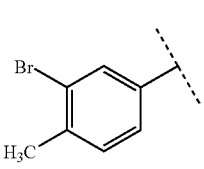 | | 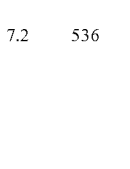 | 7.1 | 540 |
| 1029 | 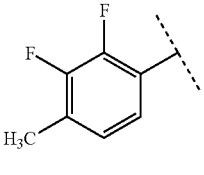 | |  | 6.9 | 490.1 |
| 1030 | | |  | 7.2 | 536 |
| 1031 | | |  | 7.1 | 494.1 |

TABLE 1-continued

| Cpd | R² | R⁵ | R⁶ | t_R (min) | MS (M + H)⁺ |
|---|---|---|---|---|---|
| 1032 | 2-CF₃-phenyl | isobutyl | 3-methyl-4-fluorophenyl | 7.0 | 476.1 |
| 1033 | 2-CF₃-phenyl | isobutyl | 3-chloro-4-methylphenyl | 7.2 | 492.1 |
| 1034 | 2-CF₃-phenyl | isobutyl | 3-bromo-4-chlorophenyl | 7.3 | 556 |
| 1035 | 2-CF₃-phenyl | isobutyl | 3-chloro-4-fluorophenyl | 7.1 | 496 |
| 1036 | 2-CF₃-phenyl | isobutyl | 3-fluoro-4-chlorophenyl | 7.1 | 496.1 |
| 1037 | 2-CF₃-phenyl | isobutyl | 2-fluoro-4-bromophenyl | 7.2 | 540 |
| 1038 | 2-CF₃-phenyl | isobutyl | 3-fluoro-4-bromophenyl | 7.1 | 540 |
| 1039 | 2-CF₃-phenyl | 4-piperidinyl | 3,4-dimethylphenyl | 5.4 | 513.1 |

TABLE 1-continued
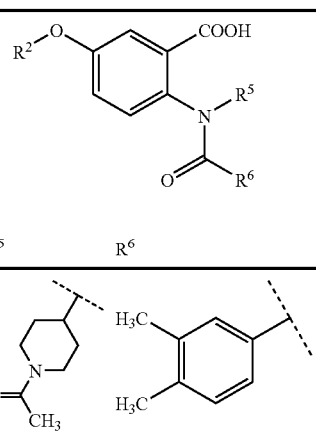
| Cpd | R² | R⁵ | R⁶ | $t_R$ (min) | MS (M + H)⁺ |
|---|---|---|---|---|---|
| 1040 | 2-CF₃-phenyl | 1-acetyl-piperidin-4-yl | 3,4-dimethylphenyl | 6.2 | 555.1 |
| 1041 | 2-CF₃-phenyl | 1-methyl-piperidin-4-yl | 3,4-dimethylphenyl | 5.4 | 527.1 |
| 1042 | 2-CF₃-phenyl | isobutyl | 4-CF₃-cyclohexyl | 6.9 | 518.1 |
| 1043 | 2-CF₃-phenyl | isobutyl | 2-bromo-6-methylphenyl | 7.2 | 536 |
| 1044 | 2-CF₃-phenyl | isobutyl | 2-chloro-6-methylphenyl | 7.2 | 492.1 |
TABLE 2
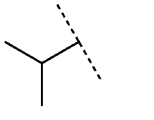
| Cpd | R² | X | R³ | R⁵ | $t_R$ (min) | MS (M + H)⁺ |
|---|---|---|---|---|---|---|
| 2001 | phenyl | O | H | isobutyl | 6.8 | 396.1 |

TABLE 2-continued

| Cpd | R² | X | R³ | R⁵ | t_R (min) | MS (M + H)⁺ |
|---|---|---|---|---|---|---|
| 2002 | 2-(CF₃)-phenyl | O | H | isobutyl | 7.0 | 464.1 |
| 2003 | 2-(OCF₃)-phenyl | O | H | isobutyl | 7.0 | 480.2 |
| 2004 | 4-F-phenyl | O | H | isobutyl | 6.7 | 414.2 |
| 2005 | naphthalen-2-yl | O | H | isobutyl | 7.3 | 446.2 |
| 2006 | naphthalen-1-yl | O | H | isobutyl | 7.3 | 446.2 |
| 2007 | phenyl | O | F | isobutyl | 6.7 | 414.2 |
| 2008 | 2-(CF₃)-phenyl | O | H | H | 7.2 | 422.1 |
| 2009 | 2-(CF₃)-phenyl | O | OCH₃ | isobutyl | 6.8 | 492.4 |

TABLE 2-continued

| Cpd | R² | X | R³ | R⁵ | t_R (min) | MS (M + H)⁺ |
|---|---|---|---|---|---|---|
| 2010 | 3-biphenyl | O | H | isobutyl | 7.9 | 472.2 |
| 2011 | 2-(trifluoromethyl)phenyl | O | N,N-diethylamino-methyl | isobutyl | 7.0 | 521.2 |
| 2012 | 2-(trifluoromethyl)phenyl | O | F | isobutyl | 7.0 | 482.1 |
| 2013 | 2-(trifluoromethyl)phenyl | S | H | isobutyl | 7.2 | 480.1 |
| 2014 | 2-bromophenyl | O | H | isobutyl | 7.0 | 474.0 |
| 2015 | 3-(trifluoromethyl)-4-morpholinophenyl | O | H | isobutyl | 7.0 | 549.2 |
| 2016 | 4-iodo-2-(trifluoromethyl)phenyl | O | H | isobutyl | 6.5 | 590 |

TABLE 2-continued

| Cpd | R² | X | R³ | R⁵ | t_R (min) | MS (M + H)⁺ |
|---|---|---|---|---|---|---|
| 2017 | 2-CF₃-phenyl | O | Br | isobutyl | 7.7 | 544 |
| 2018 | 4-(OtBu-O-C(O)-NH)-phenyl | O | H | isobutyl | 7.0 | 511.2 |
| 2019 | 4-(H₂N)-phenyl | O | H | isobutyl | 4.4 | 411.2 |
| 2020 | 4-CF₃-phenyl | O | H | isobutyl | 7.2 | 464.2 |
| 2021 | 3-CF₃-phenyl | O | H | isobutyl | 7.2 | 464.2 |
| 2022 | 4-(CH₃-C(O)-NH)-phenyl | O | H | isobutyl | 5.6 | 453.1 |

TABLE 2-continued

| Cpd | R² | X | R³ | R⁵ | t_R (min) | MS (M + H)⁺ |
|---|---|---|---|---|---|---|
| 2023 | 4-(HNC(O)CH₂CH₂COOH)-phenyl | O | H | isobutyl | 5.4 | 511.1 |
| 2024 | 2-(CF₃)-phenyl | O | CH₃ | isobutyl | 7.7 | 478 |
| 2025 | 4-(HNC(O)-N(4-methylpiperazine))-phenyl | O | H | isobutyl | 4.9 | 537.2 |
| 2026 | 4-(HNC(O)NH-CH₂CH₂-N(CH₃)₂)-phenyl | O | H | isobutyl | 5.7 | 525.3 |
| 2027 | 3-methyl-4-(HOOC)-phenyl | O | H | isobutyl | 6.1 | 454.2 |

TABLE 2-continued

| Cpd | R² | X | R³ | R⁵ | $t_R$ (min) | MS (M + H)⁺ |
|---|---|---|---|---|---|---|
| 2028 | 2-CF₃-phenyl | O | H | 4-(N-Boc)piperidinyl | 7.5 | 605.2 |
| 2029 | 2-CF₃-phenyl | O | H | 4-piperidinyl | 5.8 | 505.2 |
| 2030 | 2-Cl-phenyl | O | H | isobutyl | 7.0 | 430.1 |
| 2031 | 2-CF₃-phenyl | O | H | tetrahydropyran-4-yl | 6.8 | 506.1 |
| 2032 | 2-CF₃-phenyl | O | H | 1-methylpiperidin-4-yl | 5.8 | 519.2 |
| 2033 | 2-CF₃-phenyl | O | H | 1-acetylpiperidin-4-yl | 6.6 | 547.2 |

TABLE 2-continued
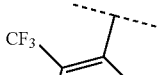
| Cpd | R² | X | R³ | R⁵ | t_R (min) | MS (M + H)⁺ |
|---|---|---|---|---|---|---|
| 2034 |  | O | H | 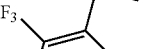 | 6.6 | 590.2 |
| 2035 |  | O | H | 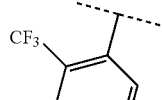 | 6.0 | 575.2 |
| 2036 |  | O | H | 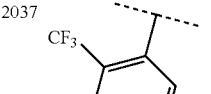 | 7.1 | 626.2 |
| 2037 |  | O | H | | 7.1 | 646.3 |

TABLE 2-continued

| Cpd | R² | X | R³ | R⁵ | t_R (min) | MS (M + H)⁺ |
|---|---|---|---|---|---|---|
| 2038 | 4-(4-carbamoylpiperidin-1-yl)-2-(trifluoromethyl)phenyl | O | H | isobutyl | 5.6 | 590.2 |
| 2039 | 4-(3-methylpiperidin-1-yl)-2-(trifluoromethyl)phenyl | O | H | isobutyl | 7.2 | 561.2 |
| 2040 | 4-(4-methylpiperidin-1-yl)-2-(trifluoromethyl)phenyl | O | H | isobutyl | 7.2 | 561.2 |

TABLE 2-continued

| Cpd | R² | X | R³ | R⁵ | t_R (min) | MS (M + H)⁺ |
|---|---|---|---|---|---|---|
| 2041 | 4-(4-acetyl-1,4-diazepan-1-yl)-2-(trifluoromethyl)phenyl | O | H | isobutyl | 6.7 | 604.2 |
| 2042 | 4-[(2-methoxyethyl)(methyl)amino]-2-(trifluoromethyl)phenyl | O | H | isobutyl | 7.4 | 551.2 |
| 2043 | 4-[4-(pyridin-4-yl)piperazin-1-yl]-2-(trifluoromethyl)phenyl | O | H | isobutyl | 5.6 | 625.2 |

TABLE 2-continued

| Cpd | R² | X | R³ | R⁵ | t_R (min) | MS (M + H)⁺ |
|---|---|---|---|---|---|---|
| 2044 | 4-(4-(2-fluorophenyl)piperazin-1-yl)-2-(trifluoromethyl)phenyl | O | H | isobutyl | 8.3 | 642.2 |
| 2045 | 4-(4-(2-hydroxyethyl)piperidin-1-yl)-2-(trifluoromethyl)phenyl | O | H | isobutyl | 5.6 | 591.2 |
| 2046 | 4-(pyrrolidin-1-yl)-2-(trifluoromethyl)phenyl | O | H | isobutyl | 8.1 | 533.2 |
| 2047 | 4-(2,5-dimethylpyrrolidin-1-yl)-2-(trifluoromethyl)phenyl | O | H | isobutyl | 7.2 | 561.2 |

TABLE 2-continued

| Cpd | R² | X | R³ | R⁵ | t_R (min) | MS (M + H)⁺ |
|---|---|---|---|---|---|---|
| 2048 | 4-(3-hydroxypyrrolidin-1-yl)-2-(trifluoromethyl)phenyl | O | H | isobutyl | 6.8 | 549.2 |
| 2049 | 4-[(2S)-2-(methoxymethyl)pyrrolidin-1-yl]-2-(trifluoromethyl)phenyl | O | H | isobutyl | 8.0 | 577.2 |
| 2050 | 4-(2-methylpyrrolidin-1-yl)-2-(trifluoromethyl)phenyl | O | H | isobutyl | 8.1 | 547.2 |
| 2051 | 4-(3-acetamidopyrrolidin-1-yl)-2-(trifluoromethyl)phenyl | O | H | isobutyl | 6.6 | 590.2 |

TABLE 2-continued

| Cpd | R² | X | R³ | R⁵ | t_R (min) | MS (M + H)⁺ |
|---|---|---|---|---|---|---|
| 2052 | 3-CF₃, 4-(2-(MeOCH₂)-pyrrolidin-1-yl)phenylmethyl | O | H | isobutyl | 7.96 | 577.2 |
| 2053 | 3-CF₃, 4-(3-(dimethylamino)pyrrolidin-1-yl)phenylmethyl | O | H | isobutyl | 5.2 | 576.2 |
| 2054 | 3-CF₃, 4-(2-(CF₃)-pyrrolidin-1-yl)phenylmethyl | O | H | isobutyl | 8.0 | 601.2 |
| 2055 | 3-CF₃, 4-(dimethylamino)phenylmethyl | O | H | isobutyl | 7.3 | 507.2 |

TABLE 2-continued

| Cpd | R² | X | R³ | R⁵ | t_R (min) | MS (M + H)⁺ |
|---|---|---|---|---|---|---|
| 2056 | 4-(diethylamino)-2-(trifluoromethyl)phenylmethyl | O | H | isobutyl | 6.4 | 535.2 |
| 2057 | 4-(piperidin-1-yl)-2-(trifluoromethyl)phenylmethyl | O | H | isobutyl | 6.7 | 547.2 |
| 2058 | 4-carboxy-2-(trifluoromethyl)phenylmethyl | O | H | isobutyl | 6.6 | 508.1 |
| 2059 | 2-(trifluoromethyl)phenylmethyl | O | H | 1-(methylsulfonyl)piperidin-4-yl | 6.9 | 583.1 |
| 2060 | 2-(trifluoromethyl)phenylmethyl | O | H | 1-(ethylcarbamoyl)piperidin-4-yl | 6.7 | 576.2 |

TABLE 2-continued

[Structure: benzoic acid core with R²-X- and R³- substituents on the ring, and an N(R⁵)-C(O)-cyclohexyl-CH₃ (trans) amide group]

| Cpd | R² | X | R³ | R⁵ | t_R (min) | MS (M + H)⁺ |
|---|---|---|---|---|---|---|
| 2061 | 2-(CF₃)phenyl | O | H | 1-(methoxycarbonyl)piperidin-4-yl | 7.0 | 563.2 |
| 2062 | 2-(CF₃)phenyl | O | H | —CH₂CH₃ | 7.0 | 450.1 |
| 2063 | 2-(CF₃)phenyl | O | H | —CH₃ | 6.8 | 436.1 |
| 2064 | 4-carbamoyl-2-(CF₃)phenyl | O | H | isobutyl | 6.0 | 507.1 |
| 2065 | 4-(N,N-dimethylcarbamoyl)-2-(CF₃)phenyl | O | H | isobutyl | 6.4 | 535.2 |

TABLE 2-continued

| Cpd | R² | X | R³ | R⁵ | t_R (min) | MS (M + H)⁺ |
|---|---|---|---|---|---|---|
| 2066 | 3-CF₃-4-(morpholine-4-carbonyl)phenyl | O | H | isobutyl | 6.4 | 577.2 |
| 2067 | 3-CF₃-4-(3-(dimethylamino)pyrrolidine-1-carbonyl)phenyl | O | H | isobutyl | 4.8 | 604.2 |
| 2068 | 2-acetyl-6-(trifluoromethyl)phenyl | O | H | isobutyl | 7.0 | 506.1 |
| 2069 | 4-acetyl-2-(trifluoromethyl)phenyl | O | H | isobutyl | 7.2 | 506.1 |
| 2070 | 2-(trifluoromethyl)phenyl | O | H | -CH₂CH₂COOH | 6.4 | 480.0 |

TABLE 2-continued

| Cpd | R² | X | R³ | R⁵ | t_R (min) | MS (M + H)⁺ |
|---|---|---|---|---|---|---|
| 2071 | 4-(morpholinomethyl)-2-(trifluoromethyl)phenyl | O | H | isobutyl | 5.0 | 563.2 |
| 2072 | 4-(aminomethyl)-2-(trifluoromethyl)phenyl | O | H | isobutyl | 4.8 | 493.1 |
| 2073 | 4-(acetamidomethyl)-2-(trifluoromethyl)phenyl | O | H | isobutyl | 6.1 | 535.2 |
| 2074 | 4-(pyridin-4-yl)-2-(trifluoromethyl)phenyl | O | H | isobutyl | 5.2 | 541 |

TABLE 2-continued

![structure: R2-X, COOH, R3, N-R5, C(=O)-cyclohexyl-CH3 (trans)]

| Cpd | R² | X | R³ | R⁵ | t_R (min) | MS (M + H)⁺ |
|---|---|---|---|---|---|---|
| 2075 | 4-(pyridin-3-yl)-2-(CF₃)phenyl | O | H | isobutyl | 5.4 | 541 |
| 2076 | 4-(1-methyl-1H-pyrazol-4-yl)-2-(CF₃)phenyl | O | H | isobutyl | 7.0 | 544 |
| 2077 | 4-(pyrimidin-5-yl)-2-(CF₃)phenyl | O | H | isobutyl | 6.8 | 542 |
| 2078 | 4-[(3S)-3-(dimethylamino)pyrrolidin-1-yl]-2-(CF₃)phenyl | O | H | isobutyl | 6.0 | 576.2 |

TABLE 2-continued

| Cpd | R² | X | R³ | R⁵ | t_R (min) | MS (M + H)⁺ |
|---|---|---|---|---|---|---|
| 2079 | 3-CF₃, 4-(3-(dimethylamino)pyrrolidin-1-yl)phenyl | O | H | isobutyl | 6.0 | 576.2 |
| 2080 | 2-CF₃-phenyl | O | H | 2-hydroxybutyl | 6.6 | 480.1 |
| 2081 | 3-CF₃, 4-(N-(pyridin-3-yl)carbamoyl)phenyl | O | H | isobutyl | 5.4 | 584.2 |
| 2082 | 3-CF₃, 4-(N-(pyrazin-2-yl)carbamoyl)phenyl | O | H | isobutyl | 6.8 | 585.2 |
| 2083 | 3-CF₃, 4-(N-(1H-pyrazol-3-yl)carbamoyl)phenyl | O | H | isobutyl | 6.3 | 573.2 |

TABLE 2-continued

| Cpd | R² | X | R³ | R⁵ | t_R (min) | MS (M + H)⁺ |
|---|---|---|---|---|---|---|
| 2084 | 4-(thiazol-2-ylcarbamoyl)-2-CF₃-phenyl | O | H | isobutyl | 7.2 | 590.2 |
| 2085 | 4-(imidazol-1-ylmethyl)-2-CF₃-phenyl | O | H | isobutyl | 5.1 | 544.2 |
| 2086 | 4-(pyrazol-1-ylmethyl)-2-CF₃-phenyl | O | H | isobutyl | 7.0 | 544.2 |
| 2087 | 4-(imidazol-1-yl)-2-CF₃-phenyl | O | H | isobutyl | 5.0 | 530.2 |
| 2088 | 4-amino-2-CF₃-phenyl | O | H | isobutyl | 5.8 | 479.1 |

TABLE 2-continued
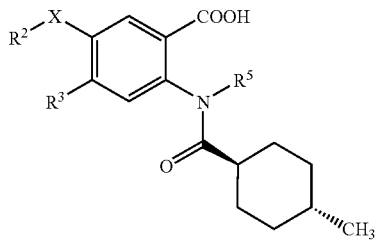
| Cpd | R² | X | R³ | R⁵ | t_R (min) | MS (M + H)⁺ |
|-----|----|---|----|----|-----------|-------------|
| 2089 | 4-(indol-1-yl)-2-(trifluoromethyl)phenyl | O | H | isobutyl | 8.2 | 579.2 |
| 2090 | 4-(indazol-1-yl)-2-(trifluoromethyl)phenyl | O | H | isobutyl | 8.0 | 580.2 |
| 2091 | 4-(3,5-dimethylpyrazol-1-yl)-2-(trifluoromethyl)phenyl | O | H | isobutyl | 7.4 | 558.2 |
| 2092 | 4-(pyrazol-1-yl)-2-(trifluoromethyl)phenyl | O | H | isobutyl | 7.4 | 530.1 |

TABLE 2-continued

| Cpd | R² | X | R³ | R⁵ | t_R (min) | MS (M + H)⁺ |
|---|---|---|---|---|---|---|
| 2093 | 4-(1H-1,2,4-triazol-1-yl)-2-(trifluoromethyl)phenyl | O | H | isobutyl | 6.6 | 531.2 |
| 2094 | 4-(2-methyl-1H-imidazol-1-yl)-2-(trifluoromethyl)phenyl | O | H | isobutyl | 5.0 | 544.2 |
| 2095 | 4-(1H-benzimidazol-1-yl)-2-(trifluoromethyl)phenyl | O | H | isobutyl | 6.0 | 580.2 |
| 2096 | 4-(3-amino-1H-1,2,4-triazol-1-yl)-2-(trifluoromethyl)phenyl | O | H | isobutyl | 6.0 | 546.2 |

TABLE 2-continued

| Cpd | R² | X | R³ | R⁵ | t_R (min) | MS (M + H)⁺ |
|---|---|---|---|---|---|---|
| 2097 | 4-(4-methylpyrazol-1-yl)-2-(trifluoromethyl)phenyl | O | H | isobutyl | 7.6 | 544.2 |
| 2098 | 4-(3-methylpyrazol-1-yl)-2-(trifluoromethyl)phenyl | O | H | isobutyl | 7.6 | 544.2 |
| 2099 | 4-(4-methylimidazol-1-yl)-2-(trifluoromethyl)phenyl | O | H | isobutyl | 5.0 | 544.2 |
| 2100 | 4-(3-aminopyrazol-1-yl)-2-(trifluoromethyl)phenyl | O | H | isobutyl | 6.2 | 545.2 |

TABLE 2-continued
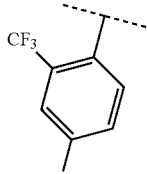
| Cpd | R² | X | R³ | R⁵ | t_R (min) | MS (M + H)⁺ |
|---|---|---|---|---|---|---|
| 2101 |  | O | H | 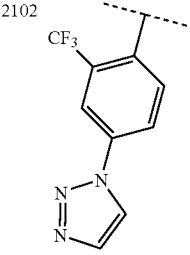 | 5.2 | 558.2 |
| 2102 |  | O | H | 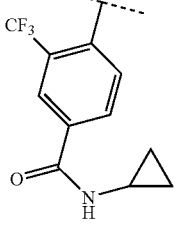 | 7.6 | 531.2 |
| 2103 |  | O | H | 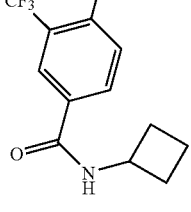 | 6.7 | 547.1 |
| 2104 |  | O | H | 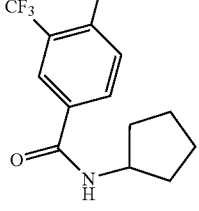 | 7.2 | 561.1 |
| 2105 |  | O | H | | 7.3 | 575.2 |

TABLE 2-continued

| Cpd | R² | X | R³ | R⁵ | t_R (min) | MS (M + H)⁺ |
|---|---|---|---|---|---|---|
| 2106 | 3-CF₃, 4-(C(O)NH-iPr)-phenyl | O | H | isobutyl | 7.0 | 549.2 |
| 2107 | 3-CF₃, 4-(C(O)NH-CH(CH₃)CH₂OH)-phenyl | O | H | isobutyl | 6.0 | 565.1 |
| 2108 | 3-CF₃, 4-(C(O)NH-CH(Et)CH₂OH)-phenyl | O | H | isobutyl | 6.3 | 579.2 |
| 2109 | 3-CF₃, 4-(C(O)NH-CH₂CF₃)-phenyl | O | H | isobutyl | 7.2 | 589.1 |
| 2110 | 3-CF₃, 4-(C(O)NH-CH₂CH(OH)CH₃)-phenyl | O | H | isobutyl | 6.0 | 565.2 |

TABLE 2-continued

| Cpd | R² | X | R³ | R⁵ | $t_R$ (min) | MS (M + H)⁺ |
|---|---|---|---|---|---|---|
| 2111 | 4-CF₃, 3-(C(O)NH-ethyl)phenyl | O | H | isobutyl | 6.7 | 535.1 |
| 2112 | 4-CF₃, 3-(C(O)NH-CH₂CH₂N(CH₃)₂)phenyl | O | H | isobutyl | 4.9 | 578.2 |
| 2113 | 4-CF₃, 3-(C(O)NH-propyl)phenyl | O | H | isobutyl | 7.0 | 549.2 |
| 2114 | 4-CF₃, 3-(C(O)NH-CH₂CN)phenyl | O | H | isobutyl | 6.6 | 544.1 (M-H)⁻ |

TABLE 2-continued

| Cpd | R² | X | R³ | R⁵ | t_R (min) | MS (M + H)⁺ |
|---|---|---|---|---|---|---|
| 2115 | 3-CF₃, 4-(C(O)NHCH₂CH₂CN)-phenyl | O | H | isobutyl | 6.4 | 560.1 |
| 2116 | 3-CF₃, 4-(C(O)NHCH₂CH₂OEt)-phenyl | O | H | isobutyl | 6.8 | 579.2 |
| 2117 | 3-CF₃, 4-(C(O)NHCH₂-cyclopropyl)-phenyl | O | H | isobutyl | 7.1 | 561.2 |
| 2118 | 3-CF₃, 4-(C(O)NHCH(CH₃)CH₂OH)-phenyl | O | H | isobutyl | 6.0 | 565.2 |

TABLE 2-continued

| Cpd | R² | X | R³ | R⁵ | t_R (min) | MS (M + H)⁺ |
|---|---|---|---|---|---|---|
| 2119 | 3-CF₃-4-(C(O)NH-CH(CH₃)CH₂OH)-phenyl | O | H | isobutyl | 6.0 | 565.2 |
| 2120 | 3-CF₃-4-(C(O)NH-CH(CH₂CH₃)CH₂OH)-phenyl | O | H | isobutyl | 6.3 | 579.2 |
| 2121 | 3-CF₃-4-(C(O)-(3-hydroxypyrrolidin-1-yl))-phenyl | O | H | isobutyl | 5.7 | 577.2 |
| 2122 | 3-CF₃-4-(C(O)-(3-hydroxypyrrolidin-1-yl))-phenyl | O | H | isobutyl | 5.7 | 577.2 |

TABLE 2-continued

| Cpd | R² | X | R³ | R⁵ | t_R (min) | MS (M + H)⁺ |
|---|---|---|---|---|---|---|
| 2123 | 3-CF₃, 4-(C(O)NHCH₂CH(OH)CH₃)-phenyl | O | H | isobutyl (sec-butyl-like) | 6.1 | 579.2 |
| 2124 | 3-CF₃, 4-(NHC(O)CH₃)-phenyl | O | H | isobutyl | 6.5 | 521.1 |
| 2125 | 3-CF₃, 4-(C(O)CH₃)-phenyl | O | H | —CH₂CH₃ | 6.9 | 492.1 |
| 2126 | 3-CF₃, 4-(SO₂NH₂)-phenyl | O | H | isobutyl | 6.3 | 543.1 |
| 2127 | 3-CF₃, 4-(C(O)CH₃)-phenyl | O | H | tetrahydropyran-4-yl | 6.8 | 548.2 |

TABLE 2-continued

| Cpd | R² | X | R³ | R⁵ | t_R (min) | MS (M+H)⁺ |
|---|---|---|---|---|---|---|
| 2128 | 4-HOOC-C₆H₄- | O | H | isobutyl | 5.8 | 440.1 |
| 2129 | 4-(2,6-dimethylmorpholin-4-yl)-2-CF₃-C₆H₃- | O | H | isobutyl | 7.8 | 577.2 |
| 2130 | 4-(4-(thiazol-2-yl)piperazin-1-yl)-2-CF₃-C₆H₃- | O | H | isobutyl | 5.4 | 631.2 |
| 2131 | 4-(isoindolin-2-yl)-2-CF₃-C₆H₃- | O | H | isobutyl | 8.4 | 581.2 |

TABLE 2-continued
| Cpd | R² | X | R³ | R⁵ | t_R (min) | MS (M + H)⁺ |
|---|---|---|---|---|---|---|
| 2132 | 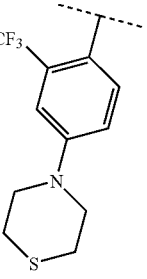 | O | H | 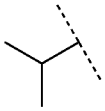 | 7.8 | 565.1 |
| 2133 | 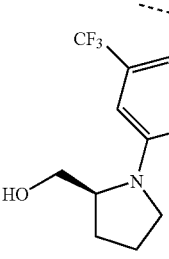 | O | H | 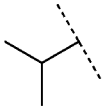 | 7.1 | 563.2 |
| 2134 | 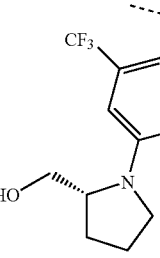 | O | H | 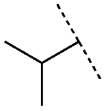 | 7.1 | 563.2 |
| 2135 | 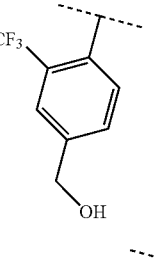 | O | H | 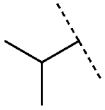 | 6.5 | 494.1 |
| 2136 | 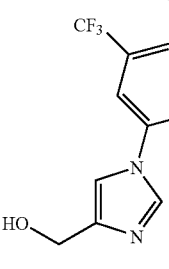 | O | H | 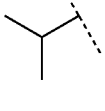 | 4.8 | 560.2 |

TABLE 2-continued

| Cpd | R² | X | R³ | R⁵ | t_R (min) | MS (M + H)⁺ |
|---|---|---|---|---|---|---|
| 2137 | 3-CF₃, 4-(C(O)OCH₂CH(OH)CH₃)-phenyl | O | H | isobutyl | 6.3 | 565.1 |
| 2138 | 3-CF₃, 4-(C(O)NHCH₂CH₂OMe)-phenyl | O | H | isobutyl | 6.4 | 565.2 |
| 2139 | 3-CF₃, 4-(C(O)NHCH₂CH₂OH)-phenyl | O | H | isobutyl | 5.8 | 551.1 |
| 2140 | 3-CF₃, 4-(C(O)NHCH₂CH₂CH₂OH)-phenyl | O | H | isobutyl | 5.9 | 565.2 |

TABLE 2-continued

| Cpd | R² | X | R³ | R⁵ | t_R (min) | MS (M + H)⁺ |
|---|---|---|---|---|---|---|
| 2141 | 3-CF₃, 4-(C(O)NH-CH₂CH₂CH₂-OMe)-phenyl | O | H | isobutyl | 6.6 | 579.2 |
| 2142 | 3-CF₃, 4-(C(O)N(CH₃)-CH₂CH₂-OMe)-phenyl | O | H | isobutyl | 6.6 | 579.2 |

The invention claimed is:

1. A compound of formula I:

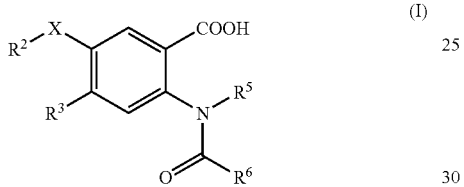

(I)

wherein:

X is selected from O and S;

$R^2$ is phenyl or naphthyl, the phenyl and naphthyl both being optionally substituted with $R^{20}$, wherein $R^{20}$ is 1 to 5 substituents each independently selected from:

a) halo, $(C_{1-6})$alkyl, $(C_{1-6})$haloalkyl, $(C_{3-7})$cycloalkyl, or $(C_{3-7})$cycloalkyl-$(C_{1-6})$alkyl-;

b) —N($R^7$)$R^8$ or —Y—N($R^7$)$R^8$ wherein

Y is selected from —C(=O)—, —SO$_2$— and —(C$_{1-6}$)alkylene-;

$R^7$ is in each instance independently selected from H and $(C_{1-6})$alkyl; and $R^8$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)O$R^9$ and —C(=O) NH$R^9$;

wherein the $(C_{1-6})$alkyl is optionally substituted with —OH, —O—$(C_{1-6})$alkyl, cyano, —NH$_2$, —NH $(C_{1-4})$alkyl or —N(($C_{1-4}$)alkyl)$_2$; and wherein each of the aryl and Het is optionally substituted with 1 to 3 substituents each independently selected from i) halo, —OH, $(C_{1-6})$haloalkyl, —C(=O)—$(C_{1-6})$ alkyl, —SO$_2$($C_{1-6}$)alkyl, —C(=O)—NH$_2$, —C(=O)—NH($C_{1-4}$)alkyl, —C(=O)—N(($C_{1-4}$) alkyl)$_2$, —NH$_2$, —NH($C_{1-4}$)alkyl, —N(($C_{1-4}$) alkyl)$_2$ or —NH—C(=O)($C_{1-4}$)alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and wherein $R^9$ is selected from:

i) $(C_{1-6})$alkyl optionally substituted with —COOH, —NH$_2$, —NH($C_{1-4}$)alkyl or —N(($C_{1-4}$)alkyl)$_2$; and ii) Het optionally substituted with $(C_{1-6})$alkyl; or $R^7$ and $R^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S; the heterocycle and heteropolycycle each being optionally substituted with 1 to 3 substituents each independently selected from:

i) halo, —OH, $(C_{1-6})$haloalkyl, —C(=O)—$(C_{1-6})$ alkyl, —SO$_2$($C_{1-6}$)alkyl, —C(=O)—NH$_2$, —C(=O)—NH($C_{1-4}$)alkyl, —C(=O)—N(($C_{1-4}$) alkyl)$_2$, —NH$_2$, —NH($C_{1-4}$)alkyl, —N(($C_{1-4}$) alkyl)$_2$ or —NH—C(=O)($C_{1-4}$)alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl;

c) aryl, aryl-$(C_{1-6})$alkyl-, Het or Het-$(C_{1-6})$alkyl-, wherein each of the aryl, aryl-$(C_{1-6})$alkyl-, Het and Het-$(C_{1-6})$alkyl- is optionally substituted with 1 to 3 substituents each independently selected from i) halo, —OH, $(C_{1-6})$haloalkyl, —C(=O)—$(C_{1-6})$ alkyl, —SO$_2$($C_{1-6}$)alkyl, —C(=O)—NH$_2$, —C(=O)—NH($C_{1-4}$)alkyl, —C(=O)—N(($C_{1-4}$) alkyl)$_2$, —NH$_2$, —NH($C_{1-4}$)alkyl, —N(($C_{1-4}$) alkyl)$_2$ or —NH—C(=O)($C_{1-4}$)alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and d) —C(=O)—$R^{10}$, —O—$R^{10}$, —C(=O)—O—$R^{10}$, —(C$_{1-6}$)alkylene—O—$R^{10}$, —S—$R^{10}$, —SO—$R^{10}$, —SO$_2$—$R^{10}$, —(C$_{1-6}$)alkylene-S—$R^{10}$, —(C$_{1-6}$) alkylene-SO—$R^{10}$ or —(C$_{1-6}$)alkylene-SO$_2$—$R^{10}$ wherein $R^{10}$ is in each instance independently selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl and Het;

wherein the $(C_{1-6})$alkyl is optionally substituted with —OH, —O—$(C_{1-6})$alkyl, cyano, —NH$_2$, —NH $(C_{1-4})$alkyl or —N(($C_{1-4}$)alkyl)$_2$; and wherein each of the aryl and Het is optionally substituted with 1 to 3 substituents each independently selected from
i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;
ii) $(C_{1-6})$alkyl optionally substituted with —OH or —O—$(C_{1-6})$alkyl; and
iii) aryl or Het, wherein each of the aryl and Het is optionally substituted with halo or $(C_{1-6})$alkyl;

provided that when X is O, $R^2$ is not a group of the formula

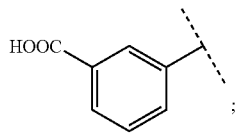

$R^3$ is selected from H, halo, $(C_{1-4})$alkyl, —O—$(C_{1-4})$alkyl, —S—$(C_{1-4})$alkyl, —NH$_2$, —NH$(C_{1-4})$alkyl and —N$((C_{1-4})$alkyl$)_2$;

$R^5$ is selected from H, $(C_{1-6})$alkyl, $(C_{3-7})$cycloalkyl, $(C_{3-7})$cycloalkyl-$(C_{1-3})$alkyl- and Het; the $(C_{1-6})$alkyl and Het each being optionally substituted with 1 to 4 substituents each independently selected from $(C_{1-6})$alkyl, —OH, —COOH, —C(=O)—$(C_{1-6})$alkyl, —C(=O)—O—$(C_{1-6})$alkyl, —C(=O)—NH—$(C_{1-6})$alkyl, —C(=O)—N$((C_{1-6})$alkyl$)_2$, and —SO$_2$$(C_{1-6})$alkyl; and $R^6$ is selected from phenyl, cyclohexyl and cycloheptyl;
the phenyl, cyclohexyl and cycloheptyl each being optionally substituted with 1 to 5 substituents each independently selected from halo, $(C_{1-6})$alkyl, $(C_{1-6})$haloalkyl, —OH, —SH, —O—$(C_{1-4})$alkyl and —S—$(C_{1-4})$alkyl;

wherein Het is a 4- to 7-membered saturated, unsaturated or aromatic heterocycle having 1 to 4 heteroatoms each independently selected from O, N and S, or a 7- to 14-membered saturated, unsaturated or aromatic heteropolycycle having wherever possible 1 to 5 heteroatoms, each independently selected from O, N and S;

or a salt or ester thereof.

2. A compound according to claim 1 wherein X is O.

3. A compound according to claim 1 wherein X is S.

4. A compound according to claim 1 wherein $R^2$ is naphthyl or phenyl, the phenyl being optionally substituted with $R^{20}$ wherein $R^{20}$ is as defined in claim 1;

provided that when X is O, $R^2$ is not a group of the formula

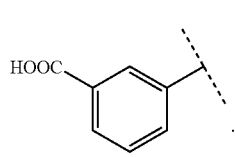

5. A compound according to claim 4 wherein $R^2$ is phenyl optionally substituted with $R^{20}$ wherein $R^{20}$ is as defined in claim 4;

provided that when X is O, $R^2$ is not a group of the formula

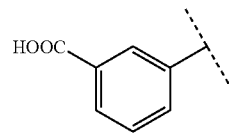

6. A compound according to claim 5 wherein $R^2$ is a group of formula:

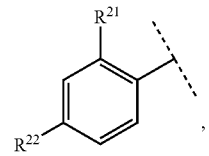

wherein $R^{21}$ is selected from H, halo, $(C_{1-6})$alkyl, $(C_{1-6})$haloalkyl and —O—$(C_{1-6})$haloalkyl; and
$R^{22}$ is selected from H, halo, $(C_{1-3})$alkyl, $(C_{1-3})$haloalkyl, —$(C_{1-3})$alkylene—OH, —C(=O)—$(C_{1-3})$alkyl and —COOH.

7. A compound according to claim 5 wherein $R^2$ is a group of formula:

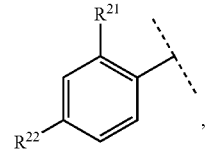

wherein $R^{21}$ is selected from H, halo, $(C_{1-6})$alkyl, $(C_{1-6})$haloalkyl and —O—$(C_{1-6})$haloalkyl; and
$R^{22}$ is selected from:
b) —N$(R^7)R^8$ or —Y—N$(R^7)R^8$ wherein
Y is selected from —C(=O)—, —SO$_2$— and —$(C_{1-6})$alkylene-;
$R^7$ is selected from H and $(C_{1-6})$alkyl; and
$R^8$ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)OR$^9$ and —C(=O)NHR$^9$;
wherein the $(C_{1-6})$alkyl is optionally substituted with —OH, —O—$(C_{1-6})$alkyl, cyano, —NH$_2$, —NH$(C_{1-4})$alkyl or —N$((C_{1-4})$alkyl$)_2$; and
wherein each of the aryl and Het is optionally substituted with 1 to 3 substituents each independently selected from
i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;
ii) $(C_{1-6})$alkyl optionally substituted with —OH or —O—$(C_{1-6})$alkyl; and
iii) aryl or Het, wherein each of the aryl and Het is optionally substituted with halo or $(C_{1-6})$alkyl; and
wherein $R^9$ is selected from:
i) $(C_{1-6})$alkyl optionally substituted with —COOH, —NH$_2$, —NH$(C_{1-4})$alkyl or —N$((C_{1-4})$alkyl$)_2$; and
ii) Het optionally substituted with $(C_{1-6})$alkyl; or R⁷ and R⁸ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S;

the heterocycle and heteropolycycle each being optionally substituted with 1 to 3 substituents each independently selected from:

i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and c) aryl, Het or Het-$(C_{1-6})$alkyl-, wherein each of the aryl, Het and Het-$(C_{1-6})$alkyl-, is optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl.

8. A compound according to claim 7 wherein $R^2$ is a group of formula:

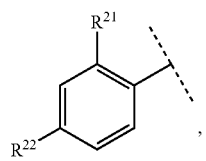

wherein $R^{21}$ is CF$_3$; and $R^{22}$ is selected from:

b) —N($R^7$)$R^8$ wherein $R^7$ is selected from H and $(C_{1-6})$alkyl; and $R^8$ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)O$R^9$ and —C(=O)NH$R^9$;

wherein the $(C_{1-6})$alkyl is optionally substituted with —OH, —O—$(C_{1-6})$alkyl, cyano, —NH$_2$, —NH$(C_{1-4})$alkyl or —N$((C_{1-4})$alkyl$)_2$; and wherein each of the aryl and Het is optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and wherein $R^9$ is selected from:

i) $(C_{1-6})$alkyl optionally substituted with —COOH, —NH$_2$, —NH$(C_{1-4})$alkyl or —N$((C_{1-4})$alkyl$)_2$; and ii) Het optionally substituted with $(C_{1-6})$alkyl; or $R^7$ and $R^9$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S;

the heterocycle and heteropolycycle each being optionally substituted with 1 to 3 substituents each independently selected from:

i) halo, —OH, $(C_{1-6})$haloalkyl, —C(=O)-$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl; and c) Het optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) $(C_{1-6})$alkyl optionally substituted with —OH or —O—$(C_{1-6})$alkyl; and iii) aryl or Het, wherein each of the aryl and Het is optionally substituted with halo or $(C_{1-6})$alkyl.

9. A compound according to claim 7 wherein $R^2$ is a group of formula:

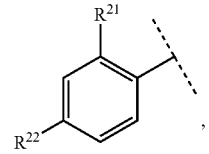

wherein $R^{21}$ is CF$_3$; and $R^{22}$ is selected from:

b) —Y—N($R^7$)$R^8$ wherein

Y is selected from —C(=O)—, —SO$_2$— and —CH$_2$—;

$R^7$ is selected from H and $(C_{1-6})$alkyl; and $R^8$ is selected from H, $(C_{1-6})$alkyl, $(C_{1-6})$haloalkyl, $(C_{3-7})$cycloalkyl, $(C_{3-7})$cycloalkyl-$(C_{1-6})$alkyl-, aryl, Het, —C(=O)—$R^9$, —C(=O)O$R^9$ and —C(=O)NH$R^9$;

wherein the $(C_{1-6})$alkyl is optionally substituted with —OH, —O—$(C_{1-6})$alkyl, cyano, —NH$_2$, —NH$(C_{1-4})$alkyl or —N$((C_{1-4})$alkyl$)_2$; and wherein each of the aryl and Het is optionally substituted with 1 to 3 substituents each independently selected from i) halo, —OH, $(C_{1-6})$haloalkyl, —C(=O)—$(C_{1-6})$alkyl, —SO$_2$$(C_{1-6})$alkyl, —C(=O)—NH$_2$, —C(=O)—NH$(C_{1-4})$alkyl, —C(=O)—N$((C_{1-4})$alkyl$)_2$, —NH$_2$, —NH$(C_{1-4})$alkyl, —N$((C_{1-4})$alkyl$)_2$ or —NH—C(=O)$(C_{1-4})$alkyl;

ii) (C$_{1-6}$)alkyl optionally substituted with —OH or —O—(C$_{1-6}$)alkyl; and
iii) aryl or Het, wherein each of the aryl and Het is optionally substituted with halo or (C$_{1-6}$)alkyl; and
wherein R$^9$ is selected from:
i) (C$_{1-6}$)alkyl optionally substituted with —COOH, —NH$_2$, —NH(C$_{1-4}$)alkyl or —N((C$_{1-4}$)alkyl)$_2$; and
ii) Het optionally substituted with (C$_{1-6}$)alkyl; or
R$^7$ and R$^8$ are linked together with the N to which they are attached to form a 4- to 7-membered heterocycle optionally containing 1 to 3 additional heteroatoms each independently selected from N, O and S, or a 7- to 14-membered heteropolycycle optionally containing 1 to 3 additional heteroatoms each independently selected from N, O and S;
the heterocycle and heteropolycycle each being optionally substituted with 1 to 3 substituents each independently selected from:
i) halo, —OH, (C$_{1-6}$)haloalkyl, —C(=O)—(C$_{1-6}$)alkyl, —SO$_2$(C$_{1-6}$)alkyl, —C(=O)—NH$_2$, —C(=O)—NH(C$_{1-4}$)alkyl, —C(=O)—N((C$_{1-4}$)alkyl)$_2$, —NH$_2$, —NH(C$_{1-4}$)alkyl, —N((C$_{1-4}$)alkyl)$_2$ or —NH—C(=O)(C$_{1-4}$)alkyl;
ii) (C$_{1-6}$)alkyl optionally substituted with —OH or —O—(C$_{1-6}$)alkyl; and
iii) aryl or Het, wherein each of the aryl and Het is optionally substituted with halo or (C$_{1-6}$)alkyl; and
c) Het-(C$_{1-6}$)alkyl-, optionally substituted with 1 to 3 substituents each independently selected from
i) halo, —OH, (C$_{1-6}$)haloalkyl, —C(=O)—(C$_{1-6}$)alkyl, —SO$_2$(C$_{1-6}$)alkyl, —C(=O)—NH$_2$, —C(=O)—NH(C$_{1-4}$)alkyl, —C(=O)—N((C$_{1-4}$)alkyl)$_2$, —NH$_2$, —NH(C$_{1-4}$)alkyl, —N((C$_{1-4}$)alkyl)$_2$ or —NH—C(=O)(C$_{1-4}$)alkyl;
ii) (C$_{1-6}$)alkyl optionally substituted with —OH or —O—(C$_{1-6}$)alkyl; and
iii) aryl or Het, wherein each of the aryl and Het is optionally substituted with halo or (C$_{1-6}$)alkyl.

10. A compound according to claim 1 wherein R$^3$ is H or F.

11. A compound according to claim 10 wherein R$^3$ is H.

12. A compound according to claim 1 wherein R$^5$ is H or (C$_{1-6}$)alkyl, wherein the (C$_{1-6}$)alkyl is optionally substituted with 1 to 4 substituents each independently selected from —OH, —COOH, —C(=O)—(C$_{1-6}$)alkyl, —C(=O)—O—(C$_{1-6}$)alkyl, —C(=O)—NH—(C$_{1-6}$)alkyl, —C(=O)—N((C$_{1-6}$)alkyl)$_2$, and —SO$_2$(C$_{1-6}$)alkyl.

13. A compound according to claim 12 wherein R$^5$ is 1-methylethyl.

14. A compound according to claim 1 wherein R$^5$ is Het optionally substituted with 1 to 4 substituents each independently selected from (C$_{1-6}$)alkyl, —OH, —COOH, —C(=O)-(C$_{1-6}$)alkyl, —C(=O)—O—(C$_{1-6}$)alkyl, —C(=O)—NH—(C$_{1-6}$)alkyl, —C(=O)—N((C$_{1-6}$)alkyl)$_2$, and —SO$_2$(C$_{1-6}$)alkyl.

15. A compound according to claim 1 wherein R$^6$ is selected from cyclohexyl and cycloheptyl, the cyclohexyl and cycloheptyl each being optionally substituted with 1 to 5 substituents each independently selected from halo, (C$_{1-6}$)alkyl, (C$_{1-6}$)haloalkyl, —OH, —SH, —O—(C$_{1-4}$)alkyl and —S—(C$_{1-4}$)alkyl.

16. A compound according to claim 15 wherein R$^6$ is

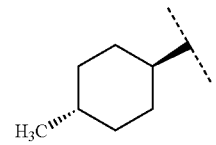

17. A compound according to claim 1 wherein R$^6$ is phenyl optionally substituted with 1 to 5 substituents each independently selected from halo, (C$_{1-6}$)alkyl, (C$_{1-6}$)haloalkyl, —OH, —SH, —O—(C$_{1-4}$)alkyl and —S—(C$_{1-4}$)alkyl.

18. A compound according to claim 1, or a pharmaceutically acceptable salt or ester thereof; as a medicament.

19. A pharmaceutical composition comprising a therapeutically effective amount of a compound according to claim 1, or a pharmaceutically acceptable salt or ester thereof; and one or more pharmaceutically acceptable carriers.

20. The pharmaceutical composition according to claim 19 additionally comprising at least one other antiviral agent.

21. A method of treating a hepatitis C viral infection in a mammal, the method comprising administering to the mammal a therapeutically effective amount of a compound according to claim 1, a pharmaceutically acceptable salt or ester thereof.

22. A method of treating a hepatitis C viral infection in a mammal, the method comprising administering to the mammal a therapeutically effective amount of a combination of a compound according to claim 1 or a pharmaceutically acceptable salt or ester thereof, and at least one other antiviral agent.

23. An article of manufacture comprising a composition effective to treat a hepatitis C viral infection; and packaging material comprising a label which indicates that the composition can be used to treat infection by the hepatitis C virus; wherein the composition comprises a compound according to claim 1 or a pharmaceutically acceptable salt or ester thereof.

24. A method of inhibiting the replication of hepatitis C virus comprising exposing the virus to an effective amount of the compound according to claim 1, or a salt or ester thereof.

* * * * *

SEQUENCE LISTING

<160> NUMBER OF SEQ ID NOS: 1

<210> SEQ ID NO 1
<211> LENGTH: 591
<212> TYPE: PRT
<213> ORGANISM: Artificial Sequence
<220> FEATURE:
<223> OTHER INFORMATION: HCV NS5B

<400> SEQUENCE: 1

```
Met Gly Ser Ser His His His His His His Ser Ser Gly Leu Val Pro
1               5                   10                  15

Arg Gly Ser His Met Ser Met Ser Tyr Thr Trp Thr Gly Ala Leu Ile
            20                  25                  30

Thr Pro Cys Ala Ala Glu Glu Ser Gln Leu Pro Ile Asn Ala Leu Ser
        35                  40                  45

Asn Ser Leu Val Arg His Arg Asn Met Val Tyr Ser Thr Thr Ser Arg
    50                  55                  60

Ser Ala Ala Leu Arg Gln Lys Lys Val Thr Phe Asp Arg Leu Gln Val
65                  70                  75                  80
```

-continued

```
Leu Asp Asp His Tyr Arg Asp Val Leu Lys Glu Met Lys Ala Lys Ala
                85                  90                  95

Ser Thr Val Lys Ala Lys Leu Leu Ser Val Glu Glu Ala Cys Lys Leu
            100                 105                 110

Thr Pro Pro His Ser Ala Lys Ser Lys Phe Gly Tyr Gly Ala Lys Asp
        115                 120                 125

Val Arg Asn Leu Ser Ser Lys Ala Val Asp His Ile Arg Ser Val Trp
    130                 135                 140

Lys Asp Leu Leu Glu Asp Thr Glu Thr Pro Ile Asp Thr Thr Ile Met
145                 150                 155                 160

Ala Lys Asn Glu Val Phe Cys Val Gln Pro Glu Lys Gly Gly Arg Lys
                165                 170                 175

Pro Ala Arg Leu Ile Val Phe Pro Asp Leu Gly Val Arg Val Cys Glu
            180                 185                 190

Lys Met Ala Leu Tyr Asp Val Val Ser Thr Leu Pro Gln Ala Val Met
        195                 200                 205

Gly Ser Ser Tyr Gly Phe Gln Tyr Ser Pro Lys Gln Arg Val Glu Phe
    210                 215                 220

Leu Val Asn Ala Trp Lys Ser Lys Lys Cys Pro Met Gly Phe Ser Tyr
225                 230                 235                 240

Asp Thr Arg Cys Phe Asp Ser Thr Val Thr Glu Ser Asp Ile Arg Val
                245                 250                 255

Glu Glu Ser Ile Tyr Gln Cys Cys Asp Leu Ala Pro Glu Ala Arg Gln
            260                 265                 270

Ala Ile Lys Ser Leu Thr Glu Arg Leu Tyr Ile Gly Gly Pro Leu Thr
        275                 280                 285

Asn Ser Lys Gly Gln Asn Cys Gly Tyr Arg Arg Cys Arg Ala Ser Gly
    290                 295                 300

Val Leu Thr Thr Ser Cys Gly Asn Thr Leu Thr Cys Tyr Leu Lys Ala
305                 310                 315                 320

Ser Ala Ala Cys Arg Ala Ala Lys Leu Gln Asp Cys Thr Met Leu Val
                325                 330                 335

Asn Gly Asp Asp Leu Val Val Ile Cys Glu Ser Ala Gly Thr Gln Glu
            340                 345                 350

Asp Ala Ala Asn Leu Arg Val Phe Thr Glu Ala Met Thr Arg Tyr Ser
        355                 360                 365

Ala Pro Pro Gly Asp Leu Pro Gln Pro Glu Tyr Asp Leu Glu Leu Ile
    370                 375                 380

Thr Ser Cys Ser Ser Asn Val Ser Val Ala His Asp Ala Ser Gly Lys
385                 390                 395                 400

Arg Val Tyr Tyr Leu Thr Arg Asp Pro Thr Thr Pro Leu Ala Arg Ala
                405                 410                 415

Ala Trp Glu Thr Ala Arg His Thr Pro Ile Asn Ser Trp Leu Gly Asn
            420                 425                 430

Ile Ile Met Tyr Ala Pro Thr Leu Trp Ala Arg Met Val Leu Met Thr
        435                 440                 445

His Phe Phe Ser Ile Leu Leu Ala Gln Glu Gln Leu Glu Lys Ala Leu
    450                 455                 460

Asp Cys Gln Ile Tyr Gly Ala Cys Tyr Ser Ile Glu Pro Leu Asp Leu
465                 470                 475                 480

Pro Gln Ile Ile Glu Arg Leu His Gly Leu Ser Ala Phe Ser Leu His
                485                 490                 495
```

```
                                        -continued
Ser Tyr Ser Pro Gly Glu Ile Asn Arg Val Ala Ser Cys Leu Arg Lys
            500                 505                 510

Leu Gly Val Pro Pro Leu Arg Val Trp Arg His Arg Ala Arg Ser Val
            515             520                 525

Arg Ala Lys Leu Leu Ser Gln Gly Gly Arg Ala Ala Thr Cys Gly Lys
530                         535                 540

Tyr Leu Phe Asn Trp Ala Val Arg Thr Lys Leu Lys Leu Thr Pro Ile
545                     550                 555                 560

Pro Ala Ala Ser Arg Leu Asp Leu Ser Gly Trp Phe Val Ala Gly Tyr
                565             570                     575

Asn Gly Gly Asp Ile Tyr His Ser Leu Ser Arg Ala Arg Pro Arg
                580                 585                 590
```